(12) United States Patent
Jansen et al.

(10) Patent No.: US 10,240,217 B2
(45) Date of Patent: *Mar. 26, 2019

(54) METHODS AND SYSTEMS FOR PROCESSING SUGAR MIXTURES AND RESULTANT COMPOSITIONS

(71) Applicant: Virdia, Inc., Raceland, LA (US)

(72) Inventors: Robert Jansen, Collinsville, IL (US); Aharon Eyal, Jerusalem (IL)

(73) Assignee: Virdia, Inc., Raceland, LA (US)

( * ) Notice: Subject to any disclaimer, the term of this patent is extended or adjusted under 35 U.S.C. 154(b) by 292 days.

This patent is subject to a terminal disclaimer.

(21) Appl. No.: 14/033,205

(22) Filed: Sep. 20, 2013

(65) Prior Publication Data

US 2014/0175331 A1  Jun. 26, 2014

Related U.S. Application Data

(63) Continuation of application No. 13/225,346, filed on Sep. 2, 2011, now abandoned.

(60) Provisional application No. 61/529,277, filed on Aug. 31, 2011.

(30) Foreign Application Priority Data

Sep. 2, 2010 (IL) .......................................... 207945
Jun. 1, 2011 (WO) .................. PCT/IL2011/000424
Jun. 26, 2011 (WO) .................. PCT/IL2011/000509
Jun. 28, 2011 (WO) .................. PCT/IL2011/000517

(51) Int. Cl.
| | | |
|---|---|---|
| *C13K 13/00* | (2006.01) | |
| *C07H 1/00* | (2006.01) | |
| *C07H 3/00* | (2006.01) | |
| *C12P 7/10* | (2006.01) | |
| *C12P 7/14* | (2006.01) | |
| *C13K 1/00* | (2006.01) | |
| *C13K 1/02* | (2006.01) | |
| *A23K 20/163* | (2016.01) | |
| *A23K 50/10* | (2016.01) | |

(52) U.S. Cl.
CPC .......... *C13K 13/002* (2013.01); *A23K 20/163* (2016.05); *A23K 50/10* (2016.05); *C07H 1/00* (2013.01); *C07H 3/00* (2013.01); *C12P 7/10* (2013.01); *C12P 7/14* (2013.01); *C13K 1/00* (2013.01); *C13K 1/02* (2013.01); *C13K 13/007* (2013.01); *Y02E 50/16* (2013.01); *Y02E 50/343* (2013.01); *Y10T 428/13* (2015.01); *Y10T 428/139* (2015.01); *Y10T 428/1352* (2015.01); *Y10T 442/60* (2015.04)

(58) Field of Classification Search
CPC .......... C13K 1/00; C13K 1/02; C13K 13/007; C13K 13/002; A23K 50/10; A23K 20/163; C07H 3/00; C07H 1/00; C12P 7/14; C12P 7/10; Y02E 50/343; Y02E 50/16; Y10T 428/13; Y10T 428/1352; Y10T 428/139; Y10T 442/60
USPC .......................................................... 435/134
See application file for complete search history.

(56) References Cited

U.S. PATENT DOCUMENTS

| | | |
|---|---|---|
| 1,344,671 A | 6/1920 | Bergius |
| 1,391,664 A | 9/1921 | Bergius |
| 1,457,791 A | 6/1923 | Norris |
| 1,544,149 A | 6/1925 | Hagglund |
| 1,547,893 A | 7/1925 | Bergius |
| 1,678,819 A | 7/1928 | Koch |
| 1,688,726 A | 10/1928 | McKee |
| 1,699,177 A | 1/1929 | Bergius |
| 1,818,618 A | 8/1931 | Hagglund |
| 1,890,491 A | 12/1932 | Bergius |
| 1,919,623 A | 7/1933 | Dreyfus |
| 2,008,284 A | 7/1935 | Koch et al. |
| 2,146,326 A | 2/1939 | Bergius et al. |
| 2,239,095 A | 4/1941 | Hasche |
| 2,305,833 A | 12/1942 | Warth |
| 2,347,945 A | 5/1944 | Frey |
| 2,357,838 A | 9/1944 | Mahoney et al. |
| 2,391,149 A | 12/1945 | Frey |
| 2,440,442 A | 4/1948 | Hillyer et al. |
| 2,474,669 A | 6/1949 | Hereng |
| 2,752,270 A | 6/1956 | Specht |
| 2,778,751 A | 1/1957 | Riehm |
| 2,813,810 A | 11/1957 | Smith et al. |
| 2,842,591 A | 7/1958 | Shelton |

(Continued)

FOREIGN PATENT DOCUMENTS

| | | |
|---|---|---|
| CA | 2735396 A1 | 3/2010 |
| CN | 102433358 B | 10/2013 |

(Continued)

OTHER PUBLICATIONS

Amartey et al., Comparison of corn steep liquor with other nutrients in the fermentation of D-xylose by Pichia Stipitis CBS 6054, Biotechnology Letters, vol. 16, No. 2 (Feb. 1004), pp. 211-214.*

Saska et al., Aqueous Extraction of Sugarcane Bagasse Hemicellulose and Production of Xylose Syrup, Biotechnology and Bioengineering, vol. 45, (1995), pp. 517-523.*

Bustos et al., Modeling of the Hydrolysis of Sugar Cane Bagasse with Hydrochloric Acid, Applied Biochemistry and Biotechnology, vol. 104 (2003) pp. 51-68.*

(Continued)

*Primary Examiner* — Jennifer M. H. Tichy
(74) *Attorney, Agent, or Firm* — Wilson Sonsini Goodrich & Rosati

(57) ABSTRACT

A method including: (a) selectively reacting a first sugar in a mixture which includes at least one second sugar to form a product mixture comprising a product of said first sugar; (b) separating said product of said first sugar from said product mixture; and (c) separating at least one of said at least one second sugar from said product mixture.

22 Claims, 16 Drawing Sheets

(56) References Cited

U.S. PATENT DOCUMENTS

| | | |
|---|---|---|
| 2,890,972 A | 6/1959 | Wheaton |
| 2,894,813 A | 7/1959 | Baniel et al. |
| 2,902,341 A | 9/1959 | Baniel et al. |
| 2,917,390 A | 12/1959 | Apel et al. |
| 2,944,923 A | 7/1960 | Riehm |
| 2,945,777 A | 7/1960 | Riehm |
| 2,951,775 A | 9/1960 | Apel |
| 2,989,569 A | 6/1961 | Apel |
| 3,067,065 A | 4/1962 | Kusama |
| 3,097,177 A | 7/1963 | Emerson et al. |
| 3,131,027 A | 4/1964 | Borkowski |
| 3,132,051 A | 5/1964 | Nobile et al. |
| 3,186,809 A | 6/1965 | Kreevoy et al. |
| 3,251,716 A | 5/1966 | Porter et al. |
| 3,311,450 A | 3/1967 | Alon et al. |
| 3,312,683 A | 4/1967 | Farkas et al. |
| 3,326,944 A | 6/1967 | Lew |
| 3,432,569 A | 3/1969 | Folz |
| 3,497,330 A | 2/1970 | Baniel et al. |
| 3,527,820 A | 9/1970 | Mercier |
| 3,704,168 A | 11/1972 | Hara et al. |
| 3,792,183 A | 2/1974 | Lyall et al. |
| 3,812,010 A | 5/1974 | Nitsch et al. |
| 3,824,161 A | 7/1974 | Aue et al. |
| 3,839,318 A | 10/1974 | Mansfield |
| 3,939,803 A | 2/1976 | Meissner et al. |
| 4,014,711 A | 3/1977 | Odawara et al. |
| 4,016,054 A | 4/1977 | Gandon et al. |
| 4,018,637 A | 4/1977 | Kimmel |
| 4,025,357 A | 5/1977 | Leiser et al. |
| 4,102,705 A | 7/1978 | Pfeiffer et al. |
| 4,115,530 A | 9/1978 | Coenen et al. |
| 4,165,240 A | 8/1979 | Enokizono et al. |
| 4,174,976 A | 11/1979 | Tsao et al. |
| 4,206,302 A | 6/1980 | Pollozec |
| 4,230,681 A | 10/1980 | Coenen et al. |
| 4,237,110 A | 12/1980 | Forster et al. |
| 4,257,818 A | 3/1981 | Regnault et al. |
| 4,259,309 A | 3/1981 | Coenen et al. |
| 4,272,492 A | 6/1981 | Jensen |
| 4,272,502 A | 6/1981 | Ziegenbein et al. |
| 4,277,560 A | 7/1981 | Gray et al. |
| 4,277,626 A | 7/1981 | Forss et al. |
| 4,278,471 A | 7/1981 | Whittingham |
| 4,291,007 A | 9/1981 | Baniel |
| 4,299,677 A | 11/1981 | Venkatasubramanian et al. |
| 4,304,608 A | 12/1981 | Regnault et al. |
| 4,420,644 A | 12/1983 | Huibers et al. |
| 4,425,136 A | 1/1984 | Pearson et al. |
| 4,439,408 A | 3/1984 | Baniel et al. |
| 4,470,851 A | 9/1984 | Paszner et al. |
| 4,472,501 A | 9/1984 | Takasawa et al. |
| 4,474,736 A | 10/1984 | Andrews et al. |
| 4,497,896 A | 2/1985 | Assarsson et al. |
| 4,503,278 A | 3/1985 | Chen et al. |
| 4,516,566 A | 5/1985 | Chao et al. |
| 4,520,105 A | 5/1985 | Sinner et al. |
| 4,523,928 A | 6/1985 | Hillman et al. |
| 4,533,743 A | 8/1985 | Medeiros |
| 4,556,432 A | 12/1985 | Erckel et al. |
| 4,579,595 A | 4/1986 | Sachetto |
| 4,608,245 A | 8/1986 | Gaddy et al. |
| 4,615,742 A | 10/1986 | Wright |
| 4,645,658 A | 2/1987 | Gaddy et al. |
| 4,668,340 A | 5/1987 | Sherman |
| 4,677,198 A | 6/1987 | Linnett et al. |
| 4,681,639 A | 7/1987 | Hinck-Hinck |
| 4,701,414 A | 10/1987 | Van Dijken et al. |
| 4,710,567 A | 12/1987 | Kea et al. |
| 4,713,413 A | 12/1987 | Tegge et al. |
| 4,814,015 A | 3/1989 | Quinlan |
| 4,836,995 A | 6/1989 | Manor et al. |
| 4,840,903 A | 6/1989 | Wu |
| 4,890,820 A | 1/1990 | Tucker |
| 4,901,635 A | 2/1990 | Williams |
| 4,934,177 A | 6/1990 | Cuthbertson et al. |
| 4,958,016 A | 9/1990 | Kerkenaar et al. |
| 4,990,696 A | 2/1991 | Stauffer |
| 5,049,494 A | 9/1991 | Allenza |
| 5,081,026 A | 1/1992 | Heikkila et al. |
| 5,114,491 A | 5/1992 | Sarhaddar |
| 5,132,476 A | 7/1992 | Osterburg et al. |
| 5,138,110 A | 8/1992 | Segall et al. |
| 5,174,865 A | 12/1992 | Stultz et al. |
| 5,176,832 A | 1/1993 | Dorta et al. |
| 5,182,199 A | 1/1993 | Hartley |
| 5,205,473 A | 4/1993 | Coffin, Sr. |
| 5,227,446 A | 7/1993 | Denzinger et al. |
| 5,244,553 A | 9/1993 | Goldstein |
| 5,332,842 A | 7/1994 | Dickakian |
| 5,338,405 A | 8/1994 | Patt et al. |
| 5,340,403 A | 8/1994 | Fields et al. |
| 5,357,035 A | 10/1994 | Gruber et al. |
| 5,398,497 A | 3/1995 | Suppes |
| 5,407,580 A | 4/1995 | Hester et al. |
| 5,411,594 A | 5/1995 | Brelsford |
| 5,421,964 A | 6/1995 | Mahler et al. |
| 5,487,989 A | 1/1996 | Fowler et al. |
| 5,503,996 A | 4/1996 | Torget et al. |
| 5,538,637 A | 7/1996 | Hester et al. |
| 5,571,378 A | 11/1996 | Elofson et al. |
| 5,580,389 A | 12/1996 | Farone et al. |
| 5,597,714 A | 1/1997 | Farone et al. |
| 5,602,286 A | 2/1997 | Muralidhara |
| 5,635,152 A | 6/1997 | Walpole |
| 5,696,195 A | 12/1997 | Tuminello et al. |
| 5,698,667 A | 12/1997 | Speaks et al. |
| 5,705,369 A | 1/1998 | Torget et al. |
| 5,723,704 A | 3/1998 | Demail et al. |
| 5,726,046 A | 3/1998 | Farone et al. |
| 5,730,837 A | 3/1998 | Black et al. |
| 5,730,877 A | 3/1998 | Heikkila et al. |
| 5,767,330 A | 6/1998 | Metz et al. |
| 5,782,982 A | 7/1998 | Farone et al. |
| 5,800,624 A | 9/1998 | Smith et al. |
| 5,820,687 A | 10/1998 | Farone et al. |
| 5,831,122 A | 11/1998 | Eyak |
| 5,837,831 A | 11/1998 | Gruning |
| 5,840,358 A | 11/1998 | Hofler et al. |
| 5,846,510 A | 12/1998 | Hollitt |
| 5,847,238 A | 12/1998 | Muralidhara et al. |
| 5,856,261 A | 1/1999 | Culross et al. |
| 5,859,270 A | 1/1999 | Kolstad et al. |
| 5,865,948 A | 2/1999 | Lora et al. |
| 5,876,505 A | 3/1999 | Klyosov et al. |
| 5,959,128 A | 9/1999 | Kolstad et al. |
| 5,969,195 A | 10/1999 | Stabel et al. |
| 6,001,410 A | 12/1999 | Bolen et al. |
| 6,007,636 A | 12/1999 | Lightner |
| 6,043,392 A | 3/2000 | Holtzapple et al. |
| 6,086,681 A | 7/2000 | Lindroos et al. |
| 6,114,475 A | 9/2000 | Goode et al. |
| 6,124,443 A | 9/2000 | Darsow |
| 6,136,868 A | 10/2000 | Culross et al. |
| 6,169,187 B1 | 1/2001 | Eyal |
| 6,207,209 B1 | 3/2001 | Jirjis et al. |
| 6,224,776 B1 | 5/2001 | Heikkila |
| 6,229,046 B1 | 5/2001 | Eyal et al. |
| 6,239,274 B1 | 5/2001 | Heikkila et al. |
| 6,258,175 B1 | 7/2001 | Lightner |
| 6,391,204 B1 | 5/2002 | Russo, Jr. |
| 6,416,621 B1 | 7/2002 | Karstens |
| 6,419,788 B1 | 7/2002 | Wingerson |
| 6,419,828 B1 | 7/2002 | Russo, Jr. |
| 6,451,123 B1 | 9/2002 | Saska et al. |
| 6,452,051 B1 | 9/2002 | Eyal |
| 6,479,713 B1 | 11/2002 | Werpy et al. |
| 6,486,366 B1 | 11/2002 | Ostgard et al. |
| 6,521,097 B2 | 2/2003 | Geissler |
| 6,548,662 B1 | 4/2003 | Ohsaki et al. |
| 6,572,775 B2 | 6/2003 | Heikkila et al. |
| 6,610,867 B2 | 8/2003 | Jakel et al. |
| 6,620,292 B2 | 9/2003 | Wingerson |
| 6,692,578 B2 | 2/2004 | Schmidt et al. |

(56) References Cited

U.S. PATENT DOCUMENTS

| | | |
|---|---|---|
| 6,699,457 B2 | 3/2004 | Cortright et al. |
| 6,747,076 B2 | 6/2004 | Schneider et al. |
| 6,752,902 B2 | 6/2004 | Heikkila et al. |
| 6,824,599 B2 | 11/2004 | Swatloski et al. |
| 6,833,149 B2 | 12/2004 | Jirjis et al. |
| 6,841,085 B2 | 1/2005 | Werpy et al. |
| 6,852,345 B2 | 2/2005 | Hill et al. |
| 6,875,349 B2 | 4/2005 | Heikkila et al. |
| 6,896,811 B2 | 5/2005 | Heikkila et al. |
| 6,924,371 B2 | 8/2005 | Karki et al. |
| 6,936,110 B2 | 8/2005 | Van Thorre |
| 6,942,754 B2 | 9/2005 | Izumi et al. |
| 6,942,803 B2 | 9/2005 | Cockrem et al. |
| 6,953,873 B2 | 10/2005 | Cortright et al. |
| 6,964,757 B2 | 11/2005 | Cortright et al. |
| 6,964,758 B2 | 11/2005 | Cortright et al. |
| 7,022,239 B2 | 4/2006 | Heikkila et al. |
| 7,026,152 B2 | 4/2006 | Ingram et al. |
| 7,037,378 B2 | 5/2006 | Jumppanen et al. |
| 7,038,094 B2 | 5/2006 | Werpy et al. |
| 7,109,005 B2 | 9/2006 | Eroma et al. |
| 7,198,925 B2 | 3/2007 | Foody |
| 7,208,570 B2 | 4/2007 | Saviainen |
| 7,229,558 B2 | 6/2007 | Heikkila et al. |
| 7,361,273 B2 | 4/2008 | Heikkila et al. |
| 7,399,323 B2 | 7/2008 | Renninger et al. |
| 7,465,791 B1 | 12/2008 | Hallberg et al. |
| 7,498,430 B2 | 3/2009 | Hollingsworth |
| 7,501,025 B2 | 3/2009 | Bakker et al. |
| 7,503,981 B2 | 3/2009 | Wyman et al. |
| 7,524,660 B2 | 4/2009 | Caimi et al. |
| 7,615,652 B2 | 11/2009 | Holladay et al. |
| 7,618,612 B2 | 11/2009 | Cortright et al. |
| 7,629,010 B2 | 12/2009 | Passarelli et al. |
| 7,649,086 B2 | 1/2010 | Belanger et al. |
| 7,652,180 B2 | 1/2010 | Osterholt et al. |
| 7,699,958 B2 | 4/2010 | Griffith et al. |
| 7,704,381 B2 | 4/2010 | Siekmann et al. |
| 7,709,632 B2 | 5/2010 | Johnson et al. |
| 7,713,725 B2 | 5/2010 | England et al. |
| 7,717,364 B2 | 5/2010 | Wingerson |
| 7,718,070 B2 | 5/2010 | Mahnon |
| 7,722,721 B2 | 5/2010 | Heikkila et al. |
| 7,880,049 B2 | 2/2011 | Dumesic et al. |
| 7,901,511 B2 | 3/2011 | Griffin et al. |
| 7,935,156 B2 | 5/2011 | Renninger et al. |
| 7,942,940 B2 | 5/2011 | Renninger et al. |
| 7,947,858 B2 | 5/2011 | Buchert et al. |
| 7,959,811 B2 | 6/2011 | Airaksinen et al. |
| 7,977,517 B2 | 7/2011 | Cortright et al. |
| 7,993,709 B2 | 8/2011 | Brunet |
| 8,017,818 B2 | 9/2011 | Cortright et al. |
| 8,022,260 B2 | 9/2011 | O'Connor et al. |
| 8,026,378 B2 | 9/2011 | Selifonov |
| 8,053,468 B2 | 11/2011 | Selifonov |
| 8,084,508 B2 | 12/2011 | Yakobson et al. |
| 8,084,635 B2 | 12/2011 | Selifonov |
| 8,101,808 B2 | 1/2012 | Evanko et al. |
| 8,152,867 B2 | 4/2012 | Dumenil |
| 8,163,092 B2 | 4/2012 | Baniel et al. |
| 8,178,701 B2 | 5/2012 | Selifonov |
| 8,277,643 B2 | 10/2012 | Huber et al. |
| 8,314,267 B2 | 11/2012 | Brandvold |
| 8,404,355 B2 | 3/2013 | Jansen et al. |
| 8,604,225 B2 | 12/2013 | Pedersen |
| 8,637,660 B2 | 1/2014 | Fanselow et al. |
| 8,637,661 B2 | 1/2014 | Fanselow et al. |
| 8,722,878 B2 | 5/2014 | Raines et al. |
| 8,894,771 B2 | 11/2014 | Floyd et al. |
| 9,410,216 B2 | 8/2016 | Eyal et al. |
| 9,476,106 B2 | 10/2016 | Eyal et al. |
| 9,512,495 B2 | 12/2016 | Eyal |
| 9,617,608 B2 | 4/2017 | Eyal et al. |
| 9,650,687 B2 | 5/2017 | Jansen et al. |
| 9,845,514 B2 | 12/2017 | Eyal et al. |
| 9,963,673 B2 | 5/2018 | Eyal et al. |
| 9,976,194 B2 | 5/2018 | Eyal et al. |
| 2001/0009889 A1 | 7/2001 | Waggenspack et al. |
| 2002/0102672 A1 | 8/2002 | Mizrahi et al. |
| 2002/0153317 A1 | 10/2002 | Heikkila et al. |
| 2002/0164731 A1 | 11/2002 | Eroma et al. |
| 2003/0094416 A1 | 5/2003 | Heikkila et al. |
| 2003/0144387 A1 | 7/2003 | Krivohlavek et al. |
| 2003/0156970 A1 | 8/2003 | Oberkofler et al. |
| 2003/0199049 A1 | 10/2003 | Nguyen et al. |
| 2003/0222021 A1 | 12/2003 | Ennelin et al. |
| 2004/0060673 A1 | 4/2004 | Phillips et al. |
| 2004/0108085 A1 | 6/2004 | Kettenbach et al. |
| 2004/0121446 A1 | 6/2004 | England et al. |
| 2004/0127371 A1 | 7/2004 | Arrowsmith et al. |
| 2004/0149200 A1 | 8/2004 | Shimose et al. |
| 2004/0161388 A1 | 8/2004 | Liu et al. |
| 2004/0199049 A1 | 10/2004 | Parasher et al. |
| 2004/0231661 A1 | 11/2004 | Griffin et al. |
| 2004/0237499 A1 | 12/2004 | Yogev et al. |
| 2005/0034823 A1 | 2/2005 | Brelid et al. |
| 2005/0148056 A1 | 7/2005 | Levine et al. |
| 2005/0181486 A1 | 8/2005 | Zhong et al. |
| 2005/0260229 A1 | 11/2005 | De La Fuente et al. |
| 2006/0024801 A1 | 2/2006 | Holtzapple et al. |
| 2006/0051812 A1 | 3/2006 | Helin et al. |
| 2006/0134308 A1 | 6/2006 | Inglett |
| 2006/0207734 A1 | 9/2006 | Day et al. |
| 2007/0020375 A1 | 1/2007 | Jansen et al. |
| 2007/0031953 A1 | 2/2007 | Dunson, Jr. et al. |
| 2007/0053987 A1 | 3/2007 | Bayer et al. |
| 2007/0112187 A1 | 5/2007 | Heikkila et al. |
| 2007/0178569 A1 | 8/2007 | Leschine et al. |
| 2007/0184555 A1 | 8/2007 | Banavali et al. |
| 2007/0191303 A1 | 8/2007 | Dillon et al. |
| 2007/0219521 A1 | 9/2007 | Hird et al. |
| 2008/0008783 A1 | 1/2008 | Dale |
| 2008/0029233 A1 | 2/2008 | Wingerson et al. |
| 2008/0032344 A1 | 2/2008 | Fallavollita |
| 2008/0033187 A1 | 2/2008 | Zhang |
| 2008/0033188 A1 | 2/2008 | Dumesic et al. |
| 2008/0041366 A1 | 2/2008 | Wahnon |
| 2008/0057555 A1 | 3/2008 | Nguyen |
| 2008/0075806 A1 | 3/2008 | Dorr et al. |
| 2008/0168982 A1 | 7/2008 | Vente et al. |
| 2008/0175977 A1 | 7/2008 | Harrison et al. |
| 2008/0182305 A1 | 7/2008 | Foody et al. |
| 2008/0193989 A1 | 8/2008 | Verser et al. |
| 2008/0202504 A1 | 8/2008 | Hilst |
| 2008/0216391 A1 | 9/2008 | Cortright et al. |
| 2008/0227161 A1 | 9/2008 | Levie et al. |
| 2008/0274528 A1 | 11/2008 | Dixon et al. |
| 2008/0299606 A1 | 12/2008 | Pompejus et al. |
| 2008/0300434 A1 | 12/2008 | Cortright et al. |
| 2008/0300435 A1 | 12/2008 | Cortright et al. |
| 2008/0305210 A1 | 12/2008 | Petersen |
| 2009/0008119 A1 | 1/2009 | Zamfes |
| 2009/0017503 A1 | 1/2009 | Zhang et al. |
| 2009/0053783 A1 | 2/2009 | Gokarn et al. |
| 2009/0056889 A1 | 3/2009 | Ren et al. |
| 2009/0061488 A1 | 3/2009 | Edwards et al. |
| 2009/0062232 A1 | 3/2009 | Fujikawa et al. |
| 2009/0084511 A1 | 4/2009 | Lampinen et al. |
| 2009/0093027 A1 | 4/2009 | Balan et al. |
| 2009/0117634 A1 | 5/2009 | Bradley et al. |
| 2009/0123638 A1 | 5/2009 | Eyal |
| 2009/0124829 A1 | 5/2009 | Gong |
| 2009/0142848 A1 | 6/2009 | Wyman et al. |
| 2009/0155414 A1 | 6/2009 | Abbas et al. |
| 2009/0155873 A1 | 6/2009 | Kashiyama et al. |
| 2009/0173339 A1 | 7/2009 | Heikkilae et al. |
| 2009/0176286 A1 | 7/2009 | O'Connor et al. |
| 2009/0181433 A1 | 7/2009 | Chotani et al. |
| 2009/0203099 A1 | 8/2009 | Caimi et al. |
| 2009/0205086 A1 | 8/2009 | Hood et al. |
| 2009/0215718 A1 | 8/2009 | Van Laere et al. |
| 2009/0218055 A1 | 9/2009 | Unsitalo et al. |
| 2009/0226571 A1 | 9/2009 | Freyer et al. |
| 2009/0226979 A1 | 9/2009 | Retsina et al. |

(56) References Cited

U.S. PATENT DOCUMENTS

| | | |
|---|---|---|
| 2009/0226993 A1 | 9/2009 | Kumar et al. |
| 2009/0229599 A1 | 9/2009 | Zhang et al. |
| 2009/0234142 A1 | 9/2009 | Mascal |
| 2009/0280541 A1* | 11/2009 | Jordan ............... C12P 7/10 435/105 |
| 2009/0286295 A1 | 11/2009 | Medoff et al. |
| 2009/0305942 A1 | 12/2009 | Day et al. |
| 2009/0318679 A1 | 12/2009 | Shin et al. |
| 2010/0004437 A1 | 1/2010 | Binder et al. |
| 2010/0009408 A1 | 1/2010 | England et al. |
| 2010/0012010 A1 | 1/2010 | Gooijer et al. |
| 2010/0024807 A1 | 2/2010 | Burke et al. |
| 2010/0028557 A1 | 2/2010 | Nagano |
| 2010/0043782 A1 | 2/2010 | Kilambi et al. |
| 2010/0043784 A1 | 2/2010 | Jensen |
| 2010/0048884 A1 | 2/2010 | Kilambi |
| 2010/0048924 A1 | 2/2010 | Kilambi |
| 2010/0069626 A1 | 3/2010 | Kilambi |
| 2010/0076233 A1 | 3/2010 | Cortright et al. |
| 2010/0083565 A1 | 4/2010 | Gruter |
| 2010/0086981 A1 | 4/2010 | Latouf et al. |
| 2010/0093995 A1 | 4/2010 | Baniel et al. |
| 2010/0116267 A1 | 5/2010 | Mraz et al. |
| 2010/0124772 A1 | 5/2010 | Sabesan |
| 2010/0136642 A1 | 6/2010 | Belanger et al. |
| 2010/0151527 A1 | 6/2010 | Endo et al. |
| 2010/0170504 A1 | 7/2010 | Zhang |
| 2010/0184151 A1 | 7/2010 | Tolan et al. |
| 2010/0184176 A1 | 7/2010 | Ishida et al. |
| 2010/0189706 A1 | 7/2010 | Chang et al. |
| 2010/0203605 A1 | 8/2010 | Kim et al. |
| 2010/0233761 A1 | 9/2010 | Czartoski et al. |
| 2010/0268000 A1 | 10/2010 | Parekh et al. |
| 2010/0269990 A1 | 10/2010 | Dottori et al. |
| 2010/0279354 A1 | 11/2010 | De Crecy |
| 2010/0279361 A1 | 11/2010 | South et al. |
| 2010/0279372 A1 | 11/2010 | Cho et al. |
| 2010/0305241 A1 | 12/2010 | Balakshin et al. |
| 2010/0305242 A1 | 12/2010 | Balakshin et al. |
| 2010/0305243 A1 | 12/2010 | Balakshin et al. |
| 2010/0305244 A1 | 12/2010 | Balakshin et al. |
| 2011/0003348 A1 | 1/2011 | Genta et al. |
| 2011/0003352 A1 | 1/2011 | Retsina et al. |
| 2011/0016545 A1 | 1/2011 | Gray et al. |
| 2011/0020910 A1 | 1/2011 | Glass et al. |
| 2011/0028672 A1 | 2/2011 | Dahlman et al. |
| 2011/0028710 A1 | 2/2011 | Baniel et al. |
| 2011/0033896 A1 | 2/2011 | Boy et al. |
| 2011/0059316 A1 | 3/2011 | Kilambi et al. |
| 2011/0060132 A1 | 3/2011 | Lewis |
| 2011/0065159 A1 | 3/2011 | Raines et al. |
| 2011/0070131 A1 | 3/2011 | Schmidt et al. |
| 2011/0097776 A1 | 4/2011 | Johnson |
| 2011/0100359 A1 | 5/2011 | North |
| 2011/0105737 A1 | 5/2011 | Benjelloun Mlayah et al. |
| 2011/0124057 A1 | 5/2011 | Genta et al. |
| 2011/0129880 A1 | 6/2011 | Conners et al. |
| 2011/0129886 A1 | 6/2011 | Howard et al. |
| 2011/0143412 A1 | 6/2011 | Kim et al. |
| 2011/0146138 A1 | 6/2011 | Berry et al. |
| 2011/0155559 A1 | 6/2011 | Medoff |
| 2011/0178290 A1 | 7/2011 | Baniel et al. |
| 2011/0183394 A1 | 7/2011 | Bell et al. |
| 2011/0192560 A1 | 8/2011 | Heikkila et al. |
| 2011/0201059 A1 | 8/2011 | Hall et al. |
| 2011/0201072 A1* | 8/2011 | Bastian ............... C12N 9/0006 435/160 |
| 2011/0262984 A1 | 10/2011 | Nguyen |
| 2011/0268652 A1 | 11/2011 | Machhammer et al. |
| 2011/0271875 A1 | 11/2011 | Ahmed et al. |
| 2011/0275860 A1 | 11/2011 | Beldring et al. |
| 2011/0281298 A1 | 11/2011 | Rawls et al. |
| 2011/0300617 A1 | 12/2011 | Genta et al. |
| 2011/0314726 A1 | 12/2011 | Jameel et al. |
| 2011/0318796 A1 | 12/2011 | Walther |
| 2012/0006320 A1 | 1/2012 | Nguyen |
| 2012/0023810 A1 | 2/2012 | Fjare et al. |
| 2012/0036768 A1 | 2/2012 | Phillips et al. |
| 2012/0055466 A1 | 3/2012 | Cotti et al. |
| 2012/0058526 A1 | 3/2012 | Jansen et al. |
| 2012/0104313 A1 | 5/2012 | Garbero et al. |
| 2012/0116063 A1 | 5/2012 | Jansen et al. |
| 2012/0122170 A1 | 5/2012 | Ropars et al. |
| 2012/0134912 A1 | 5/2012 | Baniel et al. |
| 2012/0156517 A1 | 6/2012 | Vuori et al. |
| 2012/0149924 A1 | 7/2012 | Jong |
| 2012/0167874 A1 | 7/2012 | Jansen et al. |
| 2012/0184026 A1 | 7/2012 | Eyal |
| 2012/0264873 A1* | 10/2012 | Eyal ............... C12P 7/10 524/560 |
| 2012/0289692 A1 | 11/2012 | Gray et al. |
| 2012/0304529 A1 | 12/2012 | O'Connor et al. |
| 2012/0308991 A1 | 12/2012 | Eiteman et al. |
| 2012/0323053 A1 | 12/2012 | Qiao et al. |
| 2013/0012610 A1 | 1/2013 | Belanger et al. |
| 2013/0028832 A1 | 1/2013 | Eyal et al. |
| 2013/0028833 A1 | 1/2013 | Eyal et al. |
| 2013/0047979 A1 | 2/2013 | Eyal et al. |
| 2013/0115653 A1 | 5/2013 | Peterson et al. |
| 2013/0167836 A1 | 7/2013 | Floyd et al. |
| 2013/0167837 A1 | 7/2013 | Floyd et al. |
| 2013/0216693 A1 | 8/2013 | Harrison et al. |
| 2013/0217070 A1 | 8/2013 | Zhao et al. |
| 2013/0252312 A1 | 9/2013 | Yoshikuni et al. |
| 2013/0276778 A1 | 10/2013 | Jansen et al. |
| 2014/0014092 A1 | 1/2014 | Kazachkin et al. |
| 2014/0220651 A1 | 8/2014 | Raines et al. |
| 2014/0227161 A1 | 8/2014 | Manesh et al. |
| 2014/0309416 A1 | 10/2014 | Teixeira et al. |
| 2014/0356915 A1 | 12/2014 | Retsina et al. |
| 2015/0020797 A1 | 1/2015 | Eyal et al. |
| 2015/0028255 A1 | 1/2015 | Eyal et al. |
| 2015/0048274 A1 | 2/2015 | Eyal et al. |
| 2015/0144126 A1 | 5/2015 | Jansen et al. |
| 2015/0176090 A1 | 6/2015 | Dumesic et al. |
| 2015/0184261 A1 | 7/2015 | Floyd et al. |
| 2015/0197824 A1 | 7/2015 | Floyd et al. |
| 2016/0108481 A1 | 4/2016 | Eyal et al. |
| 2016/0108482 A1 | 4/2016 | Eyal et al. |
| 2016/0222477 A1 | 8/2016 | Jansen et al. |
| 2017/0369957 A1 | 12/2017 | Jansen et al. |
| 2018/0142314 A1 | 5/2018 | Eyal et al. |

FOREIGN PATENT DOCUMENTS

| | | |
|---|---|---|
| DE | 19721301 C1 | 10/1998 |
| DE | 19747917 A1 | 5/1999 |
| DE | 102008064325 A1 | 7/2010 |
| EP | 0018621 A1 | 11/1980 |
| EP | 0301783 A2 | 2/1989 |
| EP | 0317036 A1 | 5/1989 |
| EP | 0301783 A3 | 4/1991 |
| EP | 0493842 A2 | 7/1992 |
| EP | 0247436 B1 | 8/1992 |
| EP | 0504622 A1 | 9/1992 |
| EP | 0560546 A1 | 9/1993 |
| EP | 0561554 A1 | 9/1993 |
| EP | 0690931 B1 | 10/2001 |
| EP | 1721988 A2 | 11/2006 |
| EP | 1878480 A1 | 1/2008 |
| EP | 1889814 A1 | 2/2008 |
| EP | 1918031 A1 | 7/2008 |
| EP | 1458805 B1 | 8/2011 |
| EP | 1733282 B1 | 1/2012 |
| EP | 2325246 B1 | 11/2013 |
| GB | 1562682 A | 3/1980 |
| GB | 2034291 A | 6/1980 |
| GB | 2488918 B | 3/2014 |
| KR | 20140108301 A | 9/2014 |
| WO | WO 82/01723 A1 | 5/1982 |
| WO | WO 84/03304 A1 | 8/1984 |
| WO | WO 93/05186 A1 | 3/1993 |
| WO | WO 93/13265 A1 | 7/1993 |
| WO | WO-9426380 A1 | 11/1994 |

(56) References Cited

FOREIGN PATENT DOCUMENTS

| | | |
|---|---|---|
| WO | WO 95/02726 A1 | 1/1995 |
| WO | WO 96/27028 A1 | 9/1996 |
| WO | WO 96/41052 A1 | 12/1996 |
| WO | WO 97/13732 A2 | 4/1997 |
| WO | WO 97/13732 A3 | 5/1997 |
| WO | WO 98/56958 A1 | 12/1998 |
| WO | WO 01/25143 A1 | 4/2001 |
| WO | WO 01/32715 A1 | 5/2001 |
| WO | WO 02/02826 A1 | 1/2002 |
| WO | WO-03010339 A1 | 2/2003 |
| WO | WO 03/029329 A2 | 4/2003 |
| WO | WO-03056038 A1 | 7/2003 |
| WO | WO 2004/050983 A1 | 6/2004 |
| WO | WO 2006/006164 A2 | 1/2006 |
| WO | WO 2006/034581 A1 | 4/2006 |
| WO | WO 2006/038863 A1 | 4/2006 |
| WO | WO 2006/056838 A1 | 6/2006 |
| WO | WO 2006/086861 A2 | 8/2006 |
| WO | WO 2006/086861 A3 | 10/2006 |
| WO | WO 2007/019505 A2 | 2/2007 |
| WO | WO 2007/019505 A3 | 6/2007 |
| WO | WO 2007/075476 A2 | 7/2007 |
| WO | WO-2007102638 A1 | 9/2007 |
| WO | WO 2007/112314 A2 | 10/2007 |
| WO | WO 2007/112314 A3 | 11/2007 |
| WO | WO-2007130984 A2 | 11/2007 |
| WO | WO 2007/146245 A2 | 12/2007 |
| WO | WO 2008/019468 A1 | 2/2008 |
| WO | WO 2007/075476 A3 | 3/2008 |
| WO | WO 2008/027699 A2 | 3/2008 |
| WO | WO 2007/146245 A3 | 4/2008 |
| WO | WO 2008/144903 A1 | 4/2008 |
| WO | WO 2008/069830 A2 | 6/2008 |
| WO | WO 2008/027699 A3 | 7/2008 |
| WO | WO 2008/098036 A1 | 8/2008 |
| WO | WO 2008/109877 A1 | 9/2008 |
| WO | WO 2008/111045 A1 | 9/2008 |
| WO | WO 2008/123419 A1 | 10/2008 |
| WO | WO 2008/131229 A1 | 10/2008 |
| WO | WO 2008/069830 A3 | 11/2008 |
| WO | WO 2008/137639 A1 | 11/2008 |
| WO | WO 2009/003292 A1 | 1/2009 |
| WO | WO 2009/015663 A2 | 2/2009 |
| WO | WO 2009/020459 A2 | 2/2009 |
| WO | WO 2009/028969 A1 | 3/2009 |
| WO | WO 2009/030713 A1 | 3/2009 |
| WO | WO 2009/031164 A1 | 3/2009 |
| WO | WO 2009/036674 A1 | 3/2009 |
| WO | WO 2009/020459 A3 | 4/2009 |
| WO | WO 2006/006164 A3 | 5/2009 |
| WO | WO 2009/111026 A2 | 9/2009 |
| WO | WO 2009/125400 A2 | 10/2009 |
| WO | WO 2009/135480 A1 | 11/2009 |
| WO | WO 2009/142837 A2 | 11/2009 |
| WO | WO 2009/015663 A3 | 12/2009 |
| WO | WO-2009155982 A1 | 12/2009 |
| WO | WO 2009/125400 A3 | 1/2010 |
| WO | WO 2010/006840 A2 | 1/2010 |
| WO | WO 2010/009343 A2 | 1/2010 |
| WO | WO 2010/015404 A1 | 2/2010 |
| WO | WO 2010/020977 A2 | 2/2010 |
| WO | WO-2010018105 A1 | 2/2010 |
| WO | WO 2009/142837 A3 | 3/2010 |
| WO | WO 2010/026244 A1 | 3/2010 |
| WO | WO 2010/026572 A1 | 3/2010 |
| WO | WO 2010/009343 A3 | 4/2010 |
| WO | WO 2010/034055 A1 | 4/2010 |
| WO | WO 2010/038021 A2 | 4/2010 |
| WO | WO 2010/043424 A1 | 4/2010 |
| WO | WO 2010/045576 A2 | 4/2010 |
| WO | WO 2010/046532 A1 | 4/2010 |
| WO | WO 2010/046619 A1 | 4/2010 |
| WO | WO 2010/006840 A3 | 5/2010 |
| WO | WO 2010/059825 A1 | 5/2010 |
| WO | WO 2010/060183 A1 | 6/2010 |
| WO | WO 2010/064229 A2 | 6/2010 |
| WO | WO 2010/045576 A3 | 7/2010 |
| WO | WO 2010/064229 A3 | 7/2010 |
| WO | WO 2010/081231 A1 | 7/2010 |
| WO | WO 2010/038021 A3 | 8/2010 |
| WO | WO 2010/088486 A1 | 8/2010 |
| WO | WO 2010/020977 A3 | 10/2010 |
| WO | WO 2010/113129 A2 | 10/2010 |
| WO | WO 2010/113129 A3 | 10/2010 |
| WO | WO 2010/113130 A2 | 10/2010 |
| WO | WO 2010/122554 A1 | 10/2010 |
| WO | WO 2010/128272 A1 | 11/2010 |
| WO | WO 2010/135804 A1 | 12/2010 |
| WO | WO 2010/135805 A1 | 12/2010 |
| WO | WO 2010/135806 A1 | 12/2010 |
| WO | WO 2010/135807 A1 | 12/2010 |
| WO | WO 2010/135832 A1 | 12/2010 |
| WO | WO 2010/135833 A1 | 12/2010 |
| WO | WO 2010/146331 A2 | 12/2010 |
| WO | WO 2010/113130 A3 | 1/2011 |
| WO | WO 2011/002660 A1 | 1/2011 |
| WO | WO 2011/007043 A1 | 1/2011 |
| WO | WO 2011/007369 A1 | 1/2011 |
| WO | WO 2011/017587 A1 | 2/2011 |
| WO | WO 2011/028554 A1 | 3/2011 |
| WO | WO 2011/039751 A2 | 4/2011 |
| WO | WO 2011/066487 A1 | 6/2011 |
| WO | WO 2011/070602 A1 | 6/2011 |
| WO | WO 2011/080131 A2 | 7/2011 |
| WO | WO 2011/089589 A1 | 7/2011 |
| WO | WO-2011091044 A1 | 7/2011 |
| WO | WO 2011/097719 A1 | 8/2011 |
| WO | WO 2011/080131 A3 | 9/2011 |
| WO | WO 2011/111189 A1 | 9/2011 |
| WO | WO 2011/111190 A1 | 9/2011 |
| WO | WO 2010/146331 A3 | 10/2011 |
| WO | WO 2011/039751 A3 | 10/2011 |
| WO | WO 2011/124639 A1 | 10/2011 |
| WO | WO 2011/140222 A1 | 11/2011 |
| WO | WO 2011/151823 A1 | 12/2011 |
| WO | WO 2011/161141 A1 | 12/2011 |
| WO | WO 2011/163084 A1 | 12/2011 |
| WO | WO-2011154604 A1 | 12/2011 |
| WO | WO-2011161685 A2 | 12/2011 |
| WO | WO 2012/015575 A1 | 2/2012 |
| WO | WO 2012/031270 A1 | 3/2012 |
| WO | WO 2012/044168 A1 | 4/2012 |
| WO | WO 2012/060767 A1 | 5/2012 |
| WO | WO-2012085684 A2 | 6/2012 |
| WO | WO-2012137201 A1 | 10/2012 |
| WO | WO 2012/170520 A1 | 12/2012 |
| WO | WO 2013/024162 A1 | 2/2013 |
| WO | WO 2013/038399 A1 | 3/2013 |
| WO | WO 2013/040514 A1 | 3/2013 |
| WO | WO 2013/040702 A1 | 3/2013 |
| WO | WO-2013055785 A1 | 4/2013 |
| WO | WO 2013/083876 A2 | 6/2013 |
| WO | WO-2013166469 A2 | 11/2013 |
| WO | WO 2013/192572 A1 | 12/2013 |
| WO | WO 2014/044753 A1 | 3/2014 |
| WO | WO-2014081605 A1 | 5/2014 |
| WO | WO-2014126471 A1 | 8/2014 |
| WO | WO 2014/138553 A1 | 9/2014 |
| WO | WO 2014/169079 A2 | 10/2014 |
| WO | WO-2015139141 A1 | 9/2015 |
| WO | WO-2016112134 A1 | 7/2016 |
| WO | WO-2016191503 A1 | 12/2016 |

OTHER PUBLICATIONS

Neureiter et al., Dilute-Acid Hydrolysis of Sugarcane Bagasse at Varying Conditions, Applied Biochemistry and Biotechnology, vols. 98-100 (2002) pp. 49-58.*
U.S. Appl. No. 61/358,894, filed Jun. 26, 2010, Eyal.
U.S. Appl. No. 61/473,134, filed Apr. 7, 2011, Eyal.
U.S. Appl. No. 61/483,663, filed May 7, 2011, Eyal.
U.S. Appl. No. 61/483,777, filed May 9, 2011, Jansen et al.
U.S. Appl. No. 61/487,319, filed May 18, 2011, Jansen et al.
U.S. Appl. No. 61/491,243, filed May 30, 2011, Jansen et al.

(56) References Cited

OTHER PUBLICATIONS

U.S. Appl. No. 61/500,169, filed Jun. 23, 2011, Eyal et al.
U.S. Appl. No. 61/513,613, filed Jul. 31, 2011, Jansen et al.
U.S. Appl. No. 61/524,350, filed Aug. 17, 2011, Eyal et al.
U.S. Appl. No. 61/528,257, filed Aug. 28, 2011, Jansen et al.
U.S. Appl. No. 61/539,196, filed Sep. 26, 2011, Jansen et al.
U.S. Appl. No. 61/539,239, filed Sep. 26, 2011, Jansen et al.
U.S. Appl. No. 61/539,272, filed Sep. 26, 2011, Jansen et al.
U.S. Appl. No. 61/545,823, filed Oct. 11, 2011 Jansen, et al.
Aden, et al. Lignocellulosic Biomass to Ethanol Process Design and Economics Utilizing Co-Current Dilute Acid Prehydrolysis and Enzymatic Hydrolysis for Corn Stover. National Renewable Energy Laboratory, NREL is a U.S. Department of Energy Laboratory Operated by Midwest Research Institute. Jun. 2002.
Adina, et al. Application of FTIR Spectroscopy for a Rapid Determination of Some Hydrolytic Enzymes Activity on Sea Buckthorn Substrate. Romanian Biotechnological Letters. 2010; 15(6):5738-5744.
ADM corn 42/43 syrup. Typical data information. Accessed Oct. 5, 2012.
Ahlkvist.J. Formic and Levulinic Acid from Cellulose via Heterogeneous Catalysis. PhD Report. 2014, Sweden.
Ahmed, et al. A simplified method for accurate determination of cell wall uronide content. Journal of Food Biochemistry.1977; 1:361-365.
Ahmed, et al. Preparation and studies on immobilized α-glucosidase from baker's yeast Saccharomyces cerevisiae. J. Serb. Chem. Soc. 2007; 72(12):1255-1263.
Albersheim. Metabolism of the Pectic Substances. For the degree of Doctor of Philosophy, California Institute of Technology Pasadena, California, 1959.
Albertson, et al. Addition Compounds of Sulfur Dioxide. Sep. 1943; 65:1687-1690.
Alizadeh, et al. Pretreatment of Switchgrass by Ammonia Fiber Explosion (AFEX). Applied Biochemistry and Biotechnology. 2005; 5(121-124):1133-1142.
Allsopp, et al. 130. The constitution of the cambium, the new wood and the mature sapwood of the common ash, the common elm and the scotch pine. May 10, 1940; 1078-1084.
Alonso-Fagundez, et al. Selective conversion of furfural to maleic anhydride and furan with VO(x)/Al(2)O(3) catalysts. 2012 ;5: 1984-1990.
Ambalkar, et al. Synthesis of Furfural from Lignocellulosic Biomass as Agricultural Residues : A Review. The International Journal of Engineering and Science. 2012; 1(1): 30-36.
Amidon, et al. Biorefinery: Conversion of Woody Biomass to Chemicals, Energy and Materials. Journal of Biobased Materials and Bioenergy. 2008; 2:100-120.
Anderson. The isolation of pectic substances from wood. 1935; 531-539.
Anellotech. Scaling up economical, non-food biomass derived Benzene, Toluene and Xylenes for major biobased polymers. Presentation by Anellotech; San Francisco. 2013.
Antonoplis, et al. High pressure HCl conversion of cellulose to glucose. Lawrence Berkeley National Laboratory, University of California, Paper LBL,14221. Aug. 1981.
Arborgen. Purpose Grown Trees as an Economical and Sustainable Biomass Feedstock. Southeast Bioenergy conference, Presentation. 2010.
Argyropoulus et al. Bioenergy Program. Presentation; NC State University. 2014.
Atalla, et al. Analysis of Lignin and Cellulose in Biological Energy Sources by Raman Microscopy. 2011.
Atchison, et al. Innovative Methods for Corn Stover Collecting, Handling, Storing and Transporting, Mar. 2003. National Renewable Energy Laboratory. Apr. 2004.
Atsuki. Action of highly concentrated hydrochloric acid on cellulose. Seniso Kogyo (1925), 1 53-61. Coden: SKOGBJ ISSN: 0371-070X. Abstract only.
Badger. Ethanol from cellulose: a general review. Trends in new crops and new uses. 2002; 17-21.
Bakker. Advanced physical/chemical fractionation. Workshop of the EU FP6, Integrated Project Biosynergy. Nov. 17, 2011.
Bao, et al. Preparation of 5-hydroxymethylfurfural by dehydration of fructose in the presence of acidic ionic liquid. Catalysis Communications; 2008; 9: 1383-1388.
Barta, et al. Catalytic disassembly of an organosolv lignin via hydrogen transfer from supercritical methanol.
Barton. CRC handbook of solubility parameters and other cohesion parameters. CRC Press. Boca Raton. 1991; 122-138.
Bayat-Makooi, et al. Hydrolysis of cellulose with hydrochloric acid enhanced by cations. Dep. Wood Paper Sci., North Carolina State Univ., Raleigh, NC, USA. Editor(s): Kennedy, John F. Cellul. Its Deriv. (1985), 135-41. Publisher: Horwood, Chichester, UK Coden: 54GPAW. Abstract only.
Beck, et al. Production of ethanol by bioconversion of wood sugars derived from two-stage dilute acid hydrolysis of hardwood. Biomass. 1984; 6:101-110.
Bergius. Conversion of wood to carbohydrates and problems in the industrial use of concentrated hydrochloric acid. Industrial and Engineering chemistry. 1937; 29(3):247-253.
Bergius. The utilisation of wood for the production of foodstuffs, alcohol and glucose. Chemical society institution. Nov. 15, 1933.
Bergius. Winslow Notes on Bergius Process. 1937.
Bergius. Wood Sugar Plants at Mannheim-Rheinau & Regensburg. 1945.
Berndes, et al. The contribution of biomass in the future global energy supply: a review of 17 studies. Biomass and Bioenergy. 2003; 25:1-28.
Berthold, et al. Association of water to polar groups; estimations by an adsorption model for ligno-cellulosic materials. Colloids Surfaces A:Physicochem. Eng. Aspects. 1996; 112:117-129.
Bilanicova, et al. Improvements in Enzymatic Preparation of Alkyl Glycosides. Czech J. Food Sci. 20101 28(1): 69-73.
Binder, et al. Mechanistic insights on the conversion of sugars into 5-hydroxymethylfurfural. Energy Environ. Sci., 2010; 3:765-771.
Binder, et al. Simple chemical transformation of lignocellulosic biomass into furans for fuels and chemicals. J Am Chem Soc. Feb. 11, 2009;131(5):1979-85. doi: 10.1021/ja808537j.
Blommel, et al. Production of conventional liquid fuels from sugars. Virent energy systems. Aug. 25, 2008. 1-14.
Bo, et al. Mutual Solubilities for Water-o-Nitrotoluene System and Distribution Coefficients for Furfural and Acetic Acid in Water-o-Nitrotoluene System. J. Chem. Eng. Data; 2010;55;5191-5195.
Bochek. Effect of Hydrogen Bonding on Cellulose Solubility in Aqueous and Nonaqueous Solvents. Russian Journal of Applied Chemistry, vol. 76, No. 11, 2003, pp. 1711-1719.
Bozell et al. The Use of Renewable Production of Chemicals andMaterials—A Brief Overview of Concepts. Presentation; National Renewable Energy Laboratory.
Bozell et al. Top Value Added Chemicals from Biomass vol. I—Results of Screening for Potential Candidates from Sugars and Synthesis Gas Top Value Added Chemicals From Biomass vol. I : Results of Screening for Potential Candidates. NREL report.2004: 1-76.
Bozell. The Use of Renewable Feedstocks for the Production of Chemicals and Materials—a Brief Overview of Concepts. National Renewable Energy Laboratory, 1617 Cole Boulevard, Golden, CO 80401. 2010.
Bridgwater, et al. Identification and market analysis of most promising added-value products to be co-produced with the fuels. Project No. 212831, Project end date: May 31, 2010; 1-132.
Brito, et al. Chemical composition changes in eucalyptus and pinus woods submitted to heat treatment. Bioresource Technology. 2008; 99:8545-8548.
Brown, et al. Initial Market Assessment for Small-Scale Biomass-Based CHP, Prepared under Task No. WF6N.1050. National Renewable Energy Laboratory. Jan. 2008.
Brown. Determination of Dry Substance in Beet Sugar Juices, A Precision Method. Industrial and Engineering chemistry. Jul. 1924; 16(7):746-748.

(56) References Cited

OTHER PUBLICATIONS

Brownell, et al. Steam-Explosion Pretreatment of Wood: Effect of Chip Size, Acid, Moisture Content and Pressure Drop. Biotechnology and Bioengineering. 1986; XXVIII:792-801.
Brummer, et al. Understanding Carbohydrate Analysis. Chapter 2. Copyright 2005 by Taylor & Francis Group, LLC.
Brunner. Near critical and supercritical water. Part I. Hydrolytic and hydrothermal processes. J. of Supercritical Fluids. 2009; 47:373-381.
Bulushev, et al. Catalysis for conversion of biomass to fuels via pyrolysis and gasification: A review. Catalysts Today. 2001; 171: 1-13.
Bunker. The Wartime Production of Food Yeast in Germany. 2010.
Burchell, et al. The development of novel activated carbon composites. 17th Annual Conference on Fossil Energy Materials, Wyndham Baltimore Inner Harbor Hotel, Baltimore, Maryland, Apr. 22-24, 2003.
Bustos, et al. Modeling of the Hydrolysis of Sugar Cane Bagasse with Hydrochloric Acid. Applied Biochemistry and Biotechnology. 2003; 104:51-68.
Byrne. Expression, purification and crystallisation of membrane proteins. 2011.
Cai, et al. Integrated furfural production as a renewable fuel and chemical platform from lignocellulosic biomass. J. Chem. Technol. Biotechnol. 2014; 89: 2-10.
Campa et al. Capillary Electrophoresis of Neutral Carbohydrates. Methods in molecular biology.2008; 384:247-305.
Campa et al. Capillary electrophoresis of sugar acids. Methods in molecular biology. 2008; 384: 307-355.
Campbell et al. The bleaching action of alkaline hydrogen peroxide on wood. The Biochemical journal. 1938; 32(4): 702-707.
Campbell,et al. The Saccharification of Wood by the Bergius process at Suddeutschen Holzversucherung Werke A.G. Regensburg. Report on visit to Suddeutschen Holzversucherung Werke A.G. Regensburg.CIOS trip No. 764, this target was visited on Aug. 9, 1945.
Campbell. The Degradation of wood by simultaneous action of ethyl alcohol and hydrochloric acid. 1929; 1225-1232.
Campos. Calculations of VLE in electrolytes systems using chemical theory: aqueous acis chloridric system. 2nd Mercosur Congress on Chemical Engineering; 4th Mercosur Congress on Process Systems Engineering. 2008.
Cardona, et al. Production of bioethanol from sugarcane bagasse: Status and Bioresource Technology. 2010; 101:4754-4766. perspectives.
Carole, et al. Opportunities in the Industrial Biobased Products Industry. Applied Biochemistry and Biotechnology. 2004; 113-116:871-88.
Carr. The Biobased Revolution: How Biotechnology and Policy Are Changing the Way Materials Are Made. ASC Fall Convention & Expo. Oct. 11, 2005.
Carvalho, et al. Comparison of different procedures for the detoxification of eucalyptus hemicellulosic hydrolysate for use in fermentative processes. J Chem Technol Biotechnol 2006; 81:152-157.
Carvelheiro, et al. Hemicellulose biorefineries: a review on biomass pretreatments. J Sci Ind Res. 2008; 67:849-864.
Cayle, et al. The application of Mathews' Formula in Enzymatic Starch Conversions. Mar. 1966; 43:237-244.
Celunol. EESI Congressional Briefing. Sep. 22, 2006.
Chalov, et al. Continuous hydrolysis of plant tissue polysaccharides with 46-48% hydrochloric acid. III. Absorption of hydrogen chloride by moist wood. Izvestiya Vysshikh Uchebnykh Zavedenii, Lesnoi Zhurnal (1966), 9(6), 139-43. Coden: IVZLAL ISSN: 0536-1036. Abstract only.
Chalov, et al. Continuous hydrolysis of plant tissue polysaccharides with 46-48% hydrochloric acid. IV. The problem of the limit concentration of sugars in the hydrolyzate. Sbornik Trudov, Vsesoyuznyi Nauchno-Issledovatel'skii Institut Gidroliza Rastitel'nykh Materialov (1965), 13 31-8. Coden: SVGSAN ISSN: 0371-4322. Abstract only.
Chalov, et al. Continuous hydrolysis of plant tissues with 46-48% hydrochloric acid. VII. Composition of products of hydrolytic destruction of cellulose by concentrated hydrochloric acid. Zhurnal Prikladnoi Khimii (Sankt-Peterburg, Russian Federation).(1967), 40(4), 929-30. Coden: ZPKHAB ISSN: 0044-4618. Abstract only.
Chalov, et al. Continuous hydrolysis of plant tissues with 46-48% hydrochloric acid. II. Effect of hydrogen chloride on oven-dry wood. Izv. Vysshikh Uchebn. Zavedenii, Lesn. Zh. (1963), 6(2), 141-4. Abstract only.
Chalov, et al. Continuous hydrolysis of wood with 46-48% hydrochloric acid. 1962), 5(No. B), 141-8. Coden: IVZLAL ISSN: 0536-1036. Abstract only.
Chalov, et al. Differential hydrolysis of wood with concentrated hydrochloric acid in diffusion equipment. 1961), 4(6), 138-46. Coden: IVZLAL ISSN: 0536-1036. Abstract only.
Chalov, et al. Equilibrium state in the system cellulose-hydrogen chloride-water-hydrolysis products. USSR. Sb. Tr. Vses. Nauch.-Issled. Inst. Gidroliza Rastit. Mater. (1968), 17 173-9. From: Ref. Zh., Khim 1969, Abstr. No. 15p23. Abstract only.
Chalov, et al. Hydrolysis of difficult-to-hydrolyze polysaccharides of wood with 30-6% hydrochloric acid at 20-40.deg. USSR. Sb. Tr. Vses. Nauch.-Issled. Inst. Gidroliza Rast. Mater. (1969), 18 58-66. From: Ref. Zh., Khim 1970, Abstr. No. 11P29. Abstract only.
Chalov, et al. Hydrolysis of hemicellulose components of pinewood with 30-36% hydrochloric acid. Zhurnal Prikladnoi Khimii (Sankt-Peterburg, Russian Federation) (1961), 34 1601-8. CODEN: ZPKHAB ISSN: 0044-4618. Abstract only.
Chalov, et al. Hydrolysis of hemicellulose components of pinewood with 30-36% hydrochloric acid at 30-40.deg. Gidroliznaya i Lesokhimicheskaya Promyshlennost (1968), 21(3), 4-6. CODEN: GLKPA2 ISSN: 0016-9706. Abstract only.
Chalov, et al. Hydrolysis of lignocellulose with 38-41% hydrochloric acid at 20°. Vysshikh Uchebn. Zavedenii, Lesn. Zh. (1964), 7(2), 137-43. Abstract only.
Chalov, et al. Hydrolysis of pinewood lignocellulose with 41% hydrochloric acid in a [6-] diffuser unit. Izvest. Vysshikh Ucheb. Zavedenii, Lesnoi Zhur. (1961), 4(No. 2), 131-7. Abstract only.
Chalov, et al. Hydrolysis of polysaccharides of pinewood with 38-41% hydrochloric acid at 20°. Zhurnal Strukturnoi Khimii (1962), 35(No. 6), 1347-55. CODEN: ZSTKAI ISSN: 0136-7463. Abstract only.
Chalov, et al. Hydrolysis of polysaccharides of plant fiber in concentrated aqueous and gaseous hydrochloric acid. Zhurnal Prikladnoi Khimii (Sankt-Peterburg, Russian Federation) (1960), 33 2743-50. CODEN: ZPKHAB ISSN: 0044-4618. Abstract only.
Chalov, et al. Hydrolysis of wood with concentrated hydrochloric acid. Gidroliznaya i Lesokhimicheskaya Promyshlennost (1959), 12(No. 4), 1-4. Abstract only.
Chalov, et al. Hydrolysis of wood with concentrated hydrochloric acid. Gidroliz. i Lesokhim Prom. (1959), 12(No. 3), 3-5. Abstract only.
Chalov, et al. Hydrolysis of wood with gaseous hydrochloric acid under atmospheric pressure. Gidroliznaya i Lesokhimicheskaya Promyshlennost (1959), 12 14-18. Abstract only.
Chalov, et al. Two-stage hydrolysis of wood by use of mechanochemical degradation of lignocellulose in the presence of hydrochloric acid. Sbornik Trudov. Gosudarstvennyi Nauchno-issledovatel'skii Institut Gidroliznoi i Sul'fitno-spirtovoi Promyshlennosti (1966), 15 189-98. CODEN: SGSSAC. Abstract only.
Chalov, et al. Withdrawal of the heat of absorption during hydrolysis of wood with gaseous hydrogen chloride. 1962), 5(No. 1), 155-62. CODEN: IVZLAL ISSN: 0536-1036. Abstract only.
Chalov. Sorption of Hydrogen Chloride by moist lignocellulose. SB. TR. VNII Gidroliza Rastitel'n. Mater. 1975; 25:41-49.
Chambost, et al. Guided tour: Implementing the forest biorefinery (FBR) at existing pulp and paper mills. Pulp & Paper Canada. 2008; 109(7):1-9.
Chandra, et al. Substrate Pretreatment: The Key to Effective Enzymatic Hydrolysis of Lignocellulosics? Adv Biochem Engin/Biotechnol. 2007; 108: 67-93.
Chang, et al. Modification of wood with isopropyl glycidyl ether and its effects on decay resistance and light stability. Bioresource Technology. 2006; 97:1265-1271.

(56) References Cited

OTHER PUBLICATIONS

Chaow-U-Thai et al. Removal of ash from sugarcane leaves and tops. International Journal of Biosciences.2012; 2(5): 12-17.
Cheng et al. A novel method to prepare L-arabinose from xylose mother liquor by yeast-mediated biopurification. Microbial cell factories.2011; 10 (43): 1-11.
Chevalier, et al. Vapor-Liquid Equilibrium Data for the Systems H2O—H2SO4—HCl, H2O—H2SO4—HBr, and H2O—HBr at 780 mmHg Pressure. J. Chem. Eng. Data. 1980; 25:271-273.
Chidambaram, et al. A two-step approach for the catalytic conversion of glucose to 2,5-dimethylfuran in ionic liquids. Green Chem. 2010; 12: 1254-1262.
Choudhary et al. Conversion of Xylose to Furfural Using Lewis and Brønsted Acid Catalysts in Aqueous Media. ASC Catalysis.2012; 2: 2022-2028.
Choudhary et al. Highly efficient aqueous oxidation of furfural to succinic acid using reusable heterogeneous acid catalyst with hydrogen peroxide. Chem. Lett. 2012; 41: 409-411.
Claricone Clarifiers and FiltraCone treatment plants. CB&I. Accessed Nov. 30, 2011.
Coetzee, et al. Determination of pectin content of eucalyptus wood. Holzforschung. 2011; 65:327-331.
Cole. XCV. The determination of reducing sugars by titration of ferricyanide. Biochem. 1933 xxvii, pp. 723-726.
Coma, et al. alpha-Glucosidase and N-Acetyl-p-o-glucosaminidase Isoenzymes in Serum. Clin. Chem. 1992; 38(2):223-226.
Conner, et al. Kinetic modeling of hardwood prehydrolysis. Part II. Xylan removal by dilute hydrochloric acid prehydrolysis. Wood and Fiber Science. 1985; 17(4):540-548.
Crittenden, et al. Extraction of hydrogene chloride from agues solutions. Industrial and Engineering Chemistry. Feb. 1954; 46(2):265-274.
Cui. Structural Analysis of Polysaccharides. Chapter 3. Copyright 2005 by Taylor & Francis Group, LLC.
Curtis, et al. Equilibria in furfural-water systems under increased pressure and the influence of added salts upon the mutual solubilities of furfural and water. Aus. J. Sci. Res; 1948; 1(2): 213-235.
David, et al. Cross-Polarization/Magic Angle Spinning (CP/MAS) 13C Nuclear Magnetic Resonance (NMR) Analysis of Chars from Alkaline-Treated Pyrolyzed Softwood. Energy & Fuels. 2009; 23:498-501.
Dayton, et al. Biomass Hydropyrolysis in a Pressurized Fluidized Bed Reactor. Energy and Fuels.2013; 27: 3778-3785.
De Wild, et al. Pyrolysis of Wheat Straw—Derived Organosolv Lignin. Ch. 5, pp. 101-122. 2011.
Demirbas. Furfural Production from Fruit Shells by Acid-Catalyzed Hydrolysis, Energy Sources, Part A: Recovery, Utilization, and Environmental Effects. 2006; 28(2):157-165.
Demirbas. Products from lignocellulosic materials via degradation processes. Energy Sources, Part A. 2008; 30:27-37.
Diaz, et al. Variations in fiber length and some pulp chemical properties of *Leucaena* varieties. Industrial Crops and Products. 2007; 26(2): 142-150.
Dimmel et al. Electron transfer reactions in pulping systems ( II ): electrochemistry of Anthraquinone / Lignin model QUINONEMETHIDES. IPC Thechnical Paper series. 1984; 141: 1-22.
Dimmel et al. Fundamentals of selectivity in pulping and bleaching: Delignification reactions. Progress Report, Institute of paper chemistry. 1986, report 3.
Dimmel et al. IPC Technical Paper Series No. 139 Electron Transfer Reactions in Pulping Systems ( I ): Theory and Applicability to Anthraquinone Pulping. 1984; 139: 1-15.
Dimov, et al. Influence of the amount and concentration of hydrochloric acid on the composition of wheat straw during pre-hydrolysis. Chem. Technol. Inst., Sofia, Bulg. Papier (Paris) (1960), 14 673-6. CODEN: PPERA3 ISSN: 0370-1174. Abstract only.
Dipardo. Outlook for Biomass Ethanol Production and Demand. Energy Information Administration. 2008; 1-14.
Draucker. Novel solvent systems for the development of sustainable technologies. Georgia Institute of Technology. Aug. 2007.
Drenkow. Wood Saccharification. A Modified Rheinau Process. 1976. DouglasDrenkow.com/write2a.html.
Duque. Acid-functionalized nanoparticles for hydrolysis of lignocellulosic feedstocks. Master of Science, Department of Biological and Agricultural Engineering, College of Engineering, Kansas State University, Manhattan, Kansas. 2009.
Dutta et al. Direct conversion of cellulose and lignocellulosic biomass into chemicals and biofuel with metal chloride catalysts. Journal of Catalysis; 2012; 288; 8-15.
Dyadic. AlternaFuel® 200P, Product #326, (for considerations in biomass saccharification applications). 2010.
Dyadic. Enzyme Development for Fuel Ethanol Production from Pre-treated Biomass, Technical Report May 2010, Saccharification I.D: Sacc 05.17.10.
Eggeman, et al. Process and economic analysis of pretreatment technologies. Bio. Tech. 2005; 96:2019-2025.
Ehara, et al. A comparative study on chemical conversion of cellulose between the batch type and flow type systems in supercritical water. Cellulose. 2002; 9:301-311.
Elliott, et al. Pretreatment technologies for advancing anaerobic digestion of pulp and paper biotreatment residues. Water Research. 2007; 41:4273-4286.
Eminov et al. Highly selective and near-quantitative conversion of fructose to 5-hydroxymethylfurfural using mildly acidic ionic liquids. ACS Sustainable Chemistry & Engineering; 2014; 1-17.
Esteves, et al. Chemistry and ecotoxicity of heat-treated pine wood extractives. Wood Sci Technol. Jul. 11, 2010. DOI 10.1007/s00226-010-0356-0.
European office action dated Jul. 31, 2012 for EP Application No. 09787553.8.
European search report and opinion dated Dec. 11, 2013 for EP Application No. 11822761.
Excoffier, et al. Saccharification of Steam-Exploded Poplar Wood. Biotechnology and bioengineering. Dec. 20, 1991; 38(11):1308-1317.
Eyal, et al. Extraction of Metal Salts by Mixtures of Water-Immiscible Amines and Organic Acids (Acid-Base Couple Extractants). 1. A Review of Distribution and Spectroscopic Data and of Proposed Extraction Mechanisms. Ind. Eng. Chem. Res. 1994; 33:1067-1075.
Eyal, et al. pH dependence of carboxylicand mineral acid extraction by amine-based extractants: effects of pKa, Amine Basicity, and diluent properties. Ind. Eng. Chem. Res. 1995; 34:1789-1798.
Farrell, et al. Solving Pitch Problems in Pulp and Paper Processes by the Use of Enzymes or Fungi. Advances in Biochemical Engineering/Biochemical Engineering/1997/pp. 198-212.
Fenner, et al. Examination of the Thermal Decomposition of Kraft Pine Lignin by Fourier Transform Infrared Evolved Gas Analysis. J. Agric. Food Chem. 1981; 29:846-849.
Ferraz, et al. Estimating the chemical composition of biodegraded pine and eucalyptus wood by DRIFT spectroscopy and multivariate analysis. Bioresource Technology. 2000; 74:201-212.
Fierro, et al. Methodical study of the chemical activation of Kraft lignin with KOH and NaOH. Microporous and Mesoporous Materials. 2007; 101:419-431.
Foran, et al. Beyond 2025: Transitions to the biomass-alcohol economy using ethanol and methanol. Working Paper Series 99/07. Dec. 1999.
Foxit. Chemicals partition in wood. Mar. 2011.
Froass, et al. Nuclear Magnetic Resonance Studies. 4. Analysis of Residual Lignin after Kraft Pulping. Ind. Eng. Chem. Res. 1998; 37:3388-3394.
Fungsin, et al. Conversion of cassava waste into sugar using Aspergillus niger and Trichoderma reesei for ethanol production. 2010.
Galbe, et al. A review of the production of ethanol from softwood. Appl Microbiol Biotechnol. 2002; 59:618-628.
Galbe, et al. Process Engineering Economics of Bioethanol Production. Adv Biochem Engin/Biotechnol. 2007; 108:303-327.

(56) References Cited

OTHER PUBLICATIONS

Galego, et al. Mechanism of the thermal resinification of pure furfural . Revista Cenic, Ciencias Fisicas. 1975; 6(1):163-180. Abstract only.

Gamez et al. Study of the hydrolysis of sugar cane bagasse using phosphoric acid. Journal of Food Engineering.2006; 74: 78-88.

Gani et al. Molecular Design of Solvents for Liquid Extraction Based on UNIFAC. Fluid Phase Equilibria. 1983; 13: 331-340.

Garna, et al. Kinetic of the hydrolysis of pectin galacturonic acid chains and quantification by ionic chromatography. Food Chemistry. 2006; 96:477-484.

Genencor. Enzyme Products for Fuel Ethanol Production. Genencor, 2007 Danisco US Inc.

Georgieva, et al. Enzymatic hydrolysis and ethanol fermentation of high dry matter wet-exploded wheat straw at low enzyme loading. Applied biochemistry and biotechnology. 2008;148:35-44.

Georgopoulos, et al. Thermoplastic polymers reinforced with fibrous agricultural residues. 2009.

Gibbs et al. An Economic Value Chain Using Nonfood Biomass Intermediates for Bioplastics Production. Presentation; General Biomass Company; 2013.

Glazkova, et al. Effect of temperature on the extraction of prehydrolysis products from lignocellulose chips. Gidroliznaya i Lesokhimicheskaya Promyshlennost (1974),(6), 12-13. CODEN: GLKPA2 ISSN: 0016-9706. Abstract only.

Goldstein, et al. The hydrolysis of cellulose with superconcentrated hydrochloric acid. Biotechnology and Bioengineering Symposium (1984), Volume Date 1983, 13(Symp. Biotechnol. Fuels Chem., 5th, 1983), 17-25. CODEN: BIBSBR ISSN: 0572-6565. Abstract only.

Goldstein. Potential for Converting Wood into Plastics, Chemicals from wood may regain importance as the cost of petroleum continues to rise. Science, Sep. 12, 1975; 189(4206):847-852.

Goncalves, et al. Hydroxymethylation and oxidation of Organosolv lignins and utilization of the products. Bioresource Technology. 2001; 79:103-111.

Gonzalez-Serrano, et al. Development of Porosity upon Chemical Activation of Kraft Lignin with ZnCl2. Ind. Eng. Chem. Res. 1997; 36:4832-4838.

Gonzalez-Serrano, et al. Removal of water pollutants with activated carbons prepared from H3PO4 activation of lignin from kraft black liquors. Water Research. 2004; 38:3043-3050.

Goto, et al. Supercritical Thermal Decomposition of Cellulose: Experiments and Modeling. Ind. Eng. Chem. Res. 1990; 29:1091-1095.

Grant, et al. Tall oil production and processing. Grant and Hockh's Chemical Dictionary 5th ed. 1987.

Gray, et al. Sugar Monomer and Oligomer Solubility, Data and Predictions for Application to Biomass Hydrolysis. Applied Biochemistry and Biotechnology. 2003; 105-108:179-193.

Grethlein, et al. The Cost of Ethanol Production from Lignocellulosic Biomass—A Comparison of Selected Alternative Processes. USDA. Specific Cooperative Agreement No. 58-1935-2-050. Apr. 30, 1993.

Gretland, et al. Characterisation of lignosulphonates and sulphonated kraft lignin by hydrophobic interaction chromatography. 2005.

Griffith, et al. Low cost carbon fiber for transportation application. USDE. 2003.

Gutierrez, et al. Analysis of Lipophilic extractives from wood and pitch deposits by solid-phase extraction and gas chromatography. J. of Chromatography A. 1998; 823:449-455.

Gutierrez, et al. Enzymatic Removal of Free and Conjugated Sterols Forming Pitch Deposits in Environmentally Sound Bleaching of Eucalypt Paper Pulp. Environ. Sci. Technol. 2006; 40:3416-3422.

Gutierrez, et al. Fungal Degradation of Lipophilic Extractives in Eucalyptus globulus Wood. Applied and environmental microbiology. Apr. 1999; 65(4):1367-1371.

Gutierrez, et al. Microbial and enzymatic control of pitch in the pulp and paper industry. Appl Microbiol Biotechnol. 2009; 82:1005-1018.

Gutierrez, et al. The biotechnological control of pitch in paper pulp manufacturing. TRENDS in Biotechnology. 2001; 19(9):340-348.

Haensel, et al. Pyrolysis of wood-based polymer compounds. J. Anal. Appl. Pyrolysis. 2010; 87:124-128.

Hage, et al. Effects of process severity on the chemical structure of Miscanthus ethanol organosolv lignin. Polymer Degradation and Stability. 2010; 95:997-1003.

Hagglund. Report of the research activities of the Cellulose Laboratory (Stockholm, Sweden) during the year 1941. Svensk Papperstidning (1942), 45 123-35. Abstract only.

Hagglund. The Decomposition of Wood by Acids wood Saccharification. Chemistry of Wood. New York: Academic Press, 1951. 631. Chapter IV. 390-413.

Hagglund. Wood Saccharification. A Modified Rheinau Process. 2011.

Hall, et al. Wood saccharification. USDA. Unasylva. 2007; 10(1).

Hall. Polyhydric alcohol from wood. US Department of Agriculture, Forest Service, Forest Products Laboratory , Madison, Wisconsin. No. 1984. Jul. 1954.

Hallac, et al. Biomass Characterization and Organosolv Pretreatment of Buddleja davidii. School of Chemistry and Biochemistry, Institute of Paper Science and Technology, Georgia Institute of Technology, Atlanta, GA. 2009.

Hallac, et al. Biomass Characterization of Buddleja davidii: A Potential Feedstock for Biofuel Production. J. Agric. Food Chem. 2009; 57(4):1275-1281.

Hallac, et al. Chemical Transformations of Buddleja davidii Lignin during Ethanol Organosolv Pretreatment. Energy Fuels. 2010; 24:2723-2732.

Hallac. Fundamental understanding of the biochemical conversion of buddleja davidii to fermentable sugars. Georgia Institute of Technology. May 2011.

Hallal et al. Electrochemical polymerization of furfural on a platinum electrode in aqueous solutions of potassium biphthalate. Materials Research; 2005; 8(1); 23-29.

Hamelinck et al. Ethanol from lignocellulosic biomass: techno-economic performance in short-, middle- and long-term. Biomass and Bioenergy; 2005; 28; 384-410.

Hamelinck, et al. Production of advanced biofuels. International Sugar Journal. 2006; 108(1287):168-175.

Han, et al. Optimizing lignocellulosic feedstock for improved biofuel productivity and processing. Biofuels, Bioprod. Bioref 2007; 1:135-146.

Harada, et al. Formation of Isoamylase by Pseudomonas. Applied Microbiology. Oct. 1968; 16(10):1439-1444.

Harris, et al. Hydrolysis of wood cellulose with hydrochloric acid and sulfur dioxide and the decomposition of its hydrolytic products. Journal of Physical and Colloid Chemistry. (1949), 53:344-51. Abstract only.

Harris, et al. The Madison Wood-Sugar Process. US Dept. of Agriculture. Jun. 1946; 1-21.

Harris. Derived products and chemical utilization of wood waste. Forest Products Laboratory; Forest Service US Department of Agriculture; Rept. No. R1666-10. Jun. 1949.

Hasegawa, et al. New Pretreatment Methods Combining a Hot Water Treatment and Water/Acetone Extraction for Thermo-Chemical Conversion of Biomass. Energy & Fuels. 2004; 18:755-760.

Hatcher. Dipolar-Dephasing $^{13}$C NMR Studies of Decomposed Wood and Coalified Xylem Tissue:Evidence for Chemical Structural Changes Associated with Defunctionalization of Lignin Structural Units during Coalification. Energy. Fuels. 1988; 2:48-58.

Havlik, et al. Atmospheric leaching of EAF dust with diluted sulphuric acid. Hydrometallurgy. 2004; doi:10.1016/j.hydromet. 2004.10.008.

Hawley, et al. Comparison of hydrogen fluoride saccharification of lignocellulosic materials with other saccarification technologies. Energy in Agriculture. 1983; 2:219-244.

Hayes, et al. The Biofine Process: Production of Levulinic Acid, Furfural and Formic Acid from Lignocellulosic Feedstocks. Biorefinery (8b). 2011.

(56) References Cited

OTHER PUBLICATIONS

Held. Catalytic conversion of renewable plant sugars to fungible liquid hydrocarbon fuels using the bioforming process. TAPPI IBBC session 3. Virent Energy systems. Oct. 15, 2009.

Hendriks, et al. Pretreatments to enhance the digestibility of lignocellulosic biomass. Bioresource Technology. 2009; 100:10-18.

Heppolette, et al. Effect of a-methylation on the parameters characterizing hydrolysis in water for a series of halides and sulfonates. Canadian Journal of Chemistry. 1966; 44:677-684.

Herrera, et al. Effect of the hydrochloric acid concentration on the hydrolysis of sorghum straw at atmospheric pressure. Journal of Food Engineering.2004; 63:103-109.

Herrera, et al. Production of Xylose from Sorghum Straw Using Hydrochloric Acid. Journal of Cereal Science. 2003; 37:267-274.

Herty. Advanced Materials Development Center. HCl Clean Tech Composite Sample—Extracted Wood Sample. 2010.

Hettenhaus et al. Cellulase Assessment Report and Recommendations for Future Work. Ethanol Production from Biomass Hydrolysis; NREL report; 1997.

Heuts, et al. Chrysosporium lucknowense cellulase production platform for applications in biorefineries. DYADIC® Netherlands. 2010.

Higgins, et al. Hydrolysis of cellulose using HCL: A comparison between liquid phase and gaseous phase processes. Agricultural wastes. 1982; 4:97-116.

Hinz, et al. Hemicellulase production in Chrysosporium lucknowense C1. Journal of Cereal Science. 2009; 50(3):318-323. doi:10.1016/j.jcs.2009.07.005.

Hirst, et al. CCCLXXXII.—The action of highly concentrated hydrochloric acid on cellulose and on some derivatives of glucose and of xylose. 1923; 3226-3235.

Hoareau et al. Sugar cane bagasse and curaua lignins oxidized by chlorine dioxide and reacted with furfuryl alcohol : characterization and stability. Polymer Degradation and Stability. 2004; 86: 567-576.

Hodge. Chemistry of Browning Reactions in Model Systems. Agricultural and Food Chemistry. Oct. 14, 1953; 1(15):928-943.

Holladay, et al. Top Value-Added Chemicals from Biomass vol. II Results of Screening for Potential Candidates from Biorefinery Lignin. Pacific Northwest National Laboratory, Prepared for the U.S. Department of Energy. Oct. 2007.

Holm, et al. Ionic Liquids in the Pretreatment of Lignocellulosic Biomass. chapter 24, 545-560. 2011.

Holota, et al. One-stage hydrolysis of beechwood sawdust by gaseous hydrogen chloride. Vyskum (1967), (2), 105-18. CODEN: DRVYAP ISSN: 0012-6136. Abstract only.

Hou-Rui, et al. Novel Isolates for Biological Detoxification of Lignocellulosic Hydrolysate. Appl Biochem Biotechnol 2009; 152:199-212.

Howarth, et al. Methane and the greenhouse-gas footprint of natural gas from shale formations, A letter. Climatic Change, Accepted: Mar. 13, 2011, DOI 10.1007/s10584-011-0061-5.

Hu, et al. Chemical profiles of switchgrass. Bioresource Technology. 2010; 101:3253-3257.

Huang, et al. A review of separation technologies in current and future biorefineries. Separation and Purification Technology. 2008; 62:1-21.

Huber, et al. Synthesis of Transportation Fuels from Biomass: Chemistry, Catalysts, and Engineering. Chemical Reviews. Published on Web Jun. 27, 2006 Page Est: 54.3, 10.1021/cr068360d.

Huber. Breaking the Chemical and Engineering Barriers to Lignocellulosic Biofuels: Next Generation. Based on the: Jun. 25-26, 2007 ,Workshop, Washington D.C.

Hyttinen, et al. Comparison of VOC emissions between air-dried and heat-treated Norway spruce (*Picea abies*), Scots pine (*Pinus sylvesteris*) and European aspen (*Populus tremula*) wood. Atmospheric Environment. 2010; 44:5028-5033.

Ibarra, et al. Isolation of high-purity residual lignins from eucalypt paper pulps by cellulase and proteinase treatments followed by solvent extraction. Enzyme and Microbial Technology. 2004; 35:173-181.

Ibrahim, et al. Comparison of alkaline pulping with steam explosion for glucose production from rice straw. Carbohydrate Polymers. 2011; 83:720-726.

IntechFibres. Microscopic Analysis of pulps, papers and boards: for a Fundamental Knowledge of Fibre Structure. IntechFibers, research in fibers Nov. 2007.

International search report and written opinion dated Feb. 4, 2010 for PCT/IL2009/000843.

International search report and written opinion dated Feb. 10, 2012 for PCT/US2011/050435.

International search report and written opinion dated Mar. 26, 2013 for PCT/US2013/021055.

International search report and written opinion dated May 20, 2010 for PCT/IL2009/001091.

International search report and written opinion dated Jul. 4, 2008 for PCT/IL2008/000278.

International search report and written opinion dated Sep. 8, 2010 for PCT/IL2009/000782.

International search report and written opinion dated Sep. 14, 2010 for PCT/IL2010/000317.

International search report and written opinion dated Sep. 23, 2011 for PCT/IL2011/000304.

International search report and written opinion dated Dec. 10, 2009 for PCT/IL2009/000392.

International search report and written opinion dated Dec. 20, 2011 for PCT/US2011/046153.

International search report dated Apr. 26, 2011 for PCT/IL2011/000130.

International search report dated May 5, 2011 for PCT/IL2010/001042.

International search report dated Jun. 6, 2011 for PCT/IL2011/000131.

International search report dated Aug. 10, 2011 for PCT/IL2010/000786.

International search report dated Nov. 14, 2011 for PCT/IL2011/000424.

Iranmahboob, et al. Optimizing acid-hydrolysis: a critical step for production of ethanol from mixed wood chips. Biomass and Bioenergy. 2002; 22:401-404.

IsoClear 42% high fructose 80% solids corn syrup. Technical product information. Cargill. Updated Aug. 14, 2012.

Itzkowitz. Biodiesel from sugars. 2011.

Izydorczyk, et al. Polysaccharide Gums: Structures, Functional Properties, and Applications. Chapter 6. Copyright 2005 by Taylor & Francis Group, LLC.

Izydorczyk. Understanding the Chemistry of Food Carbohydrates. Chapter 1. Copyright 2005 by Taylor & Francis Group, LLC.

Jacobsen et al. Xylose Monomer and Oligomer Yields for Uncatalyzed Hydrolysis of Sugarcane Bagasse Hemicellulose at Varying Solids Concentration. Industrial & Engineering Chemistry Research; 2002; 41; 1454-1461.

Jacobsen, et al. Cellulose and Hemicellulose Hydrolysis Models for Application to Current and Novel Pretreatment Processes. Applied Biochemistry and Bio. 2000; 84-86:81-96.

Jiang, et al. Perdeuterated pyridinium molten salt (ionic liquid) for direct dissolution and NMR analysis of plant cell walls. Green Chem. 2009; 11:1762-1766.

Johannis. Rhenium- and molybdenum-catalyzed Dehydration Reactions. PhD Thesis. Utrecht University, The Netherlands, 1984.

Johnson. Effects of Dilute Acid Hydrolyzate Components on Glucose Degradation. National Bioenergy Center, NREL, 1617 Cole Blvd., Golden, Colorado 80401, USA. 2011.

Kadam, et al. Generating Process and Economic Data Needed for Preliminary Design of PureVision Biorefineries. DOE Project No. DE-FG36-05GO85004, Final Nonproprietary Technical Report. Dec. 28, 2007.

Kaewwongsa, et al. Intestinal digestibility of the residual components of cassava pulp solid state fermentation by saccharomyces cerevisiae. Suranaree J. Sci. Technol. 2009; 16(4):291-296.

Kamm et al. Internationale Biorafﬁnerie-Systeme Internationale Biorafﬁnerie-Systeme. Presentation; Brandenburgische Technische Universitat Cottbus; Frankfurt; 2006.

(56) References Cited

OTHER PUBLICATIONS

Kamm, et al. Chemical and biochemical generation of carbohydrates from lignocellulose-feedstock (*Lupinus nootkatensis*)—quantification of glucose. Chemosphere. 2006; 62:97-105.
Kamm, et al. Definition and technical status of Biorefineries. BioreFuture 2008, Tuesday Feb. 12, 2008, Brussels.
Karinen et al. Biorefining: heterogeneously catalyzed reactions of carbohydrates for the production of furfural and hydroxymethylfurfural. ChemSusChem; 2011; 4; 1002-1016.
Katzen, et al. A View of the History of Biochemical Engineering. Advances in Biochemical Engineering/Biotechnology. 2000; 70:77-91.
Kauko. Similarity of the action of hydrochloric acid upon cellulose and humus. Ann. acad. sci. Fennicae (1927), 26A(No. 15), 3-7. Abstract only.
Kauper. Sulfur-free lignin from alkaline pulping as emulsifiers. The international Lignin Institute, 5th international Forum' Sep. 7, 2000, Bordeaux (France).
Keller, et al. Microbial Pretreatment of Biomass, Potential for Reducing Severity. Applied Biochemistry and Biotechnology. 2003; 105-108:27-41.
Khan, et al. Kinetic Study on Palm Oil Waste Decomposition. Biofuel's Engineering Process Technology. 2011. Chapter 22, pp. 523-536.
Khan, et al. Protobind 1075—An Indigenous Economical and Eco-friendly Renewable Raw Material for the Plywood Industry. 2011.
Kim, et al. Continuous Countercurrent Extraction of Hemicellulose from Pretreated Wood Residues. Applied Biochemistry and Biotechnology. 2001; 91-93:253-267.
Kim, et al. Enzyme hydrolysis and ethanol fermentaion of liquid hot water and AFEX pretreated distillers' grains at high-solid loadings. Bio. Tech. 2008; 99:5206-5215.
Kim, et al. Pretreatment and fractionation of corn stover by ammonia recycle percolation process. Bioresource Technology. 2005; 96:2007-2013.
Kim, et al. Pretreatment of Corn Stover by Low-Liquid Ammonia Recycle Percolation Process. Applied Biochemistry and Biotechnology. 2006; 133:41-57.
Kim, et al. Supercritical CO2 pretreatment of lignocellulose enhances enzymatic cellulose hydrolysis. Bioresource Technology. 2001; 77:139-144.
Kimberley, et al. A colorimetric method for the quantitation of galacturonic acid. Applied biochemistry and biotechnology. 1993; 43:51-54.
Kinders, et al. Saccharification of HCl-treated substrate provided by HCL-Cleantech, Technical Report, Mar. 2010. Dyadic International Inc. // Confidential and Proprietary Information.
Kindsigo et al. Degradation of lignins by wet oxidation : model water solutions. Proc. Estonian Acad. Sci. Chem.; 2006; 55(3); 132-144.
Kintner III, et al. Carbohydrate Interference and Its Correction in Pectin Analysis Using the m-Hydroxydiphenyl Method. Journal of Food Science. 1982; 47:756-759.
Kjellstrand, et al. Development of toxic degradation products during heat sterilization of glucose-containing fluids for peritoneal dialysis: influence of time and temperature. Pent Dial Int. 1995;15(1):26-32.
Konn et al. Chemical Reactions in Chemimechanical Pulping : Material Balances of Wood Components in a CTMP Process. Journal of pulp and paper science; 2002; 28; 395-399.
Korotkov, et al. Continuous hydrolysis of plant tissues with 46-48 hydrochloric acid. VI. The effect of heat on wood saturated with gaseous hydrogen chloride, with simultaneous increase of the partial pressure of hydrogen chloride. Sbornik Trudov, Vsesoyuznyi Nauchno-Issledovatel'skii Institut Gidroliza Rastitel'nykh Materialov (1965), 14 180-91. Abstract only.
Koski. Applicability of crude tall oil for wood protection. Acta Univ. Oul. C 293, 2008, Oulun Yliopisto, Oulu 2008.
Kovalev, et al. Reaction of sprucewood pulp with hydrogen chloride dissolved in dichloroethane. Sbornik Trudov Ukrainskogo Nauchno-Issledovatel'skogo Instituta Tsellyulozno-Bumazhnoi Promyshlennosti (1966), No. 9 51-69. CODEN: SUTBAU ISSN: 0453-8560. Abstract only.
Krall, et al. Pectin Hydrolysis: Effect of Temperature , Degree of Methylation, pH, and Calcium on Hydrolysis Rates. J. Agric. Food Chem. 1998; 46:1311-1315.
Kribble, et al. The Electromotive Force Measurements of Hydrochloric Acid Solutions with and without Sucrose and their Relation to the Rate of Sucrose Hydrolysis. Jan. 1935; 57:19-22.
Kubo, et al. Preparation of carbon fibers from softwood lignin by atmospheric acetic acid pulping. Carbon. 1998; 36(7-8):1119-1124.
Kubo, et al. Surface Porosity of Lignin/PP Blend Carbon Fibers. Journal of Wood Chemistry and Technology. 2007; 27: 257-271.
Kubo, et al. Thermal Decomposition Study of Isolated Lignin Using Temperature Modulated TGA. Journal of Wood Chemistry and Technology. 2008; 28(2):106-121.
Kucuk, et al. Biomass Conversion Processes. Energy Conyers. Mgmt. 1997; 38(2):151-165.
Kumar, et al. Effect of Enzyme Supplementation at Moderate Cellulase Loadings on Initial Glucose and Xylose Release From Corn Stover Solids Pretreated by Leading Technologies. Biotechnology and Bioengineering. Feb. 1, 2009; 102(2):457-567.
Kumar, et al. Methods for Pretreatment of Lignocellulosic Biomass for Efficient Hydrolysis and Biofuel Production. Ind. Eng. Chem. Res. 2009; 48:3713-3729.
Kunamneni, et al. Fungal laccase—a versatile enzyme for biotechnological applications. Communicating Current Research and Educational Topics and Trends in Applied Microbiology. 2007; 233-245.
Kusama, et al. Wood saccharification by gaseous hydrogen chloride. Chisso Corp., Tokyo, Kogyo Kagaku Zasshi. 1966. Parts 1-V and VIII. Abstracts only.
Laine. Structures of hemicelluloses and pectins in wood and pulp. degree of Doctor of Science, Helsinki University of Technology,Department of Chemical Technology, Laboratory of Organic Chemistry, Espoo, Finland, 2005.
Lam, et al. Kinetic Modeling of Pseudolignin Formation in Steam Exploded Woody Biomass. 2011.
Lam. Steam explosion of biomass to produce durable wood pellets. The University of British Columbia (Vancouver). May 2011.
Lange, et al. Lignocellulose conversion: an introduction to chemistry, process and economics. Biofuels, Bioprod. Bioref. 2007; 1:39-48.
Lapan, et al. Hydrochloric and sulfuric acid hydrolyzates of fir wood. Izvestiya Nauchno-Issledovatel'skogo Instituta Nefte-i Uglekhimicheskogo Sinteza pri Irkutskom Universitete (1970), 12 102-4. CODEN: INEUBO ISSN: 0367-9195. Abstract only.
Lavarack, et al. The acid hydrolysis of sugarcane bagasse hemicellulose to produce xylose, arabinose, glucose and other products. Biomass and Bioenergy. 2002; 23:367-380.
Lebedev, et al. Hydrolysis of cellulose with concentrated hydrochloric acid at different temperatures. Sb. Tr., Gos. Nauchn.-Issled. Inst. Gidrolizn. i Sul'fitno-Spirt. Prom. (1961), 9 7-19. Abstract only.
Lebedev, et al. Hydrolysis of wood with concentrated hydrochloric acid solutions at different temperatures. Sb. Tr., Gos. Nauchn.-Issled. Inst. Gidrolizn. i Sul'fitno-Spirt. Prom. (1961), 9 20-35. Abstract only.
Lee, et al. Dilute-Acid Hydrolysis of Lignocellulosic Biomass. Advances in Biochemical Engineering/ Biotechnology. 1999; 65:93-115.
Lee, et al. Ionic Liquid-Mediated Selective Extraction of Lignin From Wood Leading to Enhanced Enzymatic Cellulose Hydrolysis. Biotechnology and Bioengineering. Apr. 1, 2009; 102(5):1368-1376.
Leonard, et al. Fermentation of wood sugars to ethyl alcohol. US Department of Agriculture, Forest Service, Forest Products Laboratory, Madison, Wisconsin. No. R1466. Dec. 1944.
Leschinsky, et al. Detailed Mass Balance of the Autohydrolysis of Eucalyptus Globulus at 170C. BioResources. 2009; 4(2): 687-703.
Leshchuk, et al. Continuous hydrolysis of plant tissue with 45-48% hydrochloric acid. V. Equilibrium in the system polysaccharides-hydrolysis products-hydrochloric acid. Gidrolizn. i Lesokhim Prom. (1965), 18(5), 10-13. Abstract only.

(56) References Cited

OTHER PUBLICATIONS

Leshchuk, et al. Intensification of differential hydrolysis of softwood with concentrated hydrochloric acid in a diffusion apparatus. USSR. Sb. Tr. Vses. Nauch.-Issled. Inst. Gidroliza Rast Mater. (1968), 17 16-73. From: Ref. Zh., Khim 1969, Abstr. No. 17P20. Abstract only.

Leshchuk, et al. Penetration of concentrated hydrochloric acid into the pores of wood particles and the formation of hydrolyzates within the particles. Sbornik Trudov. Gosudarstvennyi Nauchno-issledovatel'skii Institut Gidroliznoi i Sul'fitno-spirtovoi Promyshlennosti (1966), 15 156-67. CODEN: SGSSAC. Abstract only.

Lewkowski et al. Synthesis, chemistry and applications of 5-hydroxymethylfurfural and its derivatives. Arkivoc; 2001; I; 17-54.

Li, et al. Acidolysis of Wood in Ionic Liquids. Ind. Eng. Chem. Res. 2010; 49(7):3126-3136.

Li, et al. Efficient Acid-Catalyzed Hydrolysis of Cellulose in Ionic Liquid. Advanced Synthesis & Catalysis; 2007; 349; 1847-1850.

Li, et al. Ethanol Organosolv Lignin-based Rigid Polyurethane Foam Reinforced with Cellulose Nanowhiskers. Institute of Paper Science and Technology. 2011.

Li, et al. Interaction of Supercritical Fluids with Lignocellulosic Materials. Ind. Eng. Chem. Res. 1988; 27:1301-1312.

Li, et al. Kraft Lignin-based Rigid Polyurethane Foam. Institute of Paper Science and Technology. 2011.

Li, et al. Lignin depolymerization/repolymerization and its critical role for delignification of aspen wood by steam explosion. Bioresource Technology 98 (2007) 3061-3068.

Li, et al. Steam explosion lignins; their extraction, structure and potential as feedstock for biodiesel and chemicals. Bioresource Technology. 2009.

Lin et al. Liquid phase reforming of rice straw for furfural production. International Journal of Hydrogen Energy; 2013; 4-10.

Lin, et al. Ethanol fermentation from biomass resources: current state and prospects. Appl Microbiol Biotechnol. 2006; 69:627-642.

Liu et al. Effects of lignin-metal complexation on enzymatic hydrolysis of cellulose. Journal of agricultural and food chemistry. 2010; 58(12): 7233-7238.

Liu, et al. Citrus Pectin: Characterization and Inhibitory Effect on Fibroblast Growth Factor-Receptor Interaction. J. Agric. Food Chem. 2001; 49:3051-3057.

Liu, et al. Effects of Lignin-Metal Complexation on Enzymatic Hydrolysis of Cellulose. J. Agric. Food Chem. 2010; 58:7233-7238.

Liu, et al. Partial flow of compressed-hot water through corn stover to enhance hemicellulose sugar recovery and enzymatic digestibility of cellulose. Bioresource Technology. 2005; 96:1978-1985.

Liu. Understanding Starches and Their Role in Foods. Chapter 7. Copyright 2005 by Taylor & Francis Group, LLC.

Locke. Chemical Conversion Products from wood. USDA. Aug. 1960.

Long, et al. Application of the Ho Acidity Function to kinetics and Mechanisms of acid Catalysis. Mar. 30, 1957; 935-1010.

Lora. GreenValue-Technologies and Products. GreenValueEnterprises LLC, Media, PA, USA. 2011.

Lora. Non-Wood Biorefinery Developments Outside North America. 2011.

Lora., et al. Autohydrolysis sf aspen milled wood lignin. AYMANC. An. J. Chem. 1980; 58:669-676.

Lynd, et al. Strategic Biorefinery Analysis: Analysis of Biorefineries, Jan. 24, 2002-Jul. 1, 2002. Subcontract Report, NREL/SR-510-35578, Jan. 10, 2005.

Ma, et al. Conversion of fructose to 5-hydroxymethylfurfural with a functionalized ionic liquid. BioResources; 2011; 7; 533-544.

Mabee, et al. Updates on Softwood-to-Ethanol Process Development. Applied Biochemistry and Biotechnology, 2006;129-132:55-70.

Mai, et al. Biotechnology in the wood industry. Appl Microbiol Biotechnol; 2004; 63:477-494.

Manninen, et al. Comparing the VOC emissions between air-dried and heat-treated Scots pine wood. Atmospheric Environment. 2002; 36:1763-1768.

Marchal, et al. Conversion into acetone and butanol of lignocellulosic substrates pretreated by steam explosion. Biotechnology Letters. 1986; 8(5):365-370.

Marchal, et al. Large-Scale Enzymatic Hydrolysis of Agricultural Lignocellulosic Biomass. Part 2: Conversion into Acetone-Butanol. Bioresource Technology. 1992; 42:205-217.

Marcotullio et al. Bioenergy II : Furfural Destruction Kinetics during Sulphuric Acid-Catalyzed Production from Biomass Bioenergy II : Furfural Destruction Kinetics during Sulphuric Acid-Catalyzed Production from Biomass. International journal of Chemical Reactor Engineering; 2009; 7; Article A67.

Marcotullio et al. Furfural production in modern lignocellulose-feedstock biorefineries. Presentation; Delft University of Technology; St. Petersburg; 2013.

Marcotullio. The chemistry and technology of furfural production in modern Lignicellulose-feedstock biorefineries. PhD thesis. 2011; Delft University, Italy.

Marker, et al. Optical properties of glucose. 2009.

Marone, et al. Effect of particle sizes on the kinetics of drying of a hydrochloric acid hydrolysate mass. Gidroliznaya i Lesokhimicheskaya Promyshlennost (1976), (3), 15. CODEN: GLKPA2 Issn: 0016-9706. Abstract only.

Marsh et al. Possible Uses of Corncob Cellulose in the Explosives Industry. The journal of Industrial and Engineering Chemistry; 1921; 13(4); 296-298.

Martin, et al. Engineering a mevalonate pathway in *Escherichia coli* for production of terpenoids. Nature Biotechnology. 2003; 21(7):796-802.

Martinez-Inigo, et al. Time course of fungal removal of lipophilic extractives from Eucalyptus globulus wood. Journal of Biotechnology. 2000; 84:119-126.

Martin-Sampedro, et al. Combination of steam explosion and laccase-mediator treatments prior to Eucalyptus globulus kraft pulping. Bioresource Technology 2011; 102:7183-7189.

Mascal et al. Towards the efficient, total glycan utilization of biomass. ChemSusChem; 2009; 2(5); 423-426.

Mascal, et al. Direct, High Yield Conversion of Cellulose into Biofuel. Angew. Chem. Int. Ed. 2008; 7:7924-7926.

Mascal, et al. High-Yield Chemical Conversion of Biomass into Biofuels and Value added Products. Clean Technology 2010, www.ct-si.org, ISBN 978-1-4398-3419-0. 124-127.

Mascal, et al. Towards the Efficient, Total Glycan Utilization of Biomass. ChemSusChem. 2009; 2:423-426.

Masura. A mathematical model for neutral sulfite pulping of various broadleaved wood species. Wood Science and Technology. 1998; 32:1-13.

McAloon, et al. Determining the Cost of Producing Ethanol from Corn Starch and Lignocellulosic Feedstocks. National Renewable Energy Laboratory, Contract No. DE-AC36-99-GO10337, NREL/TP-580-28893. Prepared under Task No. BFP1.7110. Oct. 2000.

McFeeters, et al. Measurement of Pectin Methylation in Plant Cell Walls. Analytical biochemistry. 1984; 139:212-2 17.

McKenzie, et al. Levulinic acid. Organic Syntheses, Coll. vol. 1, p. 335 (1941); vol. 9, p. 50 (1929). Apr. 29, 2010.

McMillan. Processes for Pretreating Lignocellulosic Biomass: A Review. NatioRnenaewlable Energy Laboratory, A Division of Midwest Research Institute, Operated for the U.S. Department of Energy , Under Contract No. DE-AC02-83CH 10093. Nov. 1992.

Meindersma et al. Production of discrete oxygenated target chemicals from pyrolysis oil. A Report by Eindhoven University of Technology. Netherlands. Jun. 2009.

Membralox ceramic membrane products. Pall corporation. 2004; 1-12.

Menchikov, et al. An Effective Method for Alcohol Preparation by Hydrolysis of Organohalides in the Presence of Copper and its Salts in Aqueous DMSO. Mendeleev Commun. 1995; 5(6): 223-224.

Mendes, et al. Extraction of hemicelluloses prior to kraft cooking: a step for an integrated biorefinery in the pulp mill. XXI Tecnicelpa Conference and Exhibition/VI CIADICYP 2010. Oct. 12-15, 2010.

(56) References Cited

OTHER PUBLICATIONS

Mesfun et al. Integration of hot water extraction in biomass based CHP plants. Master's Thesis. 2010; Lulea University of Technology.
Mesfun. Integration of hot water extraction in biomass based CHP plants-possibilities for green-chemicals and increased electricity production. Integration of hot water extraction in biomass based CHP plants-possibilities for green-chemicals and increased electricity production. 2010.
Mielenz. Ethanol production from biomass: technology and commercialization status. Current Opinion in Microbiology. 2001; 4:324-329.
Mikkola, et al. Hydrolytic decomposition of glycosides in aqueous acids. ARKIVOC 2009 (iii) 39-53.
Miljkovic. Carbohydrates, Synthesis, Mechanisms, and Stereoelectronic Effects. Springer Science+Business Media, LLC 2009.
Miller. Characteristics and Availability of Commercially Important Woods, Chapter 1. Forest Products Laboratory. 1999. Wood handbook—Wood as an engineering material.
Miller. Structure of Wood. Chapter 2. 2009.
Miller. Utilization of wood under Germany's four year plan. Forests Products Division, Bureau of Foreign and Domestic Commerce U.S. Department of Commerce, Washington. 2009; 495-503.
Minima, et al. Hydrolysis of various types of cellulosic raw materials with highly concentrated hydrochloric acid. I. Effect of time, temperature, and acid ratio on the yield of sugars. USSR. Strukt. Modif. Khlop. Tsellyul. (1966), No. 3 315-24. From: Ref. Zh., Khim. 1969, Abstr. No. 1P31. Abstract only.
Miyazawa, et al. Polysaccharide Hydrolysis Accelerated by Adding Carbon Dioxide under Hydrothermal Conditions. Biotechnol. Prog. 2005; 21:1782-1785.
Moelwyn-Hughes. The kinetics of the hydrolysis of certain glucosides, part 11: trehalose, umethylglucoside and tetramethyl-a-amethyglucoside. Nov. 23, 1928; 81-92.
Mohan, et al. Pyrolysis of Wood/Biomass for Bio-oil: A Critical Review. Energy & Fuels; 2006; 20; 848-889.
Mooney, et al. The effect of initial pore volume and lignin content on the enzymatic hydrolysis of softwoods. Bioresource Technology. 1998; 64:113-119.
Moreschi, et al. Hydrolysis of Ginger Bagasse Starch in Subcritical Water and Carbon Dioxide. J. Agric. Food Chem. 2004; 52, 1753-1758.
Mosier, et al. Characterization of acid catalytic domains for cellulose hydrolysis and glucose degradation. Biotechnology and bioengineering, Sep. 20, 2002; 79(6):1-9.
Mosier, et al. Characterization of Dicarboxylic Acids for Cellulose Hydrolysis. Biotechnol. Prog. 2001; 17:474-480.
Mosier, et al. Features of promising technologies for pretreatment of lignocellulosic biomass. Bioresource Technology. 2005;96:673-686.
Mullen, et al. Production of Deoxygenated Biomass Fast Pyrolysis Oils via Product Gas Recycling. Energy & Fuels; 2013; A-H.
Munoz, et al. Bioethanol production from bio-organosolv pulps of Pinus radiata and Acacia dealbata. J Chem Technol Biotechnol. 2007; 82:767-774.
Mythili, et al. Synthesis, mechanical, thermal and chemical properties of polyurethanes based on cardanol. Bull. Mater. Sci. Jun. 2004 ;27(3):235-241.
Nagamatsu, et al. Cascade-type flow of lignocellulosic components through the phase-separation system. J. Adv. Sci. 2001; 13(3):517-520.
Nagy, et al. Characterization of $CO_2$ precipitated Kraft lignin to promote its utilization. Green Chem. 2010; 12:31-34.
Nevell. The hydrolysis of cotton cellulose by hydrochloric acid in benzene. Dep. Polym. Fibre Sci., Univ. Manchester Inst. Sci. Technol., Manchester, UK. Carbohydrate Research (1976), 49 163-74. CODEN: CRBRAT ISSN: 0008-6215. Abstract only.
Nikam et al. Density and Viscosity Studies of Glucose and Fructose Solutions in Aqueous and in $NH_4CL$. Journal of Molecular Liquids; 2000; 87; 97-105.
Nogueira, et al. Crude tall-oil sodium salts micellization in aqueous solutions studied by static and dynamic light scattering. Colloids and Surfaces A: Physicochemical and Engineering Aspects. 2001; 191: 263-268.
Norman, et al. LXXIV. Studies on pectin. V. The hydrolysis of pectin. May 1, 1930; 649-660.
Novozymes application sheet. Cellic® CTec2 and HTec2-Enzymes for hydrolysis of lignocellulosic materials, Fuel Ethanol. 2010.
Novozymes application sheet. CellicTM CTec and Htec, Advanced enzymes for hydrolysis of lignocellulosic materials. Novozymes A/S No. 2009-05048-01. 2009.
Novozymes. The key to the first commercially viable enzymes for cellulosic ethanol. 2010. www.bioenergy.novozymes.com.
NREL. Enzyme Sugar-Ethanol Platform Project. National Renewable Energy Laboratory, Operated for the U.S. Department of Energy by Midwest Research Institute • Battelle • Bechtel. 2010.
NWBC. Program, 3rd Nordic Wood Biorefinery Conference (NWBC 2011), Stockholm, Sweden, Mar. 22-24, 2011.
NWBC-2009 The 2 nd Nordic Wood Biorefinery Conference. All Presentations; 2009.
Nystrand. Feasibility of lignocellulose as feedstock for biological production of super absorbent polymers. Department of Physics, Chemistry and Biology Master's Thesis; Linköping University Department of Physics, Chemistry and Biology 581 83 Linköping. Oct. 2010.
Odincovs, et al. The influence of temperature on the hydrolysis of wood and cellulose with concentrated hydrochloric acid. Trudy Inst. Lesokhoz. Problem, Akad. Nauk Latv. S.S.R. (1951), No. 2 68-82. Abstract only.
Odintsov, et al. Hydrolysis of woods with concentrated acids. Lesokhimicheskaya Promyshlennost (1940), 3(No. 9), 14-19. Abstract only.
Office action dated Mar. 22, 2013 for U.S. Appl. No. 13/225,346.
Office action dated Oct. 12, 2012 for U.S. Appl. No. 13/225,346.
Oh, et al. Pretreatment of Lignocellulosic Biomass using Combination of Ammonia Recycled Percolation and Dilute-Acid Process. J. Int. Eng. Chem. 2002; 8(1):64-70.
Oliet, et al. Solvent effects in autocatalyzed alcohol-water pulping comparative study between ethanol and methanol as delignifying agents. Chemical Engineering Journal. 2002; 87:157-162.
Olsson, et al. Fermentation of lignocellulosic hydrolysates for ethanol production. Enzyme and Microbial Technology. 1996; 18:312-331.
On, et al. Studies on pulp and paper mill fiber residues as resources. (II). Studies on acid hydrolysis of sludge. Coll. Eng., Jeonbuk Univ., Jenzu, S. Korea. Polpu, Chongi Gisul (1985), 17(1), 38-44. CODEN: PCGIDY ISSN: 0253-3200. Abstract only.
Onda et al. Selective Hydrolysis of Cellulose and Polysaccharides into Sugars by Catalytic Hydrothermal Method Using Sulfonated Activated-carbon. Journal of Japan Petroleum Institue.2012; 55(2): 73-86.
Ong. Conversion of lignocellulosic biomass to fuel ethanol—a brief review. The planter koala lumpur. 2004; 80(941):517-524.
Palmqvist, et al. Fermentation of lignocellulosic hydrolysates. II: inhibitors and mechanisms of inhibition. Bioresource Technology. 2000; 74:25-33.
Pan, et al. Bioconversion of Hybrid Poplar to Ethanol and Co-Products Using an Organosolv Fractionation Process : Optimization of Process Yields. Biotechnology and bioengineering. 2006; 94: 851-861.
Pan, et al. Biorefining of Softwoods Using Ethanol Organosolv Pulping: Preliminary Evaluation of Process Streams for Manufacture of Fuel-Grade Ethanol and Co-Products. Biotechnology and bioengineering. May 20, 2005; 90(4).
Pan, et. al. Pretreatment of Lodgepole Pine Killed by Mountain Pine Beetle Using the Ethanol Organosolv Process: Fractionation and Process Optimization. Ind. Eng. Chem. Res. 2007;46: 2609-2617.
Pandey, et al. Lignin depolymerization and conversion: a review of thermochemical methods. Chemical Engineering and Technology. 2011; 34(1):29-41.
Papadopoulos, et al. The behavior of lignin during hydrolysis of sweetgum wood with concentrated hydrochloric acid at moderate temperatures. Dep. Wood Paper Sci., North Carolina State Univ.,

(56) References Cited

OTHER PUBLICATIONS

Raleigh, NC, USA. Holzforschung (1981), 35(6), 283-6. Coden: HOLZAZ ISSN: 0018-3830. Abstract only.
Papadopoulou et al. The Challenge of Bio-Adhesives for the Wood Composite Industries. Report; Theassaloniki, Greece. 2012.
Papadopoulous, et al. Behavior of sweetgum wood xylan and lignin during hydrolysis with concentrated hydrochloric acid at moderate temperatures. Dep. Wood Pap. Sci., North Carolina State Univ., Raleigh, NC, USA. Journal of Applied Polymer Science: Applied Polymer Symposium (1983), 37(Proc. Cellul. Conf., 9th, 1982, Part 2), 631-40. Coden: JPSSDD ISSN: 0271-9460. Abstract only.
Papajannopoulous, et al. GC-MS analysis of oleoresin of three Greek pine species. Holz als Roh- und Werkstoff 2001; 59:443-446.
Parisi. Advances in Lignocellulosics Hydrolysis and in the Utilization of the Hydrolyzates. Advances in Biochemical Engmeering/Biotechnology. 1989; 38:53-87.
Parpot et al. Electrochemical investigations of the oxidation—reduction of furfural in aqueous medium. Electrochimica Acta; 2004; 49; 397-403.
Pasquini, et al. Extraction of lignin from sugar cane bagasse and Pinus taeda wood chips using ethanol—water mixtures and carbon dioxide at high pressures. J. of Supercritical Fluids. 2005; 36:31-39.
Pasquini, et al. Sugar cane bagasse pulping using supercritical CO2 associated with co-solvent 1-butanol/water. J. of Supercritical Fluids. 2005; 34:125-131.
Paszner, et al. High-yield Organosolv process for conversion of cellulosic biomass to ethanol. Fac. For., Dep. Harvest. Wood Sci., Vancouver, BC, Can. Energy from Biomass and Wastes (1989), 12 1297-318. CODEN: EBWADU ISSN: 0277-7851. Abstract only.
Patel, et al. Medium and long-term Opportunities and Risks of the Biotechnological Production of Bulk Chemicals from Renewable Resources—The Potential of White Biotechnology the BREW project. Utrecht University. Sep. 2006. www.chem.uu.nl/nws.
Paul, et al. Optical absorption and fluorescence studies on imidazolium ionic liquids comprising the bis (trifluoromethanesulphonyl)imide anion. J. Chem. Sci.; 2006; 118(4); 335-340.
Pazur. Reversibility of enzymatic transglucosylation reactions. Received for publication, Jan. 17, 1955, pp. 531-538.
Pepper, et al. The Isolation of a Representative Lignin Fraction From Wood and Straw Meals. Canadian J. of Chemistry. 1962; 40:1026-1028.
Perlack, et al. Biomass as feedstock for a bioenergy and bioproducts industry: the technical feasibility of a billion-ton annual supply. U.S. Department of Energy, under contract DE-AC05-00OR22725. Apr. 2005.
Pessoa Jr, et al. Acid hydrolysis of hemicellulose from sugarcane bagasse. Braz. J. Chem. Eng. vol. 14 No. 3 São Paulo Sep. 1997.
Peterson, et al. Thermochemical biofuel production in hydrothermal media: A review of sub and supercritical water technologies. Energy & Enviromental Science. 2008; 1:32-65.
Petkevich, et al. Hydrolysis of wood with concentrated hydrochloric acid in a pilot battery of diffusers. Sb. Tr., Gos. Nauchn.-Issled. Inst. Gidrolizn. i Sul'fitno-Spirt. Prom. (1960), 8 47-65. Abstract only.
Pettersen. The Chemical Composition of Wood. In: Rowell M., ed. The chemistry of solid wood. Advances in chemistry series 207. Washington, DC: American Chemical Society ; 1984: Chapter 2.
Philip, et al. Review Polyhydroxyalkanoates: biodegradable polymers with a range of applications. J Chem Technol Biotechnol. 2007; 82:233-247.
Phillips, et al. Thermochemical Ethanol via Indirect Gasification and Mixed Alcohol Synthesis of Lignocellulosic Biomass. National Renewable Energy Laboratory, Technical Report NREL/TP-510-41168. Apr. 2007.
Phillips. Technoeconomic Analysis of a Lignocellulosic Biomass Indirect Gasification Process to Make Ethanol. Ind. Eng. Chem. Res. 2007; 46:8887-8897.
Pierce. Instruction Acylation Derivatization Reagents. Pierce, Rockford, IL 61105, US. 2010.
Ping, et al. Evaluation of grape stalks as a bioresource. Industrial Crops and Products. 2011; 33:200-204.

Pisarnitsky, et al. Effect of Acid Hydrolysis of Oak Wood on Its Aroma-Forming Complex. Applied Biochemistry and Microbiology. 2004; 40(6):613-616.
Pogaku, et al. Whey Protein Isolate-Starch System—A Critical Review. International Journal of Food Engineering: vol. 3 : Iss. 6, Article 1. 2007.
Polymer Science. Making Polyurethane. Polymer Science Learning Center, Department of Polymer Science the University of Southern Mississippi. 2005.
Pontin. First, Cure Malaria. Next Global Warming. The New York times/SundayBusiness/Bright Ideas. Jun. 3, 2007.
Popa, et al. A comparison concerning separation and characterization of polyphenols from spruce wood bank. 2010.
Prater, et al. Determination of Sulfur Dioxide in Dehydrated Foods. Industrial and engineering chemistry. Mar. 1944; 16(3):153-157.
Priefert, et al. Biotechnological production of vanillin. Appl Microbiol Biotechnol. 2001; 56:296-314. Abstract only.
Pulping and Bleaching, PSE 476 powerpoint. 2011.
Purolite. Corn sweetener refining with ion exchange resins guide. The Purolite Compant. 2007. 60 pages. www.purolite.com.
Pye. The Alcell Process—A Proven Alternative to Kraft Pulping. 1990 Pulping Conference, TAPPI Proceedings. 991-996.
Qian, et al. Acidic Sugar Degradation Pathways an Ab Initio Molecular Dynamics Study. Applied Biochemistry and Biotechnology. 2005;121-124:989-997.
Quinde. Enzymes in the pulp and paper industry: a review. 1994.
Rabinovich. Wood hydrolysis industry in the Soviet Union and Russia: a mini-review. Cellulose Chem. Technol.2010; 44(4-6):173-186.
Radiotis, et al. Optimizing Production of Xylose and Xylooligomers from Wood Chips. 3rd NWBC, Stockholm, Sweden Mar. 23, 2011.
Ragauskas, et al. From wood to fuels Integrating biofuels and pulp production. Industrial biotechnology. 2006; 2(1):55-65.
Ragauskas, et al. The Path Forward for Biofuels and Biomaterials. Science. Jan. 26, 2006; 311:484-489.
Raz. Literature review on concentrated HCl hydrolysis of lignocellulosic material. Aug. 2008.
Raz. Weyland bioethanol report. 2010.
Reese. A microbiological process report; enzymatic hydrolysis of cellulose. Appl Microbiol. Jan. 1956;4(1):39-45.
Reinhold. SEC of lignins. Mainz, Germany. 2007.
Reinhold. SEC of lignins. Mainz, Germany. Powerpoint. 2007.
Rinaldi, et al. Acid hydrolysis of cellulose as the entry point into biorefinery schemes. Chemsuschem. Dec. 21, 2009; 2(12):1096-1107.
Ritcey et al. Development of Industrial Solvent Extraction Processes. (Report) Gordon M. Ritcey & Associates, Inc; Nepean, Ontario, Canada.2004.
Robbins, et al. Liquid-Liquid Extraction Operations and Equipment. Sec. 15. 2009.
Robertson. Factors Governing the Nitration of Cellulose. PhD Thesis; Cornell University. 1946.
Robertson. The fractional extraction and quantitative determination of pectic substances in grapes and musts. Am. J. Enol. Vitic. 1979; 30(3):182-186.
Rockwood, et al. Energy Product Options for Eucalyptus Species Grown as Short Rotation Woody Crops. Int. J. Mol. Sci. 2008; 9:1361-1378; DOI: 10.3390/ijms9081361.
Roman-Leshkov et al. Production of dimethylfuran for liquid fuels from biomass-derived carbohydrates. Nature; 2007; 447; 982-985.
Rondinini, et al. Reference value standards and primary standards for pH measurements in Organic Solvents and Water + Organic Solvent Mixtures of Moderate to High Permittivities. Pure & Appl. Chem. 1987; 59(11):1549-1560.
Rout et al. Supercritical CO2 Fractionation of Bio-oil Produced from Mixed Biomass of Wheat and Wood Sawdust. Energy & Fuels; 2009; 13; 6181-6188.
Rovio, et al. Determination of monosaccharide composition in plant fiber materials by capillary zone electrophoresis. Journal of Chromatography A. 2008; 1185:139-144.
Rovio, et al. Determination of neutral carbohydrates by CZE with direct UV detection. Electrophoresis. 2007; 28:3129-3135.

(56) References Cited

OTHER PUBLICATIONS

Rozmarin, et al. Fermentative evaluation of prehydrolyzates from chemical cellulose manufacturing. II. Study on some factors affecting the inversion process. Rom. Revista Padurilor-Industria Lemnului-Celuloza si Hirtie: Celuloza si Hirtie (1977), 26(4), 158-62. CODEN: RPLHDX ISSN: 0258-2287. Abstract only.
Rugg. Optimization of the NYU continuous cellulose hydrolysis process. B01447 Biofuels Information Center. Dec. 1982.
Ruiz-Angel et al. Reversed-phase liquid chromatography analysis of alkyl-imidazolium ionic liquids II. Effects of different added salts and stationary phase influence. Journal of chromatography A; 2008, 1189; 476-482.
Rumbold. Selection of production hosts for real-life feedstock utilization. TNO Kwaliteit van Leven, Oct. 20, 2007.
Saari et al. Adsorption Equilibria of Arabinose, Fructose, Galactose, Rhamnose, Sucrose, and Xylose on Ion-Exchange Resins. J. Chem. Eng.; 2010; 55; 3462-3467.
Saariaho. Resonance raman spextroscopy in the analysis of residual lignin and other unsaturated structures in chemical pulps. Helsinki University of Technology (Espoo, Finland) on Jan. 14, 2005.
Saeman. Kinetics of the hydrolysis of wood and of the decomposition of sugars in dilute acid at high tempratures. USDA. Sep. 1944.
Saha, et al. Dilute Acid Pretreatment, Enzymatic Saccharification, and Fermentation of Rice Hulls to Ethanol. Biotechnol. Prog. 2005; 21:816-822.
Sakai et al. Effect of lignocellulose-derived inhibitors on growth of and ethanol production by growth-arrested Corynebacterium glutamicum R. Applied and environmental microbiology; 2007; 73(7); 2349-2353.
Saltberg, et al. Removal of metal ions from wood chips during acidic leaching 1:Comparison between Scandinavian softwood, birch and eucalyptus. Nordic Pulp and Paper Research J. 2006; 21(4):507-512.
Saltberg, et al. Removal of metal ions from wood chips during acidic leaching 2: Modeling leaching of calcium ions from softwood chips. Nordic Pulp and Paper Research J. 2006; 21(4):513-519.
Samuel, et al. Structural Characterization and Comparison of Switchgrass Ball-milled Lignin Before and after Dilute Acid Pretreatment. Appli. Micr. BioTech. 2010, 162:62-74.
Sanchez, et al. Structural analysis of acid catalysed furfuraldehyde resins by thermal degradation techniques. Eur. Polym. J. 1994; 30(1):43-50.
Sanchez, et al. Trends in biotechnological production of fuel ethanol from different feedstocks. Bioresource Technology. 2008; 99:5270-5295.
Sanders, et al. Shuttle hydrochloric acid process for the preparation of oligosaccharides containing products from wood. Comm. Eur. Communities, [Rep.] Eur (1987), (Eur 11084, Degrad. Lignocellul. Ruminants Ind. Processes), 97-101. CODEN: CECED9 ISSN: 0303-755X. Abstract only.
Sannigrahi, et al. Cellulosic biorefineries—unleashing lignin opportunities. Current Opinion in Environmental Sustainability. 2010; 2:383-393.
Sannigrahi, et al. Effects of Two-Stage Dilute Acid Pretreatment on the Structure and Composition of Lignin and Cellulose in Loblolly Pine. Bioenerg. Res. 2008; 1:205-214.
Sannigrahi, et al. Pseudo-lignin and pretreatment chemistry. Energy Environ. Sci. 2011; 4:1306-1310.
Sarangi, et al. Removal/recovery of hydrochloric acid using alamine 336, aliquat 336, TBP and cyanex 923. Hydrometallurgy. 2006; 84(3-4):125-129.
Sasaki, et al. Cellulose hydrolysis in subcritical and supercritical water. J. of Supercritical Fluids. 1998; 13:261-268.
Sassner, et al. Techno-economic evaluation of bioethanol production from three different lignocellulosic materials. Biomass and bioenergy. 2008; 32:422-430.
Sato, et al. Determination of monosaccharides derivatized with 2-aminobenzoic Acid by capillary electrophoresis. Ana. BioChem. 1997; 251: 119-121.

Scaringelli, et al. Pre-hydrolysis of sweetgum wood—An integrated approach to the conversion of lignocellulose from wood into useful chemicals. Report (1979), (NSF/RA-790218; Order No. PB80-108640), 38 pp. From: Gov. Rep. Announce. Index (U. S.) 1980, 80(5), 810. Abstract only.
Schaefer. Bio-Based opportunities in chemicals & energy. Novozymes. London, UBS. Nov. 17, 2010.
Schlamadinger, et al. Effects of the Kyoto protocol on forestry and bioenergy products for mitigation of net carbon emissions. IEA Bioenergy, proceedings of the workshop. Apr. 1998. 202 pages.
Schoenemann. The New Rheinau Wood Saccharification Process. Institute of Chemical Technology. Jul. 27, 1953; 1-49.
Schuchardt et al. Hydrolysis of sugar cane bagasse with hydrochloric acid, promoted by metallic cations. Journal of Chemical Technology & Biotechnology. 1986; 36:329-334.
Schutz. The hydrolysis of wood with hydrochloric acid or chlorides as catalysts in acetic acid solution. Zellwolle, Kunstseide, Seide (1942), 47:8-9. Abstract only.
Scifinder. Steam pretreatment of wood in relation to enzymatic hydrolysis. Final report. Energy Res. Abstr. 1989, 14(17), Abstr. No. 35904.
Scurfield, et al. Amino-Acid Composition of Wood Proteins. J. Experimental.Botany. 1970; 21(6):857-68.
Sen, et al. A Review of Cellulose Non-Derivatizing Solvent Interactions with Emphasis on Activity in Inorganic Molten Salt Hydrates. Sustainable Chemistry & Engineering. 2013:858-870.
Sendich, et al. Recent process improvements for the ammonia fiber expansion (AFEX) process and resulting reductions in minimum ethanol selling price. Bio. Tech. 2008; 99:8429-8435.
Sharkov, et al. Conversion of difficult-to-hydrolyze wood polysaccharides to an easy-to-hydrolyze condition with hydrogen chloride under pressure. USSR. Sb. Tr., Vses. Nauch.-Issled. Inst. Gidroliza Rast. Mater. (1971), No. 21 65-74, 205. Abstract only.
Sharkov. Production of Polyhydric Alcohols from Wood Polysaccharides. Angew. Chem. internat. Edit. 1963; 2(8):405-492.
Shatalov, et al. Kinetics of organosolv delignification of fibre crop Arundo donax L. Industrial Crops and Products. 2005; 21:203-210.
Sheehan, et al. Energy and Environmental Aspects of Using Corn Stover for Fuel Ethanol. Journal of Industrial Ecology. 2004; 7(3-4):117-146.
Shen, et al. Product overview and market projection of emerging bio-based plastics, Utrecht University. PRO-BIP 2009.
Sherrard, et al. Review of wood saccharification processes in the United States Prior to World War II. Industrial and Engineering Chemistry. 1945. 37(1):1-10.
Shimizu, et al. Integrated process for total utilization of wood components by steam-explosion pretreatment. Biomass and bioenergy. 1998; 14(3):195-203.
Sidiras, et al. Simulation of acid-catalysed organosolv fractionation of wheat straw. Bioresource Technology. 2004; 94:91-98.
Sigma. Enzymatic Assay of α-Glucosidase. Sigma quality control test procedure. Sigma Product information, Revised: Aug. 9, 1996.
Sigma. Enzymes and Reagents for Alternative Energy. Sigma-Aldrich. Biofiles. 2010; 5(5).
Singh, et al. Visualization of Biomass Solubilization and Cellulose Regeneration During Ionic Liquid Pretreatment of Switchgrass. Biotechnology and Bioengineering. Sep. 1, 2009; 104(1):68-75.
Sluiter, et al. Compositional analysis of lignocellulosic feedstocks. 1. Review and description of methods. Journal of agricultural and food chemistry. 2010; 58:9043-9053.
Sluiter, et al. Determination of Ash in Biomass, Laboratory Analytical Procedure (LAP), Issue Date: Jul. 17, 2005. Technical Report, NREL/TP-510-42622, Jan. 1, 2008.
Sluiter, et al. Determination of Sugars, Byproducts, and Degradation Products in Liquid Fraction Process Samples, Laboratory Analytical Procedure (LAP), Issue Date: Dec. 8, 2006. Technical Report, NREL/TP-510-42623, Jan. 1, 2008.
Sluiter, et al. Determination of Sugars, Byproducts, and Degradation Products in Liquid Fraction Process Samples. Laboratory Analytical Procedure (LAP), Contract No. DE-AC36-99-GO10337. Issue Date: Dec. 8, 2006.
Sluiter, et al. Determination of Total Solids in Biomass and Total Dissolved Solids in Liquid Process Samples, Laboratory Analytical

(56) References Cited

OTHER PUBLICATIONS

Procedure (LAP), Issue Date: Mar. 31, 2008. Technical Report, NREL/TP-510-42621, Revised Mar. 2008.
So, et al. Economic Analysis of Selected Lignocellulose-to-Ethanol Conversion Technologies. Applied Biochemistry and Biotechnology. 1999; 77-79:633-640.
Soloman, et al. Grain and cellulosic ethanol: History, economics, and energy policy. Biomass and Bioenergy. 2007; 31:416-425.
Spaccini, et al. Molecular characteristics of humic acids extracted from compost at increasing maturity stages. Soil Biology & Biochemistry. 2009 41:1164-1172.
Srinorakutara, et al. Approach of Cassava Waste Pretreatments for Fuel Ethanol Production in Thailand. 2010.
Srinorakutara, et al. Utilization of Waste from Cassava Starch Plant for Ethanol Production. The Joint International Conference on "Sustainable Energy and Environment (SEE)" Dec. 1-3, 2004, Hua Hin, Thailand. 344-349.
Srndovic. Ultrastructure of the primary cell wall of softwood fibres studied using dynamic FT_IR spectroscopy. Licentiate Thesis, Royal Institute of Technology. Stockholm 2008.
Steele. Recent breakthroughs in enzymes for biomass hydrolysis. Genecor. National Ethanol Conference, Feb. 23-25, 2009, San Antonio, Texas.
Steinbuchel. Polymeric and low molecular weight hydrophobic chemicals produced by microorganisms from renewables. Renewable Resources & Biorefineries Conference, Sep. 6-8, 2006, York, UK.
Stepnowski et al. Analysis of Environmental Fate and Quantitative Methods for Determination of Ionic Liquids. Conference report; International Conference on Enviromental Science and Technology. 2007; KOS, Greece.
Stranges. Friedrich Bergius and the Rise of the German Synthetic Fuel Industry. Isis. Dec. 1984; 75(4):43-667.
Stranges. Synthetic fuel production in prewar and world war II Japan: A case study in technological failure. Annals of Science. 1993; 50:229-265.
Structure of Wood. US Department of Agriculture, Forest Service, Forest Products Laboratory, Research Note FPL-04. Mar. 1980.
Sudo, et al. A New Modification Method of Exploded Lignin for the Preparation of a Carbon Fiber Precursor. Journal of Applied Polymer Science. 1993; 48:1485-1491.
Sun, et al. Hydrolysis of lignocellulosic materials for ethanol production: a review. Bioresource Technology. 2002; 83:1-11.
Taherzadeh, et al. Acid-Based hydrolysis Processes for Ethanol from Lignocellulosic materials: A Review. Bioethaol review, BioResources. 2007; 2(3):472-499.
Taherzadeh, et al. Pretreatment of Lignocellulosic Wastes to Improve Ethanol and Biogas Production: A Review. Int. J. Mol. Sci. 2008; 9:1621-1651; DOI: 10.3390/ijms9091621.
Takagaki et al. Catalytic Transformations of Biomass-Derived Materials into Value-Added Chemicals. Catalysis Surveys from Asia. 2012; 16: 164-182.
Tanaka, et al. Effect of Pore Size in Substrate and Diffusion of Enzyme on Hydrolysis of Cellulosic Materials with Cellulases. Biotechnology and Bioengineering. 1998; 32:698-706.
Tanase, et al. Mass Balance of Extractives Around Impressafiner in Mill and Pilot Scale. 2009. 1-6.
Tang, et al. Effect of Inorganic Salts on Pyrolysis of Wood, Cellulose, and Lignin Determined by Differential Thermal Analysis. U.S. Forest Service Research FPL 82 Jan. 1968.
Tappi. Acid-insoluble lignin in wood and pulp. T 222 om-88, TAPPI 1988.
The US Pushes for Advanced Biofuels Market Growth. Global Data; A report.2010: 1-7.
Thompson, et al. Comparison of Pretreatment Methods on the Basis of Available Surface Area. Bioresource Technology. 1992; 39:155-163.
Thomsen. How 'green' are algae farms for biofuel production? Biofuels. 2010; 1(4):515-517.
Timell, et al. The acid hydrolysis of glycosides II. Effect of substituents at C-5. Canadian Journal of Chemistry. 1965; 43:2296-2305.
Timell. The acid hydrolysis of glycosides I. General conditions and the effect of the nature of the aglycone. Canadian Journal of Chemistry. 1964; 42:1456-1471.
Timur, et al. Characterization and application of activated carbon produced from oak cups pulp. Journal of Analytical and Applied Pyrolysis. 2010; 89:129-136.
Trickett. Utilization of Baggase for the production of C5 and C6 sugars. MS Thesis; University of Natal, Durban, South Africa. 1982.
Trinh et al. Fast Pyrolysis of Lignin Using a Pyrolysis Centrifuge Reactor. Energy & Fuels. 2013; 27 (7): 3802-3810.
Troitskii. Colloid chemical mechanism of the separation of some elements by extraction. Russ. Chem. Rev. 163; 32:116-120.
Unal, et al. Dechlorination of Bleached Kraft Pulp by Laccase Enzyme Produced from Some White-Rot Fungi. Turk J Biol. 2001; 25:67-72.
Updegraff et al. Semimicro determination of cellulose in biological materials. Analytical biochemistry. 1969; 32(3):420-424.
Urban, et al. Characterization of polymer-based monolithic capillary columns by inverse size-exclusion chromatography and mercury-intrusion porosimetry. Journal of Chromatography A. 2008; 1182:161-16.
USDA. A USDA Regional Roadmap to Meeting the Biofuels Goals of the Renewable Fuels Standard by 2022. A USDA Report. 2010.
USDE. Advanced Technologies for the Control of Sulfur Dioxide Emissions from Coal-Fired Boilers, A report on three projects conducted under separate. Clean Coal Technology. Topical Report No. 12, Jun. 1999.
Vaghela et al. Electrolytic synthesis of succinic acid in a flow reactor with solid polymer electrolyte membrane. Journal of Applied Electrochemistry. 2002; 32: 1189-1192.
Van Bramer. An Introduction to Mass Spectrometry. Widener University, Department of Chemistry, One University Place, Chester, PA 19013. 1998.
Van Dam. Characterization of Sulfur-free lignins from alkaline pulping of annual fibere crops. The international Lignin Institute, 5th international Forum Sep. 7, 2000, Bordeaux (France).
Van Dyke. Enzymatic Hydrolysis of Cellulose—A Kinetic Study. For the degree of Doctor of Science at the Massachusetts Institute of Technology, Sep. 1972.
Van Sprongsen, et al. Separation and recovery of the constituents from lignocellulosic biomass by using ionic liquids and acetic acid as co-solvents for mild hydrolysis. Chemical Engineering and Processing. 2011; 50:196-199.
Van-Putten et al. Hydroxymethylfurfural, a versatile platform chemical made from renewable resources. Chemical reviews. 2013;113 : 1499-1597.
Vennestrom, et al. Beyond petrochemicals: the renewable chemicals industry. Angewandte Chemie Int. Ed. 2011; 50:10502-10509.
Von Sivers, et al. A techno-economical comparison of three processes for the production of ethanol from pine. Bioresource Technology. 1995; 51:43-52.
Vulfson, et al. Glycosidases in organic solvents: I. Alkyl-fl-glucoside synthesis in a water-organic two-phase system. Enzyme Microb. Technol. Dec. 1990; 12:950-954.
Vuyyuru et al. Conversion of Cellulosic Biomass into Chemicals using Heterogeneous and Electrochemical Catalysis. MS Thesis, Berlin University, 2012.
Wang et al. A Route for Lignin and Bio-Oil Conversion: Dehydroxylation of Phenols into Arenes by Catalytic Tandem Reactions. Angewandte Chemie. 2013; 52: 11499-11503.
Wang, et al. Influence of steaming explosion time on the physic-chemical properties of cellulose from Lespedeza stalks (*Lespedeza crytobotrya*). Bioresource Technology. 2009; 100:5288-5294.
Wang, et al. Molecular Characteristics of Kraft-AQ Pulping Lignin Fractionated by Sequential Organic Solvent Extraction. Int. J. Mol. Sci. 2010; 11:2988-3001.
Wang, et al. Understanding the Conformation of Polysaccharides. Chapter 5. Copyright 2005 by Taylor & Francis Group, LLC.

(56) References Cited

OTHER PUBLICATIONS

Wang, et al. Understanding the Physical Properties of Food Polysaccharides. Chapter 4. Copyright 2005 by Taylor & Francis Group, LLC.
Wang. Thermal Modification of Wood. Faculty of Forestry University of Toronto. 2011.
Wasserscheid & Welton. Ionic Liquids in Synthesis. A book ; Published by Wiley-VCH Verlag GmbH & Co. KGaA. 2007:1-709.
Wei, et al. Effects of surfactant on biochemical and hydrothermal conversion of softwood hemicellulose to ethanol and furan derivatives. Process Biochemistry. 2011; 46(9): 1785-1792.
Weingarten, et al. Kinetics of furfural production by dehydration of xylose in a biphasic reactor with microwave heating. Green Chem. 2010; 12:1423-1429.
Werner et al. Ionic liquids in chemical engineering. Annual review of chemical and biomolecular engineering. 2010; 1: 203-230.
Williams. Ethanol production potential and costs from lignocellulosic resources in California. 15th European Biomass Conference & Exhibition, May 7-11, 2007, Berlin, Germany.
Wilson, et al. Detection of tannins in modern and fossil barks and in plant residues by high-resolution solid-state $^{13}$C nuclear magnetic resonance. Org. Geochem. 1988; 12(6):539-546.
Winandy, et al. Wood-plastic composites using thermomechanical pulp made from oxalic acid-pretreated red pine chips. 7th Global WPC and Natural Fibre Composites Congress and Exhibition, Jun. 18-19, 2008 in Kassel / Germany.
Winston, et al. Characterization of the lignin residue from hydrolysis of sweetgum wood with superconcentrated hydrochloric acid. Holzforschung Bd.1986; 40:Suppl. 45-50.
Wood, et al. Determination of Methanol and Its Application to Measurement of Pectin Ester Content and Pectin Methyl Esterase Activity. Analytical biochemistry. 1971; 39:418-428.
Woodbridge et al. Nitrocellulose from wood pulp. J. Ind.Eng. Chem. 1920; 12(4):380-384.
Wood-Ethanol Report. Environment Canada. 1999.
Wright et al. Techno-Economic Analysis of Biomass Fast Pyrolysis to Transportation Fuels. Technical Report: NREL/TP-6A20-46586. 2010.
Wyman et al. Pretreatment : The Key to Unlocking Low Cost Cellulosic Ethanol Ethanol Production in Brazil and the United States. Presentation. CAFI. 2007.
Wyman, et al. Comparative sugar recovery data from laboratory scale application of leading pretreatment technologies to corn stover. Bioresource Technology. 2005; 96: 2026-2032.
Wyman, et al. Coordinated development of leading biomass pretreatment technologies. Bioresource Technology. 2005; 96:1959-1966.
Wyman. Biomass ethanol: Technical Progress, Opportunities, and Commercial Challenges. Annu. Rev. Energy Environ. 1999; 24:189-226.
Wyman. Potential Synergies and Challenges in Refining Cellulosic Biomass to Fuels, Chemicals, and Power. Biotechnol. Prog. 2003; 19:254-262.
Wyman. Twenty Years of Trials, Tribulations, and Research Progress in Bioethanol Technology. Applied Biochemistry and Biotechnology. 2001; 91-93:5-21.
Wyman. What is (and is not) vital to advancing cellulosic ethanol. TRENDS in Biotechnology. 2007; 25(4):153-157.
Xiang, et al. Heterogeneous Aspects of Acid Hydrolysis of α-Cellulose. Applied Biochemistry and Biotechnology. 2003; 105-108:505-514.
Xie, et al. Opportunities with Wood Dissolved in Ionic Liquids. In Cellulose Solvents: Foe Analysis, Shaping and Chemical Modification. Chapter 19. 2010;343-363.
Xing, et al. Production of furfural and carboxylic acids from waste aqueous hemicellulose solutions from the pulp and paper and cellulosic ethanol industries. Energy & Environmental Science. 2011; 4: 2193-2205.
Yang et al. Optimization of furfural production from D-xylose with formic acid as catalyst in a reactive extraction system. Bioresource technology. 2013; 133 : 361-369.
Yang et al. Synthesis of furfural from xylose, xylan, and biomass using AlCl3.6H2O in biphasic media via xylose isomerization to xylulose. ChemSusChem. 2012; 5: 405-410.
Yang, et al. Pretreatment: the key to unlocking low-cost cellulosic ethanol. Biofuels, Bioprod. Bioref. 2008; 2:26-40.
Ye, et al. Spontaneous High-Yield Production of Hydrogen from Cellulosic Materials and Water Catalyzed by Enzyme Cocktails. ChemSusChem. 2009; 2:149-152.
Yeoh, et al. Comparisons between different techniques for water-based extraction of pectin from orange peels. Desalination 2008; 218:229-237.
Yoshida, et al. Gasification of biomass model compounds and real biomass in supercritical water. Biomass and Bioenergy.2004; 26:71-78.
Yusmawati, et al. Optical Properties and Sugar Content Determination of Commercial Carbonated Drinks using Surface Plasmon Resonance. American Journal of Applied Sciences. 2007; 4(1):01-04.
Zahalka, et al. Esterification of 1,4-dichlorobutane with sodium formate under solid-liquid phase transfer catalysis. A kinetic study. Can. J. Chem. 1989; 67:245-249.
Zahalka, et al. One-Pot Conversion of Primary Alkyl Chlorides and Dichlorides into Alcohols, Diols and Ethers via Formic Ester Intermediated under Phase-Transfer Conditions. Communications, Sep. 1986; 763-765.
Zahedifar. Novel uses of lignin and hemicellulosic sugars from acidhyrolysed lignocellulosic materials. For the degree of Doctor of Philosophy, in the University of Aberdeen, Sep. 1996.
Zhang et al. Hydrodeoxygenation of lignin-derived phenolic monomers and dimers to alkane fuels over bifunctional zeolite-supported metal catalysts. Substainable Chemistry and Engineering; 2013; 1-30.
Zhang, et al. Conversion of Xylan and Xylose into Furfural in Biorenewable Deep Eutectic Solvent with Trivalent Metal Chloride Added. BioResources; 8(4);6014-6025.
Zhang, et al. Conversion of xylan, d-xylose and lignocellulosic biomass into furfural using AlCl3 as catalyst in ionic liquid. Bioresource technology. 2013; 130 : 110-116.
Zhang, et al. Solid acids as catalysts for the conversion of D-xylose, xylan and lignocellulosics into furfural in ionic liquid. Bioresource technology. 2013; 136 : 515-521.
Zhang. Reviving the carbohydrate economy via multi-product lignocellulose biorefineries. J Ind Microbiol Biotechnol. 2008; 35:367-375.
Zhao et al. Aromatics Production via Catalytic Pyrolysis of Pyrolytic Lignins from Bio-Oil. Energy & Fuels. 2010; 24: 5735-5740.
Zhao, et al. Small-scale mashing procedure for predicting ethanol yield of sorghum grain. Journal of Cereal Science. 2009; 49:230-238.
Zhao, et al. Supercritical hydrolysis of cellulose for oligosaccharide production in combined technology. Chem. Eng. J. 2009; 150:411-417.
Zheng, et al. Overview of biomass pretreatment for cellulosic ethanol production. Int J Agric & Biol Eng. 2009; 2(3):51-68.
Zheng, et al. Phenolation of walnut shell using sulfuric acid as a catalyst and application to PF resin adhesives. Abstracts / Journal of Biotechnology 136S (2008) S402-S459, doi:10.1016/j.jbiotec.2008.07.950.
Zheng, et al. Supercritical carbon dioxide explosion as a pretreatment for cellulose hydrolysis. Biotechnology Letters. Aug. 1995; 17(8):845-850.
Zhu, et al. Understanding methanol formation in pulp mills. 1999 International Environmental Conference, pp. 139-143.
Zimbardi, et al. Acid impregnation and steam explosion of corn stover in batch processes. Industrial Crops and Productions. 2007; 26:195-206.
Zinoviev, et al. Background Paper on biofuels Production Technologies. International Center for Science and High Technology and UNIDO. Nov. 2007; 1-106.

(56) References Cited

OTHER PUBLICATIONS

Zorina, et al. Study of acid heterogeneous hydrolysis of pulp. USSR. Editor(s): Kiprianov, A. I. Khim Pererab. Drev. (1982), 35-8. Publisher: Leningr. Lesotekh.Akad., Leningrad, USSR CODEN: 49HIA6. Abstract only.
ASTM Standards. Standard Test Method for Ash in Biomass. Designation: E1755-01 (Reapproved 2007).
Satin Sweet® 65% High Maltose Corn Syrup. Cargill foods. www.cargillfoods.com Updated Aug. 12, 2014.
Eyal, et al. Recovery and concentration of strong mineral acids from dilute solutions through LLX.I: review of parameters for adjusting extractant propert and analysis of process options. Solvent Extraction and ion exchange. 1991; 9(2):195-210.
Eyal, et al. Sulfuric acid recovery through solvent aided decomposition of ammonium sulfate. Solvent Extraction and ion exchange. 1986; 44:803-821.
Fahim, et al. Liquid-Liquid Equilibria of the Ternary System Water + Acetic Acid + 1-Hexanol. J. Chem. Eng. Data. 1997; 42:183-186.
Suess. Interaction of organic compounds with calcium carbonate-I. Association phenomena and geochemical implications. Geochimia et Cosmochimic Acata. 1970; 34:157-168.
Allosio-Ouarnier, et al. Application of High Performance Anion Exchange Chromatography to the Study of Carbohydrate Changes in Barley During Malting. Journal—Institute of Brewing 106(1):45-52. Jan. 2000.
Notice of Allowance dated Jan. 30, 2017 for U.S. Appl. No. 15/093,698.
Sevcik, et al. Rapid analysis of carbohydrates in aqueous extracts and hydrolysates of biomass using a carbonate-modified anion-exchange column. J Chromatogr A. Mar. 4, 2011;1218(9):1236-43. doi: 10.1016/j.chroma.2011.01.002. Epub Jan. 11, 2011.
Cassales, et al. Optimization of soybean hull acid hydrolysis and its characterization as a potential substrate for bioprocessing. Biomass and Bioenergy. 2011; 35:4675-4683.
Corn sweetener guide. Corn sweetener refining with ion exchange resins. Purolite. Jan. 18, 2007. 60 pages.
Delgado, et al. Sugar processing and by-products of the sugar industry. FAO Agricultural Services Bulletin 144. Rome, 2001.
Dever, et al. Partial Chemical Characterization of Corn Root Cell Walls. Plant Physiol 43, 50-56, 1968.
Dowex Ion exchange resins for HFCS deashing and polishing. Technical Manual. The Dow Chemical Company. Published Jun. 2002. 28 pages.
European search report and opinion dated May 4, 2015 for EP Application No. 14197793.4.
Eyal, et al. Extraction of Strong Mineral Acids by Organic Acid-Base Couples. Ind. Eng. Chem. Process Des. Dev. 1982, 21, 334-337.
Ferrari, et al., Ethanol production from eucalyptus wood hemicellulose hydrolysate by pichia stipitis, 1992, biotech and bioengineering, 40:753-759.
Hanchar, et al. Separation of glucose and pentose sugars by selective enzyme hydrolysis of AFEX-treated corn fiber. Appl Biochem Biotechnol. Apr. 2007;137-140(1-12):313-25. doi: 10.1007/s12010-007-9061-3.
Holmen. Direct conversion of methane to fuels and chemicals. Catalysts Today. 2009; 142:2-8.
International search report and written opinion dated Feb. 15, 2013 for PCT/US2012/059542.
Ismagilov, et al. Direct conversion of methane on Mo/ZSM-5 catalysts to produce benzene and hydrogen: achievements and perspectives. Energy and Environmental Science. 2008; 1:526-541.

Kaparaju, et al. Bioethanol, biohydrogen and biogas production from wheat straw in a biorefinery concept. Bioresour Technol. May 2009;100(9):2562-8. doi: 10.1016/j.biortech.2008.11.011. Epub Jan. 8, 2009.
Katahira, et al, Ethanol fermentation from lignocellulosic hydrolysate by a recombinant xylose- and cellooligosaccharideassimilating assimilating yeast strain, 2006, appl micrbiol biotechnol, 72:1136-1143.
Lu, et al. Hydrolysis of Japanese beech by batch and semi-flow water under subcritical temperatures and pressures. Biomass and Bioenergy, Feb. 2010, pp. 1089-1097.
Maris, et al, Development of Efficient Xylose Fermentation in *Saccharomyces cerevisiae*: Xylose Isomerase as a Key Component, 2007, adv biocehm engin/ biotechnol,108:179-204.
Office action dated Dec. 1, 2016 for U.S. Appl. No. 15/093,698.
Reimann, et al. Element levels in birch and spruce wood ashes—green energy? Science of the Total environment. 2008; 393:191-197.
Sasaki, et al. Dissolution and Hydrolysis of Cellulose in Subcritical and Supercritical Water. Ind. Eng. Chem. Res. 2000, pp. 2883-2890.
Silva, et al, Poly-3-hydroxybutyrate (P3HB) production by bacteria from xylose, glucose and sugarcane bagasse hydrolysate, 2004, J Ind Microbial Biotechnol,31: 245-254.
Standard test method for ash in biomass. ASTM International. Designation E1755. Reapproved Oct. 9, 2015.3 pages.
The use of DOWEX ion exchange resins in corn sweetener processing. The Dow Chemical Company. Published Jun. 2002. 12 pages.
Zhang, et al. Ethanol production from paper sludge by simultaneous saccharification and co-fermentation using recombinant xylose-fermenting microorganisms. Biotechnology and bioengineering. 2010; 107(2):235-244.
Agblevor, et al. Analysis of biomass sugars using a novel HPLC method. Appl Biochem Biotechnol. Mar. 2007;136(3):309-26.
Biology Online. "Oligosaccharide". Downloaded Mar. 27 2017. 1 page.
Co-pending U.S. Appl. No. 15/573,801, filed Nov. 13, 2017.
dictionary.com. "Oligosaccharide". Downloaded Mar. 27, 2017. 2 pages.
Encyclopaedia Britannica. Biochemistry. "Oligosaccharide". Downloaded Mar. 27, 2017. 1 page.
Górecka, et al. The application of ICP-MS and ICP-OES in determination of micronutrients in wood ashes used as soil conditioners. Talanta. Dec. 15, 2006;70(5):950-6.
Kunkes, et al. Catalytic conversion of biomass to monofunctional hydrocarbons and targeted liquid-fuel classes. Science. Oct. 17, 2008;322(5900):417-21. doi: 10.1126/science.1159210. Epub Sep. 18, 2008.
Medical Dictionary: thefreedictionary.com. "Oligosaccharide". Downloaded Mar. 27, 2017. 2 pages.
nutrients review.com. "Oligosaccharides". Downloaded Mar. 27, 2017. 4 pages.
Oxford Dictionary. "Oligosaccharide". Downloaded Mar. 27, 2017. 1 page.
Vassilev, et al. An overview of the chemical composition of biomass. Fuel, vol. 89, Issue 5, May 2010, pp. 913-933. Available online Nov. 10, 2009.
Co-pending U.S. Appl. No. 15/933,210, filed Mar. 22, 2018.
Co-pending U.S. Appl. No. 15/948,837, filed Apr. 9, 2018.
Co-pending U.S. Appl. No. 16/016,467, filed Jun. 22, 2018.
Heinonen, et al. Chromatographic recovery of monosaccharides for the production of bioethanol from wood. Ind. Eng. Chem. Res. 2010; 49:2907-2915.
Michalka, Optimization of Sugar Consumption in the Fermentation of Temulose for Ethanol Production, 2007.
Zhao, et al., Organosolv pretreatment of lignocellulosic biomass for enzymatic hydrolysis, Appl Microbiol Biotechnol (2009) 82:815-827.

* cited by examiner

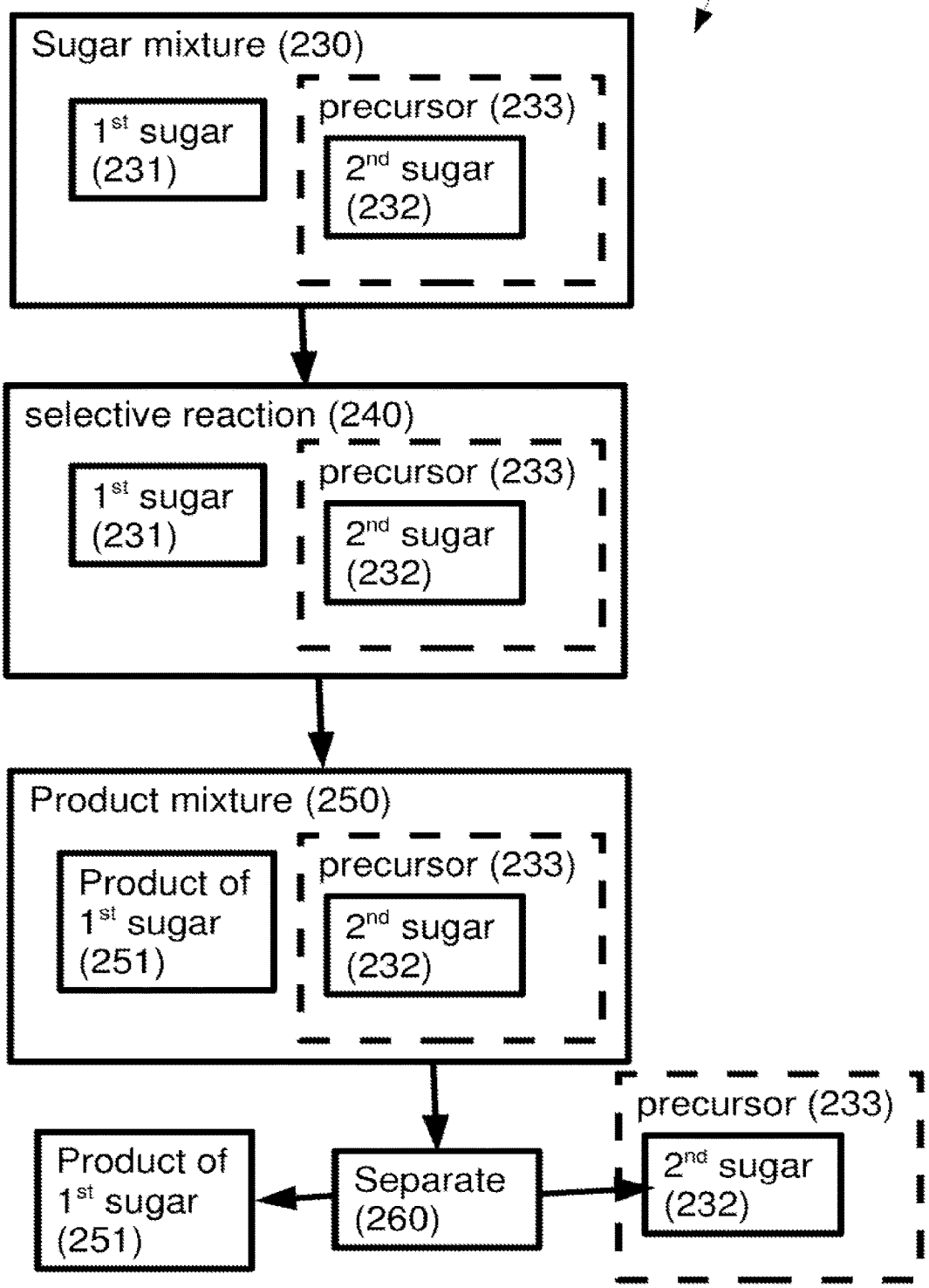

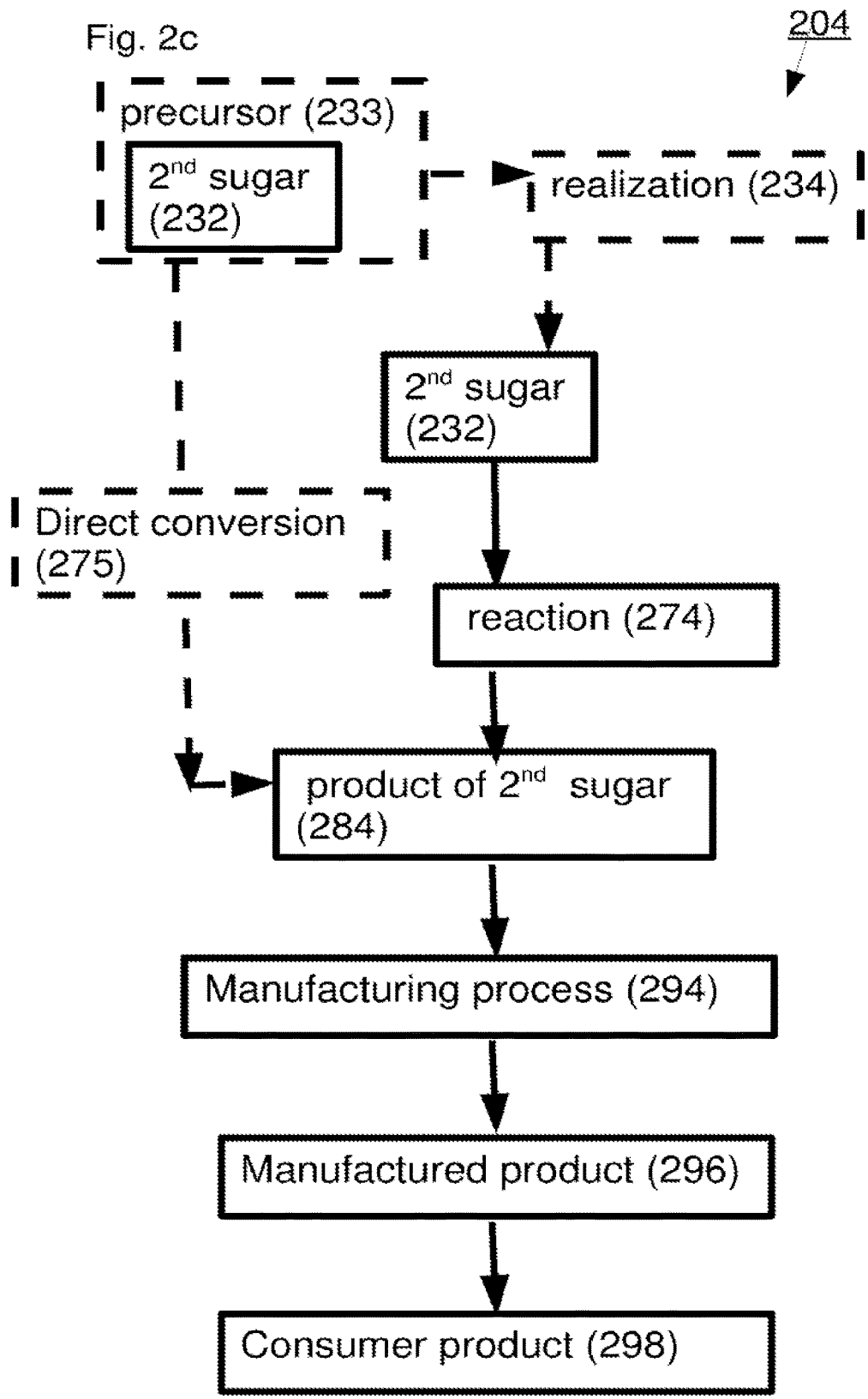

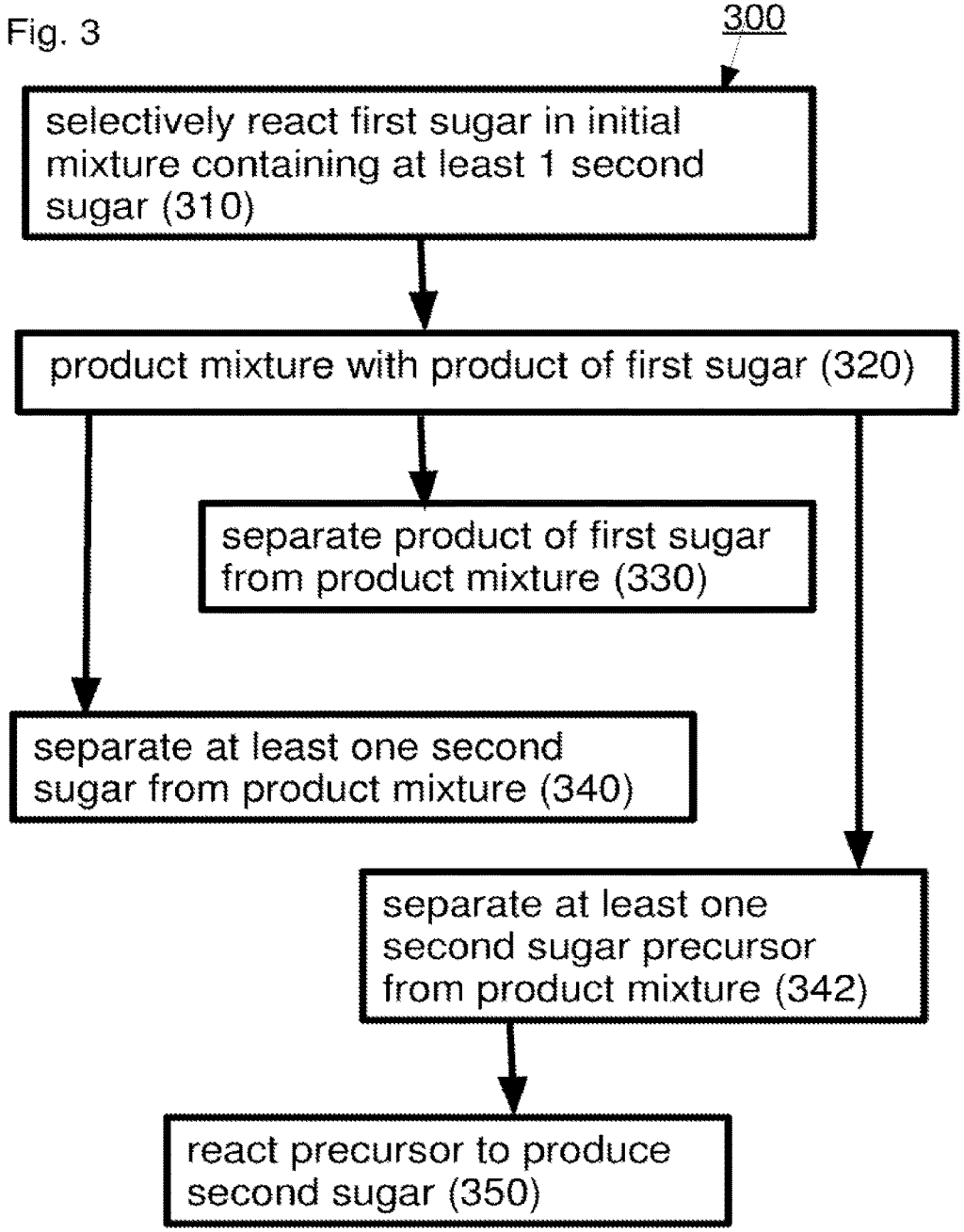

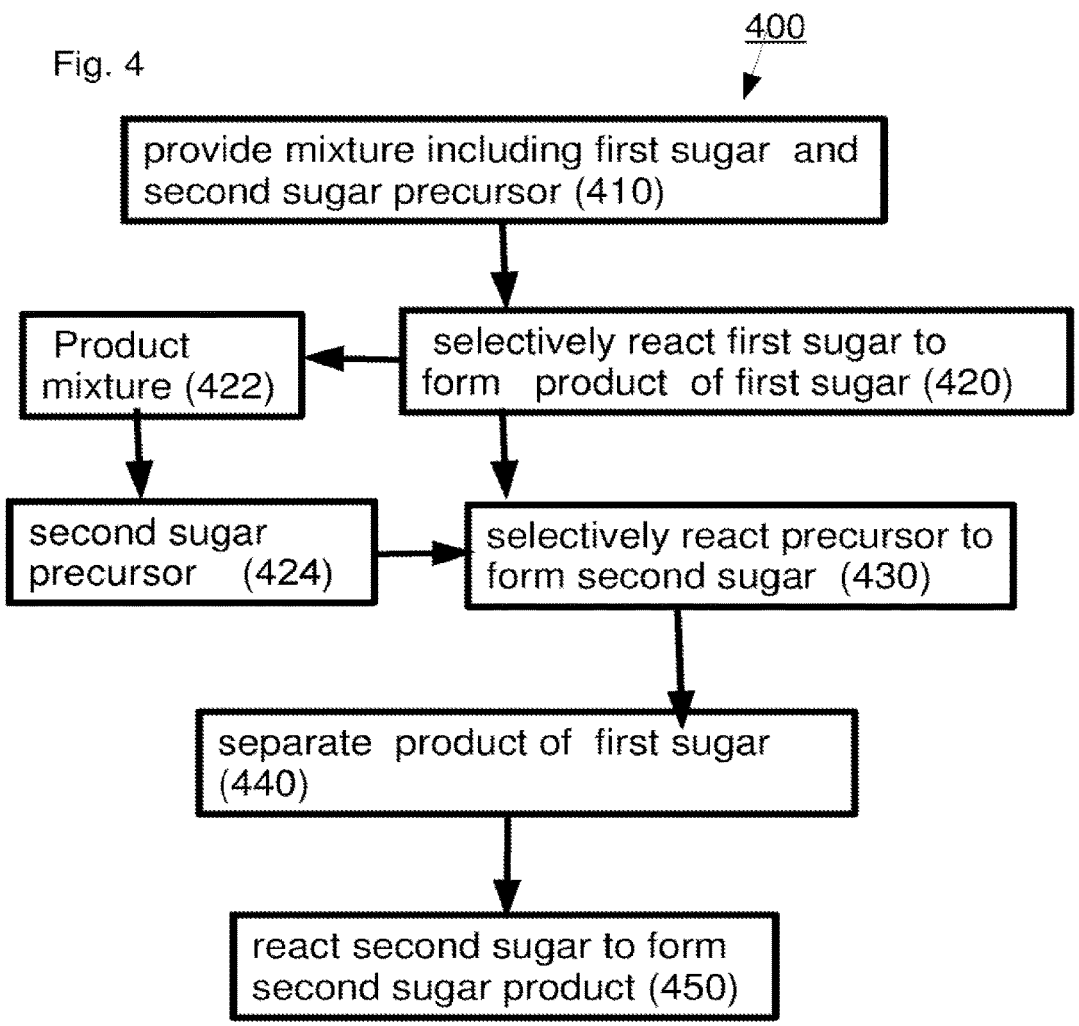

METHODS AND SYSTEMS FOR PROCESSING SUGAR MIXTURES AND RESULTANT COMPOSITIONS

RELATED APPLICATIONS

In accord with the provisions of 35 U.S.C. § 119(a) and/or § 365(b), this application claims priority from:

prior Israeli application IL207945 filed on 2 Sep. 2010 by Robert JANSEN et al. and entitled "Method for the Production of Carbohydrates"; and prior PCT Application IL11/000424 filed on 1 Jun. 2011 by Robert JANSEN et al. and entitled "Lignin Compositions, Systems and Methods for Producing Lignin and/or HCL"; and prior PCT application IL11/000509 filed on Jun. 26, 2011 by Aharon EYAL et al. and entitled "Sugar Mixtures and Methods for Production and Use thereof"; and prior PCT application IL11/000517 filed on Jun. 28, 2011 by Aharon EYAL et al. and entitled "Methods and Systems for Processing a Sucrose Crop and Sugar Mixtures"

prior PCT application US 11/46153 filed on 1 Aug. 2011 by Robert JANSEN et al. and entitled "Methods and Systems for Solvent Purification";

the contents of each of which is fully incorporated herein by reference.

In accord with the provisions of 35 U.S.C. § 119(e) and § 363, this application claims the benefit of:

U.S. 61/529,277 filed on 31 Aug. 2011 by Aharon EYAL et al. and entitled "Methods and Systems for Processing Sugar Mixtures and Resultant Compositions"

the contents of which is fully incorporated herein by reference.

In addition, this application is related to the following applications, each of which is fully incorporated herein by reference:

U.S. 61/483,777 filed on 9 May 2011 by Robert JANSEN et al. and entitled "Hydrolysis Systems and Methods";

U.S. 61/487,319 filed on 18 May 2011 by Robert JANSEN et al. and entitled "Hydrolysis Systems and Methods"; and U.S. 61/524,839 filed on 18 Aug. 2011 by Robert JANSEN et al. and entitled "Systems and Methods for Sugar Refining".

FIELD OF THE INVENTION

This invention relates to processing of sugars.

BACKGROUND OF THE INVENTION

Plants are composed in large part of lignocellulosic material and smaller amounts of lipophilic materials (often referred to as "extractives") and minerals (i.e. ash).

The lignocellulosic material includes lignin, cellulose and hemicellulose.

Cellulose and hemicellulose are each polymeric saccharides (i.e. polysaccharides) of monomeric saccharides (i.e. monosaccharides). Although cellulose and hemicellulose are carbohydrates in a strict chemical sense, the bond types used to connect the monomeric saccharides, and/or the specific monosaccharides in the polymer, make them less physiologically available than other polymeric carbohydrates such as amylan (starch).

Cellulose is rich in six-carbon sugars (hexoses), such as glucose, mannose and galactose. Hemicellulose includes a significant amount of five-carbon sugars (pentoses), such as xylose and arabinose.

Some of these monosaccharides form a large fraction of the total saccharides (e.g. glucose) in the lignocellulosic material, while others are present in relatively low amounts.

Lignocellulosic material is available in a wide variety of forms. In many cases lignocellulosic material is a by-product or waste product. For example, corn stover is a by-product of the corn industry. Alternatively or additionally, the bagasse remaining after initial extraction of sucrose from sugar cane is primarily lignocellulosic. When lignocellulosic material is the by-product, it is often present in a greater quantity by weight than the primary product, as in the case of corn stover and sugar cane bagasse.

In other cases, the primary product is lignocellulosic (e.g. wood produced from timber).

SUMMARY OF THE INVENTION

A broad aspect of the invention relates to sugar processing. More specifically the various exemplary embodiments of the invention described in this application relate to methods of processing a mixture containing more than one sugar.

As used in this specification and the accompanying claims the term "sugar" indicates a monosaccharide or an oligosaccharide containing at least two monosaccharide sub-units and having a solubility greater than 5% in water at 25 degrees centigrade.

In some exemplary embodiments of the invention, one or more of the sugars in the mixture is provided as a "precursor".

As used in this specification and the accompanying claims a "precursor" of a sugar indicates any molecule that can be transformed to the corresponding sugar in one or two chemical reactions. For example, a monosaccharide or an oligosaccharide can be a precursor of another monosaccharide, of a disaccharide or of a longer polysaccharide. For example, glucose can be a precursor of fructose. Alternatively or additionally, an oligosaccharide (e.g. disaccharide) can be a precursor of a different disaccharide or a longer polysaccharide. Alternatively or additionally, esters or ethers of sugars can be precursors of the corresponding sugars.

One aspect of some embodiments of the invention relates to selectively reacting a first sugar in the presence of a second (different) sugar (or a precursor of the second sugar) to form a product mixture including a product produced from the first sugar followed by separating that product from the mixture. In some exemplary embodiments of the invention, the first sugar is glucose and the product produced from the first sugar is ethanol. Optionally, removal of the product produced from the first sugar can be via distillation.

Alternatively or additionally, according to various exemplary embodiments of the invention the selective reaction includes fermentation via a suitable micro-organism for the first sugar in question. In some exemplary embodiments of the invention, selection of a micro-organism with a specific ability to ferment a desired first sugar contributes to selectivity of the reaction.

In some exemplary embodiments of the invention, the second sugar is present as a sugar per se. The second sugar is optionally removed from the reaction mixture as a sugar. Alternatively or additionally, the second sugar is processed to a product produced from the second sugar. According to various exemplary embodiments of the invention, this processing occurs in the mixture or after removal of the second sugar from the mixture.

In some exemplary embodiments of the invention, the product produced from the second sugar is removed from the mixture. Removal techniques for the product include, but are not limited to crystallization, microfiltration and chromatographic separation. Optionally, the product produced from the second sugar is modified to produce a modified product.

In some exemplary embodiments of the invention, the second sugar is present as a sugar precursor. In some exemplary embodiments of the invention, the second sugar precursor is removed from the reaction mixture as a sugar precursor.

In those exemplary embodiments of the invention in which the second sugar is processed to a product produced from the second sugar, this processing can occur in the mixture or after removal of the second sugar from the mixture.

In some exemplary embodiments of the invention, the product produced from the second sugar is removed from the mixture. Removal techniques for the product include, but are not limited to crystallization, microfiltration and chromatographic separation. Optionally, the product produced from the second sugar is modified to produce a modified product.

Another aspect of some exemplary embodiments of the invention relates to increasing a relative concentration of a second sugar in a mixture by removing a first sugar. In some exemplary embodiments of the invention, removal of the first sugar includes conversion of the first sugar to a first sugar product.

Some exemplary embodiments of the invention, relate to preparation of the mixture. Optionally, this preparation includes hydrolysis of a lignocellulosic substrate. In some exemplary embodiments of the invention, this hydrolysis employs a strong acid, for example HCl or $H_2SO_4$. According to various exemplary embodiments of the invention the acid is applied to the substrate at a concentration of 30, 32, 34, 36, 38, 40, 42, 44 or 46%, or intermediate or greater percentages, as calculated by wt of acid/[wt of acid+water].

Some exemplary embodiments of the invention relate to further processing of a product of the first sugar and/or a second sugar to a conversion product.

One aspect of some embodiments of the invention relates to selectively removing at least two monomeric sugars from a sugar mixture containing oligomeric sugars and processing at least a portion of the oligomeric sugars to produce additional monomeric sugars. In some exemplary embodiments of the invention, at least one of the two monomeric sugars is converted to a product and the product is removed from the mixture. Alternatively or additionally, at least one of the two monomeric sugars is crystallized and the crystals are removed from the mixture. In some exemplary embodiments of the invention, processing of the oligomeric sugars includes hydrolysis. Optionally, this hydrolysis is in a dilute acid solution. Optionally, the dilute acid solution includes at least 4, optionally at least 6, optionally at least 9%, or intermediate or greater percentages of acid. Optionally, the dilute acid solution includes less than 15, optionally less than 12, optionally less than 11%, or intermediate or lower percentages of acid. In some exemplary embodiments of the invention, the dilute acid solution includes 4 to 15%, optionally 6 to 12%, optionally 9 to 11% acid. In some exemplary embodiments of the invention, HCl is employed for this hydrolysis.

One aspect of some embodiments of the invention relates to fermentation of glucose in a sugar mixture to produce ethanol and use of at least a portion of the produced ethanol in crystallization of a non-glucose sugar from the mixture. According to various exemplary embodiments of the invention the non-glucose sugar can be monomeric or oligomeric (disaccharide; trisacchararide or longer oligomer). In some exemplary embodiments of the invention, two or more rounds of crystallization are conducted to separate a series of different sugars from the mixture.

Another aspect of some embodiments of the invention relates to a system designed and configured to separate sugars from a mixture using a combination of fermentation to produce an alcohol from one sugar followed by crystallization of at least one additional sugar using the alcohol.

It will be appreciated that the various aspects described above relate to the solution of technical problems associated with harvest of minor components of a mixture in an industrial context.

Alternatively or additionally, it will be appreciated that the various aspects described above relate to the solution of technical problems related to re-arrangement of a sequence of monosaccharide units within an oligosaccharide.

Alternatively or additionally, it will be appreciated that the various aspects described above relate to solution of technical problems related to exploitation of multiple components in a sugar mixture.

In some exemplary embodiments of the invention, there is provided a method including: (a) selectively reacting a first sugar in a mixture which includes at least one second sugar to form a product mixture including a product of the first sugar; (b) separating the product of the first sugar from the product mixture; and (c) separating at least one of the at least one second sugar from the product mixture.

In some exemplary embodiments of the invention, there is provided a method including: (a) selectively reacting a first sugar in a mixture which includes at least one second sugar, to form a product mixture including a product of the first sugar; (b) separating the product of the first sugar from the product mixture; and (c) reacting at least one of the at least one second sugar to form a second sugar product.

In some exemplary embodiments of the invention, there is provided a method including: (a) selectively reacting a first sugar in a mixture which includes at least one second sugar precursor, to form a product mixture including a product of the first sugar; (b) separating the product of the first sugar from the product mixture; and (c) reacting at least one of the at least one second sugar precursor to form a second sugar product.

Optionally, the method includes separating at least one of the at least one second sugar from the product mixture.

Optionally, the method includes separating at least one second sugar product from the product mixture.

Optionally, the first sugar includes glucose and wherein the selectively reacting includes fermenting.

Optionally, the at least one second sugar precursor includes a pentose.

Optionally, the at least one second sugar includes a pentose.

Optionally, the pentose is selected from the group consisting of xylose, xylulose, lyxose, ribulose and arabinose.

Optionally, the at least one second sugar includes a disaccharide.

Optionally, the at least one second sugar precursor includes a disaccharide.

Optionally, the disaccharide is selected from the group consisting of trehalose, gentiobiose, kojibiose, nigerose, sophorose and laminarobiose.

Optionally, the second sugar is xylose.

Optionally, the method includes reacting the second sugar to form a second sugar product.

Optionally, the method includes reacting the second sugar precursor to form a second sugar product.

Optionally, the second sugar is xylose and the second sugar product is selected from xylitol and a rumen bypass protein.

Optionally, the weight ratio between the second sugar to the first sugar prior to the selectively reacting is R1;

the weight ratio between the second sugar to the first sugar in the product mixture is R2; and the ratio of R2 to R1 is greater than 5.

Optionally, the weight ratio between the second sugar precursor to the first sugar prior to the selectively reacting is R1;

the weight ratio between the second sugar precursor to the first sugar in the product mixture is R2; and the ratio of R2 to R1 is greater than 5.

Optionally, the total weight of the second sugar includes at least 50% of the total sugars in the product mixture.

Optionally, the total weight of the second sugar precursor is equal to at least 50% of the total sugars in the product mixture.

Optionally, the product of the first sugar is selected from the group consisting of ethanol, higher alcohols, organic acids and organic acid ester of 3 to 22 carbon atoms, amino acids, yeast and proteins.

Optionally, the separating includes at least one of distillation, membrane filtration, solvent extraction and chromatographic separation.

Optionally, the product of the first sugar has an atmospheric-pressure boiling point of less than 100° C.

Optionally, the product of the first sugar forms an azeotrope with water.

In some exemplary embodiments of the invention, there is provided a method including: (a) providing a mixture including a first sugar and at least one second sugar precursor; (b) selectively reacting the first sugar to form a product mixture including a product of the first sugar; (c) selectively reacting the precursor to form the second sugar; and (d) separating the product of the first sugar.

Optionally, the method includes separating at least one of the at least one second sugar precursor from the product mixture.

Optionally, selectively reacting the precursor to form the second sugar occurs after separating the product of the first sugar.

Optionally, separating the product of the first sugar from the second sugar includes separating each of the product of the first sugar and the second sugar from the product mixture.

Optionally, separating the product of the first sugar is followed by separating the second sugar precursor.

Optionally, separating the product of the first sugar is followed by selectively reacting the precursor to form the second sugar.

Optionally, selectively reacting the precursor includes acid catalysis.

Optionally, selectively reacting the precursor includes enzymatic catalysis.

Optionally, selectively reacting the first sugar includes fermentation.

Optionally, selectively reacting the precursor includes hydrolysis.

Optionally, selectively reacting the precursor includes transglucosidation.

Optionally, selectively reacting the precursor, includes oligomerization.

Optionally, the method includes reacting the second sugar to form a second sugar product.

Optionally, the method includes preparing the mixture.

Optionally, the preparing includes:

providing a lignocellulosic material feed;

hydrolyzing the lignocellulosic material feed to form a hydrolyzate including at least one first sugar and at least one of at least one second sugar and at least one second sugar precursor.

Optionally, the method includes de-acidifying the hydrolyzate.

Optionally, the hydrolyzing is performed in a counter-current mode.

Optionally, the lignocellulosic material feed includes at least 5% hemicellulose.

Optionally, the hydrolyzing employs a hydrolysis medium with a wt/wt ratio of HCl to (HCl+water) of at least 0.35.

Optionally, the de-acidifying includes selective extraction of HCl with an alcohol.

Optionally, an amount of at least one of the at least one second sugars in the mixture, optionally present as a precursor, is at least 85% of a theoretical yield of the same second sugar in the lignocellulosic material feed.

Optionally, the combined concentration of the second sugar and the second sugar precursor in the mixture is C1;

wherein the combined concentration of the second sugar and the second sugar precursor in the product mixture after removal of the first sugar product is C2 and C2/C1 is greater than 1.5.

In some exemplary embodiments of the invention, there is provided a method including: (a) providing a fermentor; and (b) fermenting a medium including a second sugar according as described above in the fermentor to produce a conversion product.

In some exemplary embodiments of the invention, there is provided a method including: (a) providing an input stream including at least one member of the group consisting of:

the second sugars as described above; and the product of the first sugar as described above; and (b) converting at least a portion of the input stream to produce a conversion product.

Optionally, the conversion product includes at least one member selected from the group consisting of alcohols, carboxylic acids, amino acids, monomers for the polymer industry and proteins.

Optionally, the method includes processing the conversion product to produce a consumer product selected from the group consisting of detergent, polyethylene-based products, polypropylene-based products, polyolefin-based products, polylactic acid (polylactide)-based products, polyhydroxyalkanoate-based products and polyacrylic-based products.

Optionally, the detergent includes a sugar-based surfactant, a fatty acid-based surfactant, a fatty alcohol-based surfactant, or a cell-culture derived enzyme.

Optionally, the polyacrylic-based product is selected from plastics, floor polishes, carpets, paints, coatings, adhesives, dispersions, flocculants, elastomers, acrylic glass, absorbent articles, incontinence pads, sanitary napkins, feminine hygiene products, and diapers.

Optionally, the polyolefin-based products are selected from milk jugs, detergent bottles, margarine tubs, garbage containers, water pipes, absorbent articles, diapers, nonwovens, high density polyethylene (HDPE) toys and HDPE detergent packagings.

Optionally, the polypropylene based products are selected from absorbent articles, diapers and non wovens.

Optionally, the polylactic acid based products are selected from packaging of agriculture products and of dairy products, plastic bottles, biodegradable products and disposables.

Optionally, the polyhydroxyalkanoate based products are selected from packaging of agriculture products, plastic bottles, coated papers, molded or extruded articles, feminine hygiene products, tampon applicators, absorbent articles, disposable nonwovens and wipes, medical surgical garments, adhesives, elastomers, films, coatings, aqueous dispersants, fibers, intermediates of pharmaceuticals and binders.

Optionally, the conversion product includes at least one member of the group consisting of ethanol, butanol, isobutanol, a fatty acid, a fatty acid ester, a fatty alcohol and biodiesel.

Optionally, the method includes processing of the conversion product to produce at least one product selected from the group consisting of an isobutene condensation product, jet fuel, gasoline, gasohol, diesel fuel, drop-in fuel, a diesel fuel additive, and a precursor thereof.

Optionally, the gasahol is ethanol-enriched gasoline or butanol-enriched gasoline.

Optionally, the product is selected from the group consisting of diesel fuel, gasoline, jet fuel and drop-in fuels.

In some exemplary embodiments of the invention, there is provided a consumer product, a precursor of a consumer product, or an ingredient of a consumer product produced from a conversion product as described above.

In some exemplary embodiments of the invention, there is provided a consumer product, a precursor of a consumer product, or an ingredient of a consumer product including at least one conversion product produced by a method as described above, wherein the conversion product is selected from carboxylic and fatty acids, dicarboxylic acids, hydroxylcarboxylic acids, hydroxyl di-carboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals.

Optionally, the consumer product is ethanol-enriched gasoline, jet fuel, or biodiesel.

Optionally, the consumer product, a precursor of a consumer product, or an ingredient of a consumer product as described above, wherein the consumer product has a ratio of carbon-14 to carbon-12 of at least about $2.0 \times 10^{-13}$.

In some exemplary embodiments of the invention, relate to a consumer product including an ingredient as described above, and an additional ingredient produced from a raw material other than a lignocellulosic material.

Optionally, the conversion product includes xylitol.

Optionally, the method includes incorporating the xylitol into an edible product.

Optionally, the conversion product includes rumen bypass protein.

Optionally, the method includes incorporating the rumen bypass protein into a livestock feed.

Optionally, the ingredient and the additional ingredient produced from a raw material other than a lignocellulosic material are essentially of the same chemical composition.

Optionally, the consumer product as described above includes a marker molecule at a concentration of at least 100 ppb.

According to various exemplary embodiments of the invention the marker molecule is selected from the group consisting of furfural, hydroxy-methyl furfural, products of furfural or hydroxy-methylfurfural condensation, color compounds formed on heating a sugar, levulinic acid, acetic acid, methanol, galacturonic acid, an alcohol of more than four carbon atoms betaine, amino acids, proteins phosphate and glycerol.

In some exemplary embodiments of the invention, there is provided a method including: (a) selectively reacting a first sugar in an initial mixture which includes at least one oligosaccharide to form a product mixture including a product of the first sugar; (b) producing an oligosaccharide rich sugar fraction with a ratio of at least one of the at least one oligosaccharide to a total sugar concentration greater than a same ratio in the product mixture; and (c) hydrolyzing the oligosaccharide rich sugar fraction to produce monomeric sugars.

Optionally, the first sugar is a monomeric sugar.

Optionally, the initial mixture includes at least one additional monomeric sugar.

In some exemplary embodiments of the invention, there is provided a method including: (a) selectively reacting a first sugar in an initial mixture which includes a first sugar and at least one oligosaccharide to form a product mixture including a product of the first sugar; (b) separating the product of the first sugar from the product mixture; and (c) hydrolyzing the oligosaccharide to produce additional first sugar.

Optionally, the initial mixture includes a second sugar.

Optionally, the method includes separating the second sugar.

Optionally, the method includes separating the product of the first sugar from the product mixture.

Optionally, the method includes separating at least one monomeric sugar from the product mixture.

Optionally, the selectively reacting produces an alcohol.

Optionally, the initial mixture includes a second sugar, and includes use of the alcohol to aid in crystallization of the second sugar.

Optionally, the method includes: distilling the alcohol from the product mixture; and re-introducing the alcohol during the crystallization.

Optionally, the method includes crystallizing the second sugar; and distilling the alcohol from the product mixture.

Optionally, the producing an oligomer rich sugar fraction includes crystallization of at least one of the at least one oligosaccharide from the product mixture.

Optionally, the selectively reacting the first sugar produces an alcohol.

Optionally, the method includes use of the alcohol to aid in the crystallization.

In some exemplary embodiments of the invention, there is provided a method including: (a) fermenting glucose in a portion of an initial mixture which includes at least one additional monomeric sugar and at least one oligosaccharide to form a product mixture including ethanol; and (b) using the ethanol to aid in crystallization of at least one non-glucose sugar in the product mixture.

Optionally, crystallization of at least one non-glucose sugar produces crystals including primarily at least one of the at least one additional monomeric sugar and an oligosaccharide enriched mother liquor.

Optionally, the method includes hydrolyzing the oligosaccharide enriched mother liquor to produce additional monomeric sugars.

Optionally, crystallization of at least one non-glucose sugar produces crystals including primarily at least one of the at least one oligosaccharide and a monomeric sugar enriched mother liquor.

Optionally, the method includes crystallizing at least one monomeric sugar from the monomeric sugar enriched mother liquor.

Optionally, the method includes using ethanol to aid in crystallization of the at least one monomeric sugar.

In some exemplary embodiments of the invention, there is provided a system including: (a) a fermentor adapted to deliver a stream of spent media to a separation unit; (b) the separation unit adapted to separate solids from the spent media and deliver a supernatant stream; (c) a still adapted to distill an alcohol from the supernatant stream to produce a modified supernatant; (d) a primary crystallization module adapted to receive at least a portion of the alcohol from the distillation unit and crystallize at least one sugar from the modified supernatant to produce a mother liquor.

Optionally, the system includes a secondary crystallization module adapted to receive at least a portion of the alcohol from the distillation unit and crystallize at least one additional sugar from the mother liquor to produce a spent mother liquor.

Optionally, the system includes an alcohol recovery module adapted to distill the alcohol from at least one of the mother liquor and the spent mother liquor.

Optionally, the system includes a hydrolysis module adapted to:

receive a material selected from the group consisting of: crystals produced by the primary crystallization module; the mother liquor; crystals produced by the secondary crystallization module and the spent mother liquor; and hydrolyze the received material to produce additional monomeric sugars.

Optionally, the system includes: a recycling module adapted to deliver the additional monomeric sugars to the fermentor.

Optionally, the system includes at least one pump to control flows among and between components of the system.

Optionally, the system includes a controller adapted to control at least one of the at least one pumps.

Optionally, the system includes at least one detector configured to provide data pertaining to at least one system parameter to the controller, wherein the controller is responsive to the data.

In some exemplary embodiments of the invention, there is provided a sugar composition including:

(a) at least 25% xylose by weight relative to total sugar concentration;

(b) at least one alpha-bonded di-glucose; and (c) at least one beta-bonded di-glucose.

Optionally, the alpha-bonded di-glucose includes at least one member of the group consisting of maltose, isomaltose and trehalose.

Optionally, the beta-bonded di-glucose includes at least one member selected from the group consisting of gentiobiose, sophorose and cellobiose.

Optionally, the composition includes at least 40% total sugars.

Optionally, the composition is provided as a solution.

Optionally, the composition includes less than 90% xylose of total sugars on a weight basis.

Optionally, the composition includes glucose between 0.001% and 5% of total sugars on a weight basis.

Optionally, the composition includes at least 0.001% arabinose of total sugars on a weight basis.

Optionally, the composition includes at least 0.001% non-volatile fermentation product on a weight basis.

In some exemplary embodiments of the invention, there is provided a sugar composition including (by weight relative to total sugar concentration):

(a) at least 60% xylose;

(b) at least 100 PPB of a marker molecule; and (c) 0.001% to 10% oligosaccharides.

Optionally, the marker molecule is selected from the group consisting of furfural, hydroxy-methyl furfural, products of furfural or hydroxy-methylfurfural condensation, color compounds formed on heating a sugar, levulinic acid, acetic acid, methanol, galacturonic acid, an alcohol of more than four carbon atoms, betaine, amino acids, proteins phosphate and glycerol.

Optionally, the composition includes at least two marker molecules.

Optionally, the composition includes at least three marker molecules.

Optionally, the composition includes at least one fermentation residue.

Optionally, the at least one fermentation residue is a component of an ingredient selected from the group consisting of sugar molasses, yeast extract and corn steep liquor.

Optionally, the composition includes at least two fermentation residues.

Optionally, the composition includes at least three fermentation residues.

Optionally, the composition includes glucose between 0.001% and 5% of total sugars on a weight basis.

Optionally, the composition includes at least 0.001% arabinose of total sugars on a weight basis.

Optionally, the oligosaccharides include at least one member of the group consisting of maltose, isomaltose and trehalose.

Optionally, the oligosaccharides include at least one member selected from the group consisting of gentiobiose, sophorose and cellobiose.

Optionally, the composition includes at least 0.001% non-volatile fermentation product on a weight basis.

Optionally, a concentration of the marker molecule does not exceed 0.5%.

Optionally, the composition includes at least 60% total sugars.

Optionally, the composition includes at least one sugar selected from the group consisting of mannose, galactose and arabinose.

Optionally, the composition includes at least 3% mannose relative to total monosaccharides by weight.

Optionally, the composition includes at least 5% galactose relative to total monosaccharides by weight.

Optionally, the composition includes at least 2% arabinose relative to total monosaccharides by weight.

In some exemplary embodiments of the invention, there is provided a sugar composition including: (a) at least one of alpha-bonded di-glucose, beta-bonded di-glucose and arabinose; (b) 0.01%-20% xylose by weight relative to total sugar concentration; and (c) at least 100 PPB of a marker molecule.

Optionally, the composition is provided as a solution.

Optionally, the composition includes glucose between 0.001% and 5% (3, 1) of total sugars on a weight basis.

Optionally, the composition includes at least 0.001% non-volatile fermentation product on a weight basis.

Optionally, the alpha-bonded di-glucose includes at least one member of the group consisting of maltose, isomaltose and trehalose.

Optionally, the beta-bonded di-glucose includes at least one member selected from the group consisting of gentiobiose, sophorose and cellobiose.

Optionally, the composition includes at least 40% total sugars.

Optionally, the marker molecule is selected from the group consisting of furfural, hydroxy-methyl furfural, products of furfural or hydroxy-methylfurfural condensation, color compounds formed on heating a sugar, levulinic acid, acetic acid, methanol, galacturonic acid, an alcohol of more than four carbon atoms, betaine, amino acids, proteins phosphate and glycerol.

Optionally, the composition includes at least two marker molecules.

Optionally, the composition includes at least three marker molecules.

Optionally, the composition includes at least one fermentation residue.

Optionally, the at least one fermentation residue is a component of an ingredient selected from the group consisting of sugar molasses, yeast extract and corn steep liquor.

Optionally, a concentration of the marker molecule does not exceed 0.5%.

Optionally, the composition includes a sugar selected from the group consisting of mannose and galactose.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the various embodiments of the invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office.

The term "method" refers to manners, means, techniques and procedures for accomplishing a given task including, but not limited to, those manners, means, techniques and procedures either known to, or readily developed from, known manners, means, techniques and procedures by practitioners of chemistry and/or engineering.

Percentages (%) of chemicals typically supplied as powders or crystals (e.g. sugars) are W/W (weight per weight) unless otherwise indicated. Percentages (%) of chemicals typically supplied as liquids (e.g. alcohols) are W/W (weight per weight) unless otherwise indicated.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale.

In the attached figures:

FIG. 2a is a simplified flow scheme depicting events associated with practice of exemplary methods according to some embodiments of the invention;

FIG. 2c is a simplified flow scheme depicting events associated with practice of exemplary methods according to some embodiments of the invention;

FIG. 3 is a simplified flow diagram of exemplary methods according to some embodiments of the invention;

FIG. 4 is a simplified flow diagram of exemplary methods according to some embodiments of the invention;

DETAILED DESCRIPTION OF EMBODIMENTS

Embodiments of the invention relate to systems and methods for processing mixtures of sugars as well as to modified sugar mixtures found at various stages during this processing. In many exemplary embodiments of the invention, the mixture contains two or more monomeric sugars (e.g. glucose and xylose) and one or more disaccharides or longer oligosaccharide sugars.

Specifically, some embodiments of the invention can be used to process hydrolyzates of lignocellulosic substrates. Optionally, these hydrolyzates result from acid hydrolysis (e.g. with concentrated HCl).

The principles and operation of a system and/or method according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary Source of Sugar Mixtures

Figure 1:
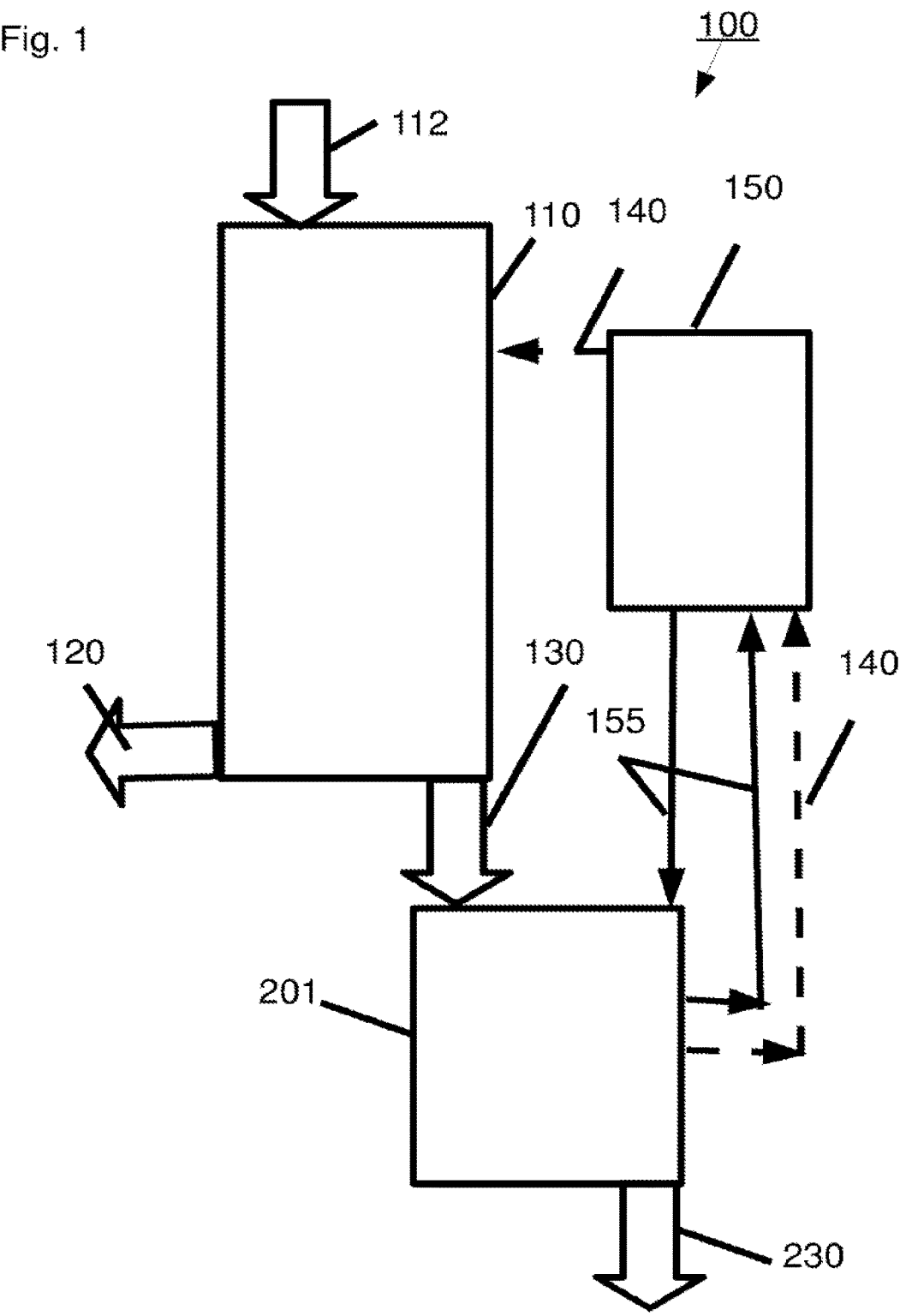
FIG. 1 is a schematic representation of a hydrolysis system which can be used to produce a sugar mixture according to some exemplary embodiments of the invention.

FIG. 1 is a simplified schematic diagram of a system for acid hydrolysis of a lignocellulosic substrate indicated generally as 100. Depicted system 100 includes a main hydrolysis reactor 110 adapted to receive a lignocellulosic substrate input 112. Optionally, substrate 112 is provided as wood chips, although any "woody material" can be used instead of wood. Additional exemplary woody materials include, but are not limited to, sugar cane bagasse, sugar beets and/or their cossettes, corn stover, post harvest plants (e.g. cotton, soybean or rapeseed), switchgrass and broomgrass.

In the depicted exemplary system, substrate 112 is brought into contact with a concentrated HCl solution in reactor 110 and hemicellulose and/or cellulose in the substrate are hydrolyzed to produce a mixture of soluble sugars and residual lignin. These materials are collected separately as lignin stream 120 and sugar mixture 130, each of which contains a large amount of HCl.

Since the acid acts as a catalyst, it is not consumed in the process. In addition, residual acid content of the product and the co-products should be low in order to enable their use. Acid recovery from the hydrolyzate should be conducted under conditions minimizing thermal degradation. Alternatively or additionally, the high concentration of monomeric sugars in the presence of the HCl catalyst can cause re-oligomerization. Cellulose in substrate 112 typically contains primarily beta bonds between the saccharide sub-units of the polymer chain. Dimers and longer oligosaccharides resulting from re-oligomerization can contain alpha bonds.

Details of exemplary hydrolysis methods and systems are described in detail in U.S. provisional applications 61/483,777 and 61/487,319; each of which is fully incorporated herein by reference. According to various exemplary embodiments of the invention the way in which hydrolysis is conducted in reactor 110 contributes to the composition of sugar mixture 130 and/or lignin stream 120. Contribution to the composition of sugar mixture 130 and/or lignin stream 120 may be, for example, a reduction in the amount of sugar degradation products in the mixture and/or an increase in yield of intact pentoses such as xylose.

Sugar mixture 130 is processed to remove HCl and/or adjust the mixture to achieve one or more desired ratios of mixture components (e.g. disaccharides and/or monosaccharides). This processing is conducted in a sugar refining module, designated here generically as 201.

Optionally, additional sugar mixture is recovered from lignin stream 120 as described in co-pending PCT application IL11/000424 which is fully incorporated herein by reference. In some exemplary embodiments of the invention, this additional sugar mixture is routed to refining module 201. According to various exemplary embodiments of the invention this additional sugar mixture increases a total sugar yield and/or changes a composition of the mixture.

In depicted system 100, refining module 201 employs a flow of organic solvent 155 (solid arrows) to extract HCl 140 (dashed arrows) from sugar mixture 130.

De-acidified sugars 230 are the primary product of refining module 201. Module 201 also produces a stream of HCl 140 mixed with solvent 155 (depicted as parallel dashed and solid arrows respectively for clarity) which is routed to a solvent/HCl recovery module 150. Recovery module 150 separates HCl 140 from solvent 155. In some exemplary embodiments of the invention, separation is by distillation.

HCl 140 is recycled to hydrolysis reactor 110 and solvent 155 is recycled to refining module 201.

De-acidified sugars 230 are present as a mixture. Various components of the mixture can be harvested and/or converted as described hereinbelow. Each strategy for harvest and/or conversion of specific sugars and/or sugar products represents an exemplary embodiment of the invention. In some cases, implementation of specific embodiments will be influenced by an initial composition of sugar mixture 230. In many cases, sugar mixture 230 will contain glucose as a primary component since glucose is a primary component of lignocellulosic substrate 112. Alternatively or additionally, in many cases, sugar mixture 230 will contain a significant amount of xylose since xylose is typically the most prevalent saccharide component of hemicellulose in lignocellulosic substrate 112.

Although HCl hydrolysis of substrate 112 is described by way of example, sugar mixtures resulting from other processes are also amenable to use in various exemplary embodiments of the invention. These other processes include any procedure which converts a large portion of the biomass in substrate 112 to soluble sugars. Such procedures include, but are not limited to, enzymatic hydrolysis, hydrolysis with other acids (e.g. $H_2SO_4$) and hydrolysis with "reactive fluids" (e.g. super critical or near critical water) as described in WO 2010/009343; which is fully incorporated herein by reference.

Process Overview

Figure 2B:
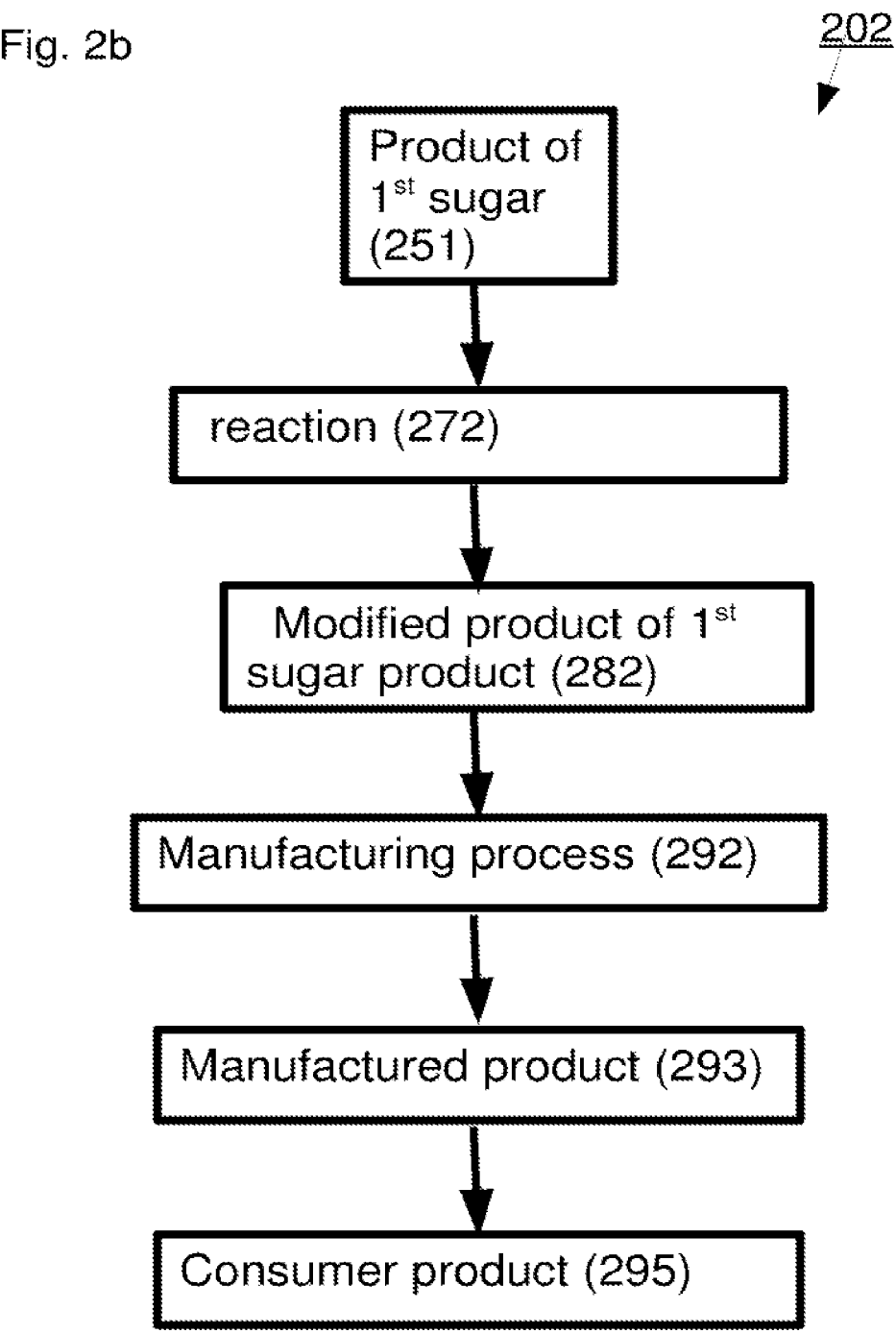
FIG. 2b is a simplified flow scheme depicting events associated with practice of exemplary methods according to some embodiments of the invention.

FIGS. 2a, 2b and 2c are simplified flow schemes depicting events associated with practice of exemplary methods according to various embodiments of the invention.

FIG. 2a is a flow scheme indicated generally as scheme 200 depicting an exemplary sugar mixture 230 (FIG. 1). For simplicity, mixture 230 is depicted as containing a first sugar 231 and a second sugar 232 which is optionally present (at least in part) as a precursor 233. In actuality, mixture 230 typically contains a large number of different sugars, which are not depicted. Each of these different sugars could potentially be treated as a first sugar or a second sugar.

According to scheme 200, mixture 230 is subjected to a selective reaction 240 to produce a product mixture 250. As a result of reaction 240, product mixture 250 includes a product 251 of the first sugar. By way of example, if the first sugar is glucose reaction 240 can be a fermentation reaction (e.g. with yeast or another microorganism capable of using glucose as a substrate) and product 251 can be ethanol and/or yeast. In some exemplary embodiments of the invention, first sugar 231 is substantially completely converted to product 251.

According to depicted flow scheme 200, product 251 is separated 260 from $2^{nd}$ sugar 232 at this stage. Continuing with the example begun above, if product 251 includes ethanol, separation 260 can be by distillation. Alternatively or additionally, if product 251 includes yeast, separation can be via filtration and/or centrifugation. Second sugar 232, optionally as precursor 233 is depicted here alone for clarity but will often be present as part of a mixture similar to mixture 250 except that it has no first sugar product 251.

FIG. 2b is a flow scheme indicated generally as scheme 202 depicting an additional processing of first sugar product 251. According to flow scheme 202, product 251 is subjected to an additional reaction 272. Reaction 272 can be biological or chemical. Since product 251 is provided in isolation, the specificity of reaction 272 is assured. The result of reaction 272 is a modified product 282 of first sugar product 251. Continuing the example begun above, if product 251 is ethanol, modified product 282 may be, for example, ethylene.

According to flow scheme 202, modified product 282 is next subjected to a manufacturing process 292 to produce a manufactured product 293. For example, process 293 could include polymerization of ethylene to polyethylene and formation of a film as manufactured product 293. Optionally, manufactured product 293 could be converted to one or more consumer products 295. In the case of polyethylene, consumer products 295 might include one or more of packaging materials, carrier bags and trash-bags.

It is stressed that the flow scheme of FIGS. 2a and 2b is very versatile, even if only one first sugar is considered. For example, if first sugar 231 is glucose it can be subject to selective reaction 240 in the form of homolactic acid fermentation to produce lactic acid as product 251. In this case, reaction 272 might include polymerization as part of manufacturing process 292 to produce a manufactured product 293 in the form of polylactide (PLA). PLA can be used in a wide variety of consumer products 295 including, but not limited to, woven fabrics with improved ironability, microwavable trays, sutures, stents, dialysis media, drug delivery devices, bioplastics, compost bags, food packaging, disposable tableware, non woven textiles, upholstery, disposable garments, awnings, feminine hygiene products, and diapers.

FIG. 2c is a flow scheme indicated generally as scheme 204 depicting additional processing of second sugar 232 and/or second sugar precursor 233. According to various exemplary embodiments of the invention, portions, optionally all of scheme 204 can be conducted before or after separation 260.

In those exemplary embodiments of the invention, in which second sugar 232 is initially provided as precursor 233, there are two possibilities for scheme 204.

According to the first depicted possibility, $2^{nd}$ sugar 232 is realized 234 from precursor 233.

According to the second possibility, precursor 233 is converted 275 directly to product 284 of second sugar 232.

As used in this specification and the accompanying claims the term "realization" indicates a reaction which has a desired sugar as a product.

Realization 234 can include, for example, a chemical reaction (e.g. hydrolysis, oligomerization) and/or an enzymatic reaction (e.g. transglucosidation, oligomerization). When realization 234 is conducted, $2^{nd}$ sugar 232 is then reacted 274 to produce product 284 of second sugar 232.

Various ways to accomplish realization 234 and/or reaction 274 and/or conversion 275 are described below.

According to depicted exemplary scheme 204, product 284 is subjected to a manufacturing process 294 to produce a manufactured product 296 which can optionally be incorporated into one or more consumer products 298.

For example, if second sugar 232 is xylose, realization 232 can optionally include release of xylose from an oligomeric precursor 233 containing xylose. Optionally, reaction 274 could include hydrogenation to produce xylitol as product 284. According to this exemplary embodiment, manufacturing process 294 might include concentration to produce a product that is 65, optionally 70, optionally 75, optionally 80, optionally 85% or intermediate or greater percentages of total sugars by weight. Optionally, these sugars could be 65, optionally 70, optionally 75, optionally 80, optionally 85% or intermediate or greater percentages of xylose. Optionally, manufacturing process 294 includes crystallization to produce crystals that are 65, optionally 70, optionally 75, optionally 80, optionally 85% or intermediate or greater percentages of xylose as manufactured product 296. In some exemplary embodiments of the invention, these crystals are incorporated into edible products (e.g. chewing gum and/or candy) which serve as consumer products 298.

Exemplary Realization and/or Reaction and/or Direct Conversion

In some exemplary embodiments of the invention, precursor 233 can be an oligosaccharide comprising second sugar 232 (e.g. if second sugar 232 is xylose, precursor 233 can be a xylose-comprising disaccharide or gentiobiose-comprising trisaccharide). In other exemplary embodiments of the invention, second sugar 232 is a disaccharide and/or precursor 233 includes at least two sugars, each of which includes a component of second sugar 232, e.g. as in the case where second sugar 232 is gentiobiose and the precursor includes maltose and/or isomaltose.

According to various exemplary embodiments of the invention realization 234 and/or reaction 274 and/or conversion 275 can each independently include hydrolysis and/or oligomerization, and/or transglucosidation. As used in this specification and the accompanying claims the term "oligomerization" means combining monosaccharides and/or oligosaccharides to form an oligosaccharide of a higher degree of polymerization (e.g. combining two glucose molecules to form sophorose).

As used in this specification and the accompanying claims the term "transglucosidation" means transfer of at least one carbohydrate between oligosaccharides, e.g. as in A-A+B-B  2A-B; or A-A+B-B  A-A-B+B Such reacting of the precursor may comprise a combination, e.g. of hydrolysis followed by oligomerization, as in A-x-A 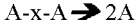 2A 2A  A-y-A where A-x-A and A-y-A are disaccharides composed of the same monosaccharides, but bound by a different bond, e.g. cellobiose and gentiobiose.

Alternatively or additionally, realization 234 and/or reaction 274 and/or conversion 275 can each independently include acid catalysis and/or enzymatic catalysis. Optionally, precursor 233 is catalyzed by HCl. Optionally, temperature influences kinetics of such catalysis. Optionally, the catalysis is enzymatically catalyzed. According to various exemplary embodiments of the invention enzymes such as alpha-glucosidase and/or beta-glucosidase and/or transglucosidases can be employed for this purpose. Optionally, enzymatic catalysis includes fermentation.

According to various exemplary embodiments of the invention realization 234 and/or reaction 274 and/or conversion 275 can each independently include simulated moving bed hydrolysis, sequential simulated moving bed hydrolysis, and ion exchange ISEP® and/or CSEP® (Calgon Carbon Corporation; Pittsburgh, Pa.; USA).

First Exemplary Method

FIG. 3 is a simplified flow diagram of an exemplary method for producing value from at least two sugars from within a complex mixture of sugars, indicated generally as 300. Depicted exemplary method 300, includes selectively reacting 310 a first sugar in an initial mixture which includes at least one second sugar and/or at least one second sugar precursor, to form a product mixture 320 including a product of the first sugar and separating 330 the product of the first sugar from product mixture 320.

Optionally, the first sugar can be glucose; selective reaction 310 can be fermentation with a micro-organism with a strong preference for glucose, to produce ethanol as a product. In this case, separation 330 can be, for example, by distillation of ethanol from product mixture 320.

Alternatively or additionally, the second sugar can be a pentose.

In some exemplary embodiments of the invention, method 300 includes separating 340 at least one of the at least one second sugar from product mixture 320.

Optionally, at least one of said at least one second sugar is at least partly present as a second sugar precursor. In some exemplary embodiments of the invention, method 300 includes separating 342 at least one of the at least one second sugar precursor from product mixture 320. According to these exemplary embodiments of method 300, the method includes reacting 350 the precursor to produce the second sugar.

In other exemplary embodiments of the invention, reacting of the precursor to produce the second sugar occurs in product mixture 320 or in the initial mixture prior to selectively reacting 310 (not depicted).

According to various exemplary embodiments of the invention reacting 350 the precursor includes acid catalysis and/or enzymatic catalysis.

Optionally, the second sugar is reacted to form a second sugar product (not depicted). Alternatively a second sugar precursor can be reacted to form a second sugar product directly without forming the second sugar as an intermediate (not depicted).

In those exemplary embodiments of the invention where the second sugar is xylose the second sugar product can be, for example, xylitol or a rumen bypass protein. Conversion of xylose to xylitol can be, for example, via hydrogenation.

Exemplary Ratios

Method 300 can be conducted with a high degree of efficiency. This efficiency can be expressed as one or more ratios. Optionally, such ratios can be used to characterize additional exemplary embodiments of the invention.

For example, if a weight ratio between the total amount of (second sugar and second sugar precursor) to the first sugar prior to selectively reacting 310 is defined as R1 and a ratio between the total amount of (second sugar and second sugar precursor) to the first sugar in product mixture 320 is defined as R2: in some exemplary embodiments of the invention the ratio of R2 to R1 is optionally greater than 4, optionally greater than 5, optionally greater than 6, optionally greater than 7, optionally greater than 10 or intermediate or larger numbers.

Alternatively or additionally, in some exemplary embodiments of the invention, a total weight of (the second sugar and the second sugar precursor) is at least 40; optionally 50; optionally 60; optionally 70% or intermediate or greater percentages of the total sugars in product mixture 320 by weight.

Exemplary Second Sugars

In some exemplary embodiments of the invention, the second sugar includes a pentose.

Exemplary pentoses include, but are not limited to xylose and/or xylulose and/or lyxose and/or ribulose and/or arabinose. Optionally the second sugar is xylose.

In some exemplary embodiments of the invention, the at least one second sugar includes a disaccharide. Optionally, the disaccharide includes trehalose and/or gentiobiose and/or kojibiose and/or nigerose and/or sophorose and laminaribiose.

Exemplary First Sugar Products

In some exemplary embodiments of the invention, the first sugar product has an atmospheric-pressure boiling point of less than 100° C. Alternatively or additionally, in some exemplary embodiments of the invention, the first sugar product forms an azeotrope with water.

According to various exemplary embodiments of the invention the first sugar product includes an alcohol (e.g. ethanol or a higher alcohol) and/or an organic acid and/or an organic acid ester of 3 to 22 carbon atoms and/or an amino acid and/or yeast and/or a protein. Optionally, a single first sugar (e.g. glucose) can yield more than one first sugar product. For example, yeast and ethanol are two separate products produced when glucose serves as the first sugar and selective reaction 310 includes fermentation with yeast. According to various exemplary embodiments of the invention yeast and ethanol can be removed by different methods (e.g. centrifugation and distillation respectively) and/or at different points in the process (e.g. yeast may be removed prior to separation 340 and/or 342 and ethanol may be removed after separation 340 and/or 342).

Exemplary Separation Methods

According to various exemplary embodiments of the invention each of separation 330, separation 340 and separation 342 can include one or more of distillation, membrane filtration (optionally ultrafiltration), chromatographic separation, crystallization, selective precipitation, centrifugation and solvent extraction. These separation techniques can also be applied to additional separations indicated in other methods hereinbelow.

Second Exemplary Method

FIG. 4 is a simplified flow diagram of an exemplary method for realization of value from a first sugar and a second sugar precursor from within a complex mixture of sugars, indicated generally as 400. Depicted exemplary method 400 includes providing 410 a mixture including a first sugar and at least one second sugar precursor and selectively reacting 420 the first sugar to form a product of the first sugar in product mixture 422. Depicted exemplary method 400 also includes selectively reacting 430 the second sugar precursor 424 to form the second sugar and separating 440 the product of the first sugar. Optionally, second sugar precursor 424 is separated from product mixture 422 prior to selective reaction 430. Alternatively or additionally, in some exemplary embodiments of the invention, selectively reacting precursor 430 occurs after separating 440.

In some exemplary embodiments of the invention, separating 440 includes separating the product of the first sugar and separating the second sugar from product mixture 422.

In other exemplary embodiments of the invention, separating 440 includes separating the product of the first sugar from the reaction mixture followed by separating the second sugar precursor from the mixture prior to the selectively reacting 430 the precursor to form the second sugar.

In other exemplary embodiments of the invention, separating 440 the product of the first sugar is followed by separating second sugar precursor 424 from product mixture 422.

In still other exemplary embodiments of the invention, separating 440 includes separating the product of the first sugar from the mixture followed by selectively reacting the precursor of the second sugar to form the second sugar and separating the second sugar from the mixture.

In some exemplary embodiments of the invention, selectively reacting 420 the first sugar includes fermentation. Alternatively or additionally, in some exemplary embodiments of the invention, selectively reacting 430 the precursor includes hydrolysis, optionally acid hydrolysis and/or enzymatic hydrolysis.

Alternatively or additionally, selectively reacting 430 the precursor includes acid catalysis and/or enzymatic catalysis.

Alternatively or additionally, in some exemplary embodiments of the invention, selectively reacting 430 the precursor includes transglucosidation. Optionally, method 400 includes reacting 450 the second sugar to form a second sugar product.

Alternatively or additionally, selective reaction 430 and/or reaction 450 can include oligomerization. Optionally, combination of catalysis with oligomerization produces a similar oligomer chain but with different bonds between the saccharide links. In some exemplary embodiments of the invention, enzymatic catalysis is via fermentation.

Exemplary Mixture Preparation

Figure 5:
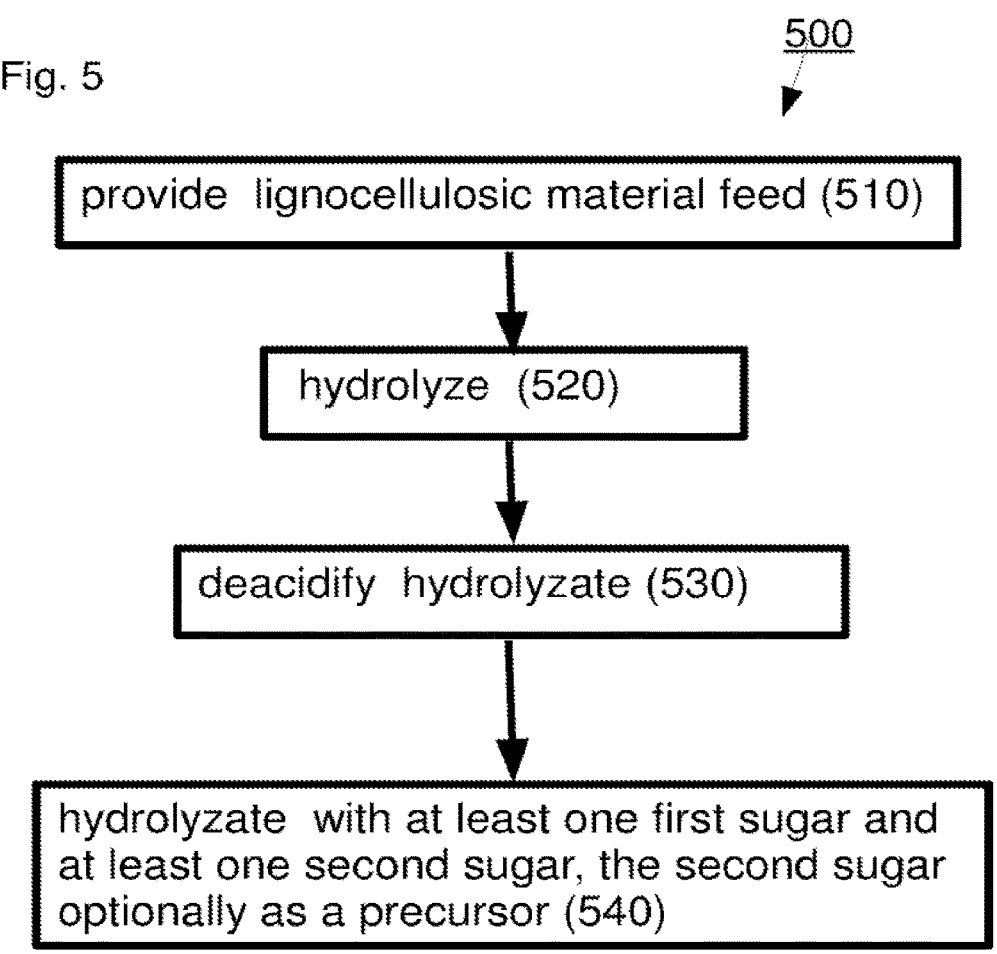
FIG. 5 is a simplified flow diagram of exemplary methods according to some embodiments of the invention.

FIG. 5 is a simplified flow diagram of an exemplary method for preparing a mixture of sugars as described above, indicated generally as 500. Depicted exemplary method 500 includes providing 510 a lignocellulosic material feed, hydrolyzing 520 the lignocellulosic material feed to form a hydrolyzate 540. If the hydrolysis is conducted in an acid, method 500 can included de-acidifying 530 the hydrolyzate. Hydrolyzate 540 includes at least one first sugar and at least one second sugar. Optionally, the second sugar is at least partially present as a precursor and hydrolyzing 520 is performed in a counter-current mode. Optionally, at least 5%, optionally at least 10%, optionally at least 15% or intermediate or greater percentages of said lignocellulosic material feed is hemicellulose.

In some exemplary embodiments of the invention, hydrolyzing 520 employs a hydrolysis medium with a wt/wt ratio of mineral acid to (mineral acid+water) of at least 0.35; optionally at least 0.37; optionally at least 0.39; optionally at least 0.41; optionally at least 0.43; optionally at least 0.45 or intermediate or greater ratios. Exemplary mineral acids include, but are not limited to HCl and $H_2SO_4$.

In other exemplary embodiments of the invention, hydrolyzing 520 employs one or more enzymes to breakdown the lignocellulose provided at 510. According to various exemplary embodiments of the invention the enzymes can be provided as purified enzymes, cellular extracts, cell supernatants, or a culture containing living cells.

In some exemplary embodiments, hydrolysis 520 employs at least one reactive fluid, to produce soluble sugars from the lignocellulose provided at 510.

As used in this specification and the accompanying claims the term "reactive fluid" has the meaning ascribed to it in WO 2010/009343; paragraph [0058]. WO 2010/009343 is fully incorporated herein by reference. Alternatively or additionally, one of ordinary skill in the art will be familiar with the contents of WO 2010/009343.

In some exemplary embodiments of the invention, de-acidifying 530 includes selective extraction of HCl with a first extractant comprising a first solvent (S1) characterized by a water solubility of less than 10% and by at least one of: having a delta-P between 5 and 10 $MPa^{1/2}$; and having a delta-H between 5 and 20 $MPa^{1/2}$, whereupon HCl selectively transfers to the first extractant to form an HCl-carrying first extract and an HCl-depleted aqueous feed.

As used herein Delta-P is the polarity related component of Hoy's cohesion parameter and delta-H is the hydrogen bonding related component of Hoy's cohesion parameter.

The cohesion parameter, or, solubility parameter, was defined by Hildebrand as the square root of the cohesive energy density:

$$\delta = \sqrt{\frac{\Delta E_{vap}}{V}}$$

in which $\Delta$Evap and V are the energy or heat of vaporization and molar volume of the liquid, respectively. Hansen extended the original Hildebrand parameter to three-dimensional cohesion parameter. According to this concept, the total solubility parameter delta is separated into three different components, or, partial solubility parameters relating to the specific intermolecular interactions:

$$\delta^2 = \delta_d^2 + \delta_p^2 + \delta_h^2$$

in which delta-D, delta-P and delta-H are the dispersion, polarity, and Hydrogen bonding components, respectively. Hoy proposed a system to estimate total and partial solubility parameters. The unit used for those parameters is $MPa^{1/2}$. A detailed explanation of that parameter and its components could be found in "CRC Handbook of Solubility Parameters and Other Cohesion Parameters", second edition, pages 122-138. That and other references provide tables with the parameters for many compounds. In addition, methods for calculating those parameters are provided.

In some exemplary embodiments of the invention, de-acidifying 530 includes selective extraction of HCl with an alcohol, optionally hexanol and/or 2-ethylhexanol.

Optionally, an amount of at least one of said at least one second sugars, optionally as a precursor, in the product mixture is at least 80; optionally 85; optionally 90%, or intermediate or greater percentages, of a theoretical yield of the same second sugar in the lignocellulosic material feed provided at 510.

Considering for a moment the concentration of the second sugar and/or its precursor relative to the total amount of sugars present in the mixture, in some cases: if a combined concentration of (the second sugar and its precursor) in the hydrolyzate at 520 is C1 and the combined concentration of (the second sugar and its precursor) in the product mixture 320 after removal of the first sugar product is C2; then C2/C1 is greater than 1.5, optionally greater than 2 and optionally greater than 3. Alternatively or additionally, in some exemplary embodiments of the invention, C2 is at least 30% of saturation concentration at 25° C., optionally at least 50% and optionally at least 70%.

According to various exemplary embodiments of the invention water may be removed at different stages. Optionally, water removal increases a concentration of one or more sugars in the solution. In some exemplary embodiments of the invention, increasing a sugar concentration brings it closer to its saturation point. Optionally, crystallization is more easily accomplished in proximity to the saturation point.

Exemplary Downstream Processing

Figure 6A:
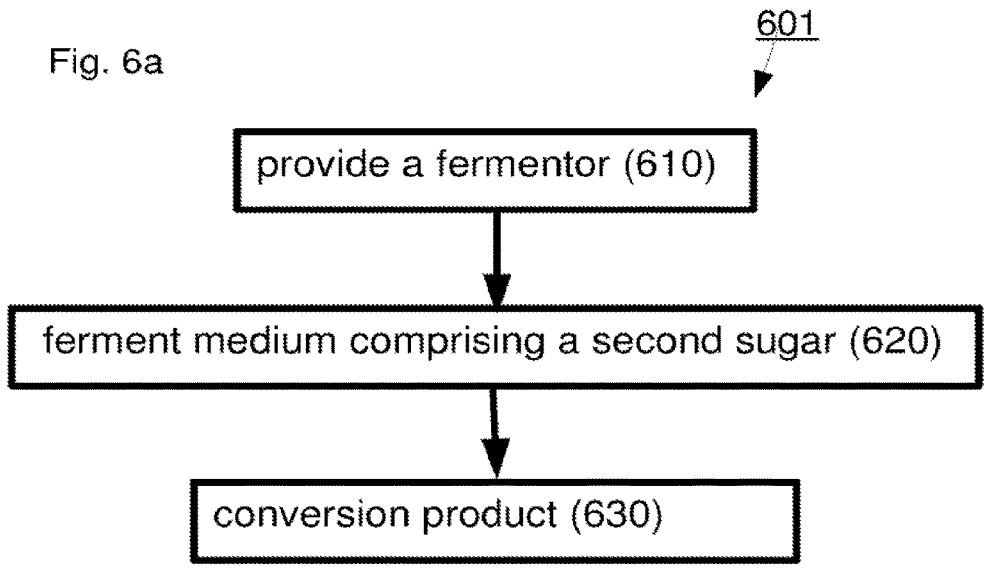
FIG. 6a is a simplified flow diagram of exemplary methods according to some embodiments of the invention.

FIG. 6*a* is a simplified flow diagram of an exemplary method for preparing a conversion product from a second sugar, indicated generally as 601.

Depicted exemplary method 601 includes providing 610 a fermentor and fermenting 620 a medium comprising a second sugar (e.g. 232; 233; 250; 424; or steps 340; 350; 540) the fermentor to produce a conversion product 630.

Figure 6B:
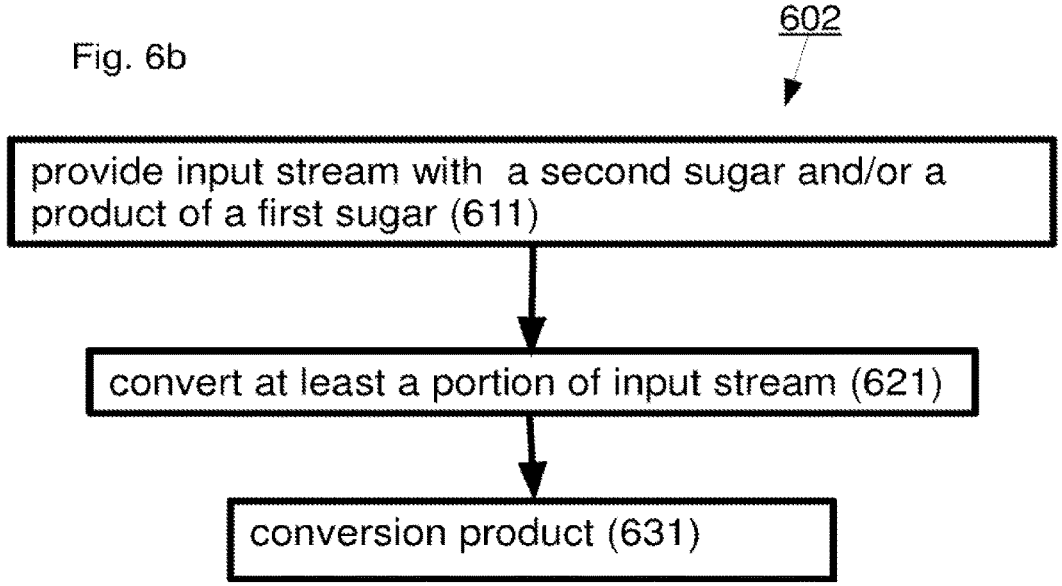
FIG. 6b is a simplified flow diagram of exemplary methods according to some embodiments of the invention.

FIG. 6*b* is a simplified flow diagram of an exemplary method for preparing a conversion product from a second sugar and/or a first sugar product indicated generally as 602.

Depicted exemplary method 602 includes providing an input stream comprising at least one of a second sugar (e.g. 232; 233; 250; 424; or steps 340; 350; 540) and a product of a first sugar (e.g. 251; 422; or step 330) and converting 621 at least a portion of said input stream to produce a conversion product 631.

In some exemplary embodiments of the invention, conversion product 631 includes at least one member selected from the group consisting of alcohols, carboxylic acids, amino acids, monomers for the polymer industry and proteins.

Optionally, the method includes processing conversion product 631 to produce a consumer product such as a detergent, a polyethylene-based product, a polypropylene-based product, a polyolefin-based product, a polylactic acid (polylactide)-based product, a polyhydroxyalkanoate-based product and a polyacrylic-based products.

Optionally, the detergent includes a sugar-based surfactant, a fatty acid-based surfactant, a fatty alcohol-based surfactant, or a cell-culture derived enzyme.

Optionally, the polyacrylic-based product is selected from plastics, floor polishes, carpets, paints, coatings, adhesives, dispersions, flocculants, elastomers, acrylic glass, absorbent articles, incontinence pads, sanitary napkins, feminine hygiene products, and diapers.

Optionally, the polyolefin-based products are selected from milk jugs, detergent bottles, margarine tubs, garbage containers, water pipes, absorbent articles, diapers, non wovens, high density polyethylene (HDPE) toys and HDPE detergent packagings.

Optionally, the polypropylene based products are selected from absorbent articles, diapers and non wovens.

Optionally, the polylactic acid based products are selected from packaging of agriculture products and of dairy products, plastic bottles, biodegradable products and disposables.

Optionally, the polyhydroxyalkanoate based products are selected from packaging of agriculture products, plastic bottles, coated papers, molded or extruded articles, feminine hygiene products, tampon applicators, absorbent articles, disposable nonwovens and wipes, medical surgical garments, adhesives, elastomers, films, coatings, aqueous dispersants, fibers, intermediates of pharmaceuticals and binders.

In some exemplary embodiments of the invention, conversion product 631 includes at least one member of the group consisting of ethanol, butanol, isobutanol, a fatty acid, a fatty acid ester, a fatty alcohol and biodiesel.

In some exemplary embodiments of the invention, the method includes processing of conversion product 631 to produce at least one product selected from the group consisting of an isobutene condensation product, jet fuel, gasoline, gasohol, diesel fuel, drop-in fuel, diesel fuel additive, and a precursor thereof.

Optionally, the gasahol is ethanol-enriched gasoline or butanol-enriched gasoline.

Optionally, the product is selected from the group consisting of diesel fuel, gasoline, jet fuel and drop-in fuels. US patent application publication 2009/0035842 describes technology relevant to these applications and is fully incorporated herein by reference.

Some exemplary embodiments of the invention relate to a consumer product, a precursor of a consumer product, or an ingredient of a consumer product produced from a conversion product 631.

Optionally, the consumer product, precursor of a consumer product, or ingredient of a consumer product includes a conversion product 631 selected from carboxylic and fatty acids, dicarboxylic acids, hydroxylcarboxylic acids, hydroxyl di-carboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals.

Optionally, the product is ethanol-enriched gasoline, jet fuel, or biodiesel.

Optionally, the consumer product, precursor of a consumer product, or ingredient of a consumer product has a ratio of carbon-14 to carbon-12 of about $2.0 \times 10^{-13}$ or greater.

In some exemplary embodiments of the invention, the consumer product includes an ingredient and an additional ingredient produced from a raw material other than lignocellulosic material. Optionally, the ingredient and said additional ingredient produced from a raw material other than lignocellulosic material are essentially of the same chemical composition.

Optionally, the consumer product includes a marker molecule at a concentration of at least 100 ppb. Marker molecules suitable for use in this context include, but are not limited to, furfural, hydroxy-methyl furfural, products of furfural or hydroxy-methylfurfural condensation, color compounds derived from sugar carmelization, levulinic acid, acetic acid, methanol, galacturonic acid, and glycerol.

In some exemplary embodiments of the invention, conversion product 631 includes xylitol. In some exemplary embodiments of the invention, method 601 and/or 602 includes incorporating the xylitol into an edible product. Edible products include, but are not limited to chewing gum, candy, energy bars, energy gels, energy drinks, cookies and other food products.

In some exemplary embodiments of the invention, conversion product 631 includes rumen bypass protein. In some exemplary embodiments of the invention, method 601 and/ or 602 includes incorporating the rumen bypass protein into a livestock feed. Livestock feeds include, but are not limited to hay, straw, silage compressed feed, pelleted feed, oils, mixed rations and crumbled pellets.

Additional Exemplary Method

Figure 7A:
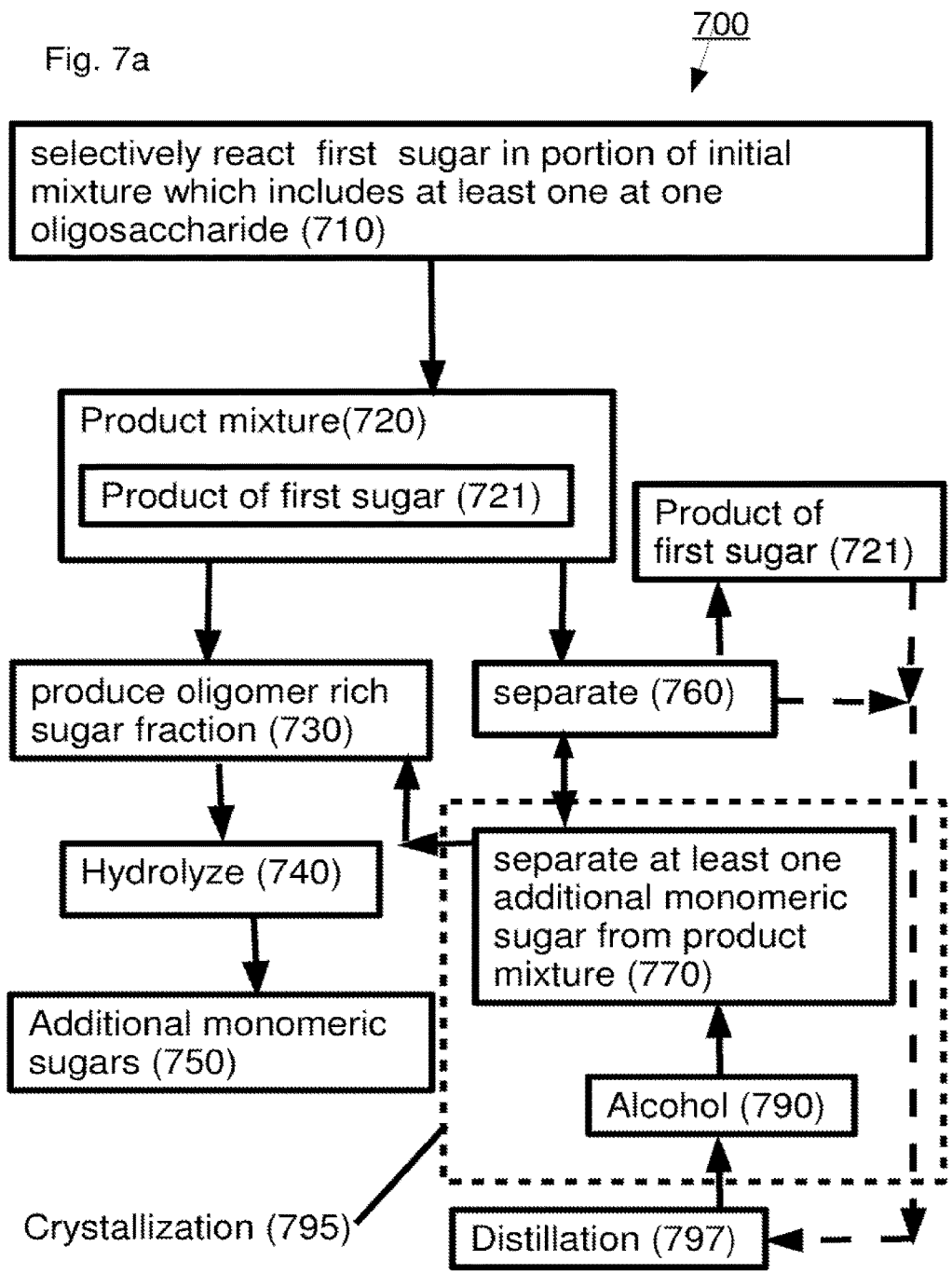
FIG. 7a is a simplified flow diagram of exemplary methods according to some embodiments of the invention.

FIG. 7a is a simplified flow diagram of an exemplary method for recovering sugars (optionally monomeric sugars) and/or their products from a complex sugar mixture including oligosaccharides, indicated generally as 700.

Depicted exemplary method 700 includes selectively reacting 710 a first sugar in a portion of an initial mixture which includes and at least one oligosaccharide to form a product mixture 720 comprising a product 721 of the first sugar. Optionally, the initial mixture includes one or more monomeric sugars. Depicted exemplary method 700 also includes producing 730 an oligomer rich sugar fraction with a ratio of at least one of said at least one oligosaccharide to a total sugar concentration greater than a ratio of the same components in product mixture 720. Optionally, method 700 includes hydrolyzing 740 the oligomer rich sugar fraction to produce additional monomeric sugars 750. Exemplary ways to perform hydrolysis 740 are described in provisional patent application U.S. 61/524,839 which is fully incorporated herein by reference.

Depicted exemplary method 700 includes separating 760 product 721 of the first sugar from product mixture 720.

Optionally, method 700 includes separating 770 at least one of the at least one additional monomeric sugars from product mixture 720. In some exemplary embodiments of the invention, separation 770 includes crystallization. Optionally, xylose is crystallized during separation 770.

In some exemplary embodiments of the invention, selectively reacting 710 the first monomeric sugar yields an alcohol 790 as a reaction product. Optionally, the first monomeric sugar is glucose and the alcohol includes ethanol.

In the depicted exemplary embodiment, method 700 includes use of alcohol 790 to aid in crystallization 795 of at least one of said at least one additional monomeric sugars. In some exemplary embodiments of the invention, the monomeric sugar to be crystallized is xylose. In some exemplary embodiments of the invention, separation 770 includes removal of water to increases a concentration of each sugar in the mixture. Alternatively or additionally, separation 770 includes addition of alcohol 790 at a higher concentration than that which was present in the mixture prior to separation 760 by distillation 797. Optionally, separation 770 by crystallization employs alcohol 790 at a concentration of 15; 20; 25; 30; 35; 40; 45; 50; 55; 60; 65; 70; 75; 80; 85; 90% or intermediate concentrations (W/W).

In some exemplary embodiments of the invention, alcohol 790 is distilled 797 from product mixture 720 as a means of separation 760 of product 721 and re-introduced during crystallization 795 at a desired concentration. Optionally, these embodiments include a repetition of separation 760 (indicated by double headed arrow) to recover alcohol 790. These embodiments are advantageous in that they can achieve a high alcohol concentration which makes it feasible to crystallize sugars that are relatively far from their saturation point. However, there is an energy cost to re-distilling the alcohol for recovery.

In other exemplary embodiments of the invention (not depicted), separation 770 by crystallizing 795 at least one of the at least one additional monomeric sugars is followed by distilling 797 of alcohol 790 from the product mixture. These embodiments are advantageous in that they involve only a single distillation, but cannot achieve the high alcohol concentrations during crystallization which are possible if distillation is conducted prior to crystallization unless alcohol is introduced from an outside source, or from a previous round of purification.

In some exemplary embodiments of the invention, producing 730 an oligomer rich sugar fraction includes crystallization 795 of at least one of said at least one oligosaccharide from product mixture 720. Optionally, this crystallization employs an alcohol 790 produced by selectively reacting 710. Alcohol 790 can be used to aid in crystallization of an oligosaccharide as described above for monomeric sugars.

According to various exemplary embodiments of the invention separation 770 produces either crystals of oligosaccharide, or a liquid mixture enriched in oligosaccharides. In either case, these oligomeric sugars can be used to produce 730 the oligomer rich sugar fraction which can subsequently be hydrolyzed 740 to produce additional monomeric sugars.

Figure 7B:
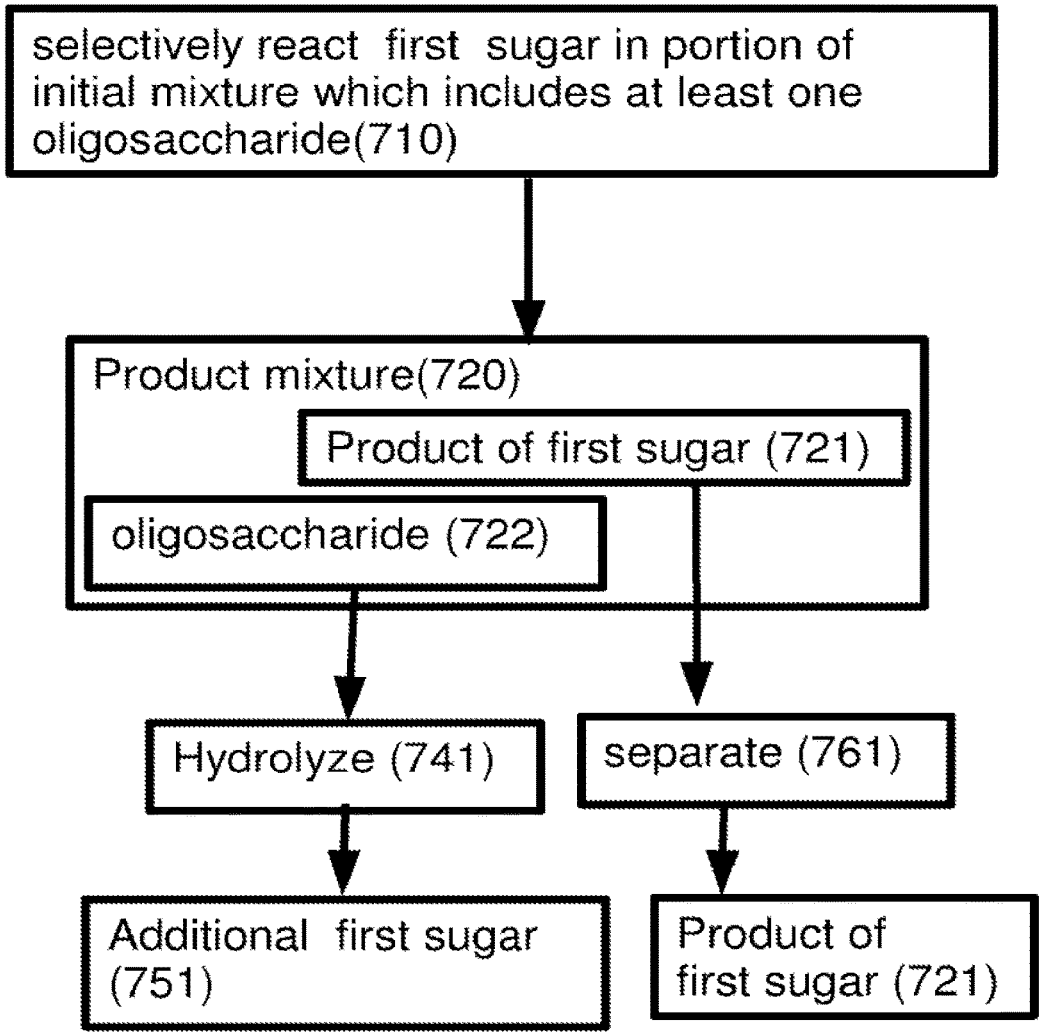
FIG. 7b is a simplified flow diagram of exemplary methods according to some embodiments of the invention.

FIG. 7b is a simplified flow diagram of another exemplary method for recovering sugars (optionally monomeric sugars) and/or their products from a complex sugar mixture including oligosaccharides, indicated generally as 701.

Depicted Exemplary method 701 includes selectively reacting 710 a first sugar in an initial mixture which includes a first sugar and at least one oligosaccharide 722 to form a product mixture 720 comprising a product 721 of the first sugar. Depicted method 701 also includes separating 761 product 721 from product mixture 720 and hydrolyzing 741 oligosaccharide 722 to produce additional first sugar 751.

Optionally, the initial mixture includes a second sugar. In some exemplary embodiments of the invention, the method includes separating the second sugar.

Another Additional Exemplary Method

Figure 8A:
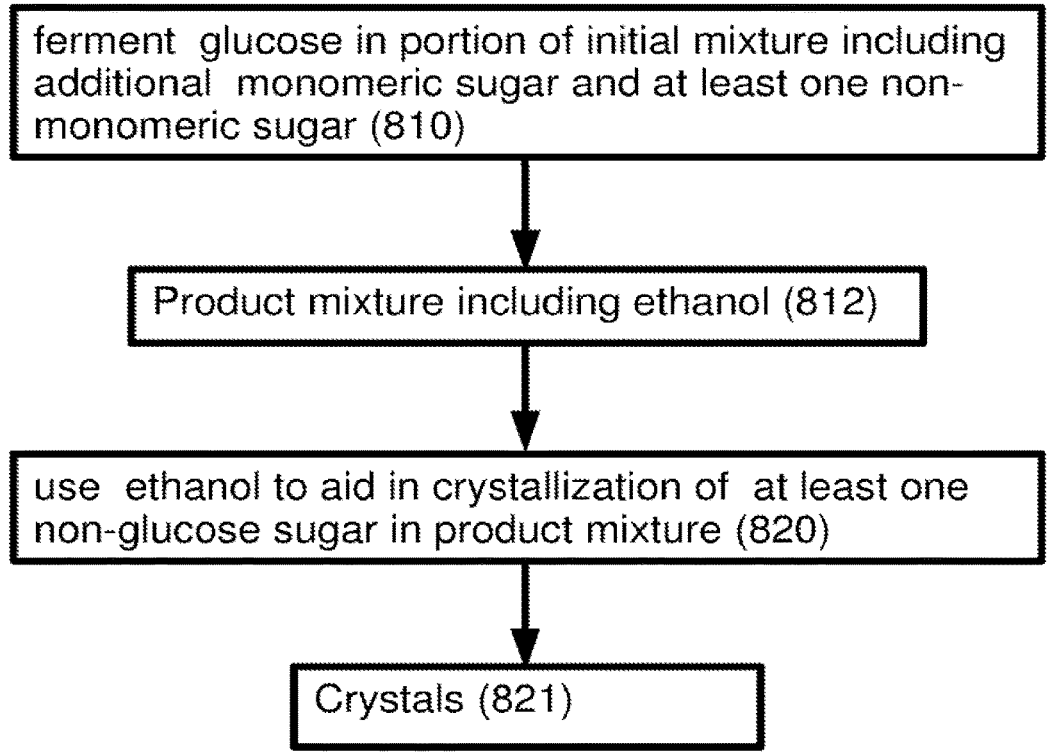
FIG. 8a is a simplified flow diagram of exemplary methods according to some embodiments of the invention.

FIG. 8a is a simplified flow diagram of an exemplary method for recovering ethanol and a crystallized non-glucose sugar from a complex sugar mixture including oligosaccharides, indicated generally as 801.

Depicted exemplary method 801 includes fermenting 810 glucose in a portion of an initial mixture which includes at least one additional monomeric sugar and at least one oligosaccharide to form a product mixture 812 including ethanol and using 820 the ethanol to aid in crystallization of at least one non-glucose sugar in the product mixture to produce crystals 821. Optionally, the non-glucose sugar is xylose.

Figure 8B:
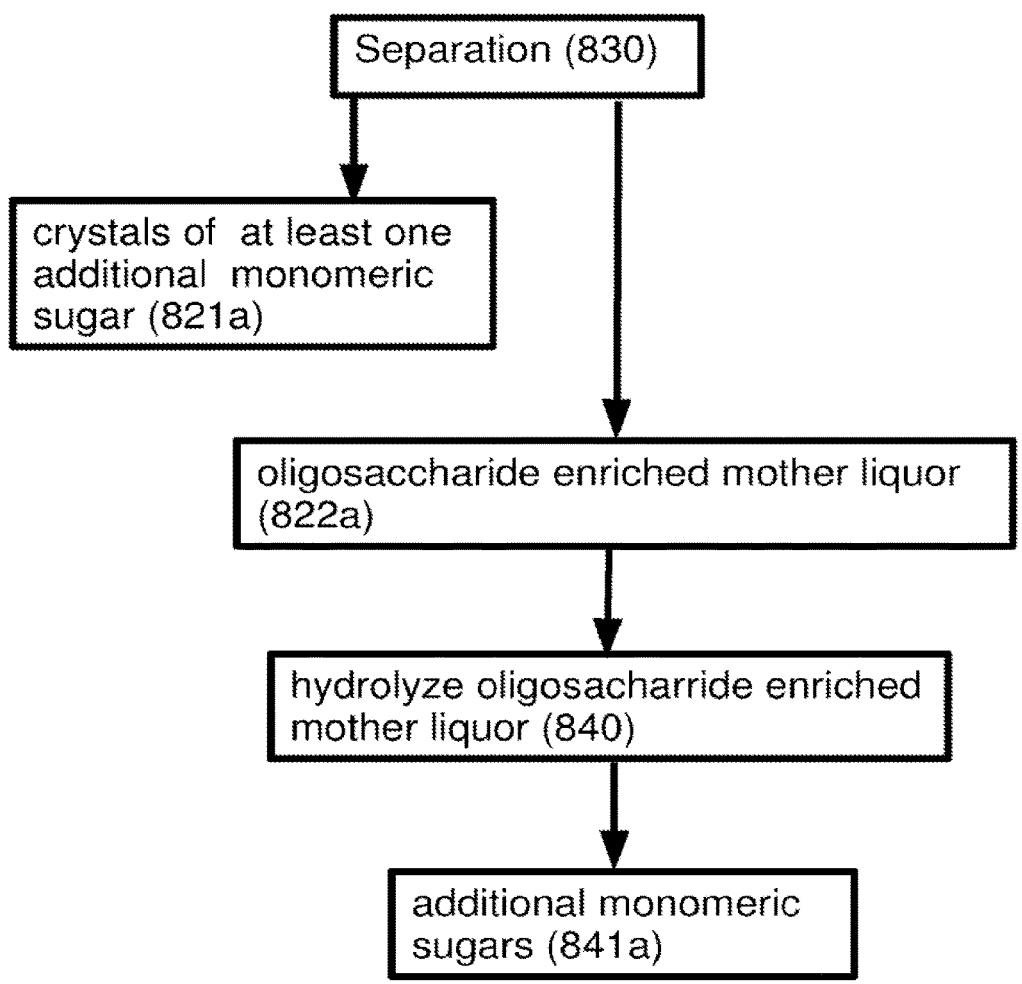
FIG. 8b is a simplified flow diagram of exemplary methods according to some embodiments of the invention.

FIG. 8b is a simplified flow diagram of an exemplary method according to FIG. 8a in which crystals 821 are monomeric sugar crystals indicated generally as method 802.

Depicted exemplary method 802 begins with separation 830 of at least one non-glucose sugar as crystals 821a comprising primarily at least one of the at least one additional monomeric sugar and an oligosaccharide enriched mother liquor 822a.

Optionally, method 802 includes hydrolyzing 840 oligosaccharide enriched mother liquor 822a to produce additional monomeric sugars 841a.

Figure 8C:
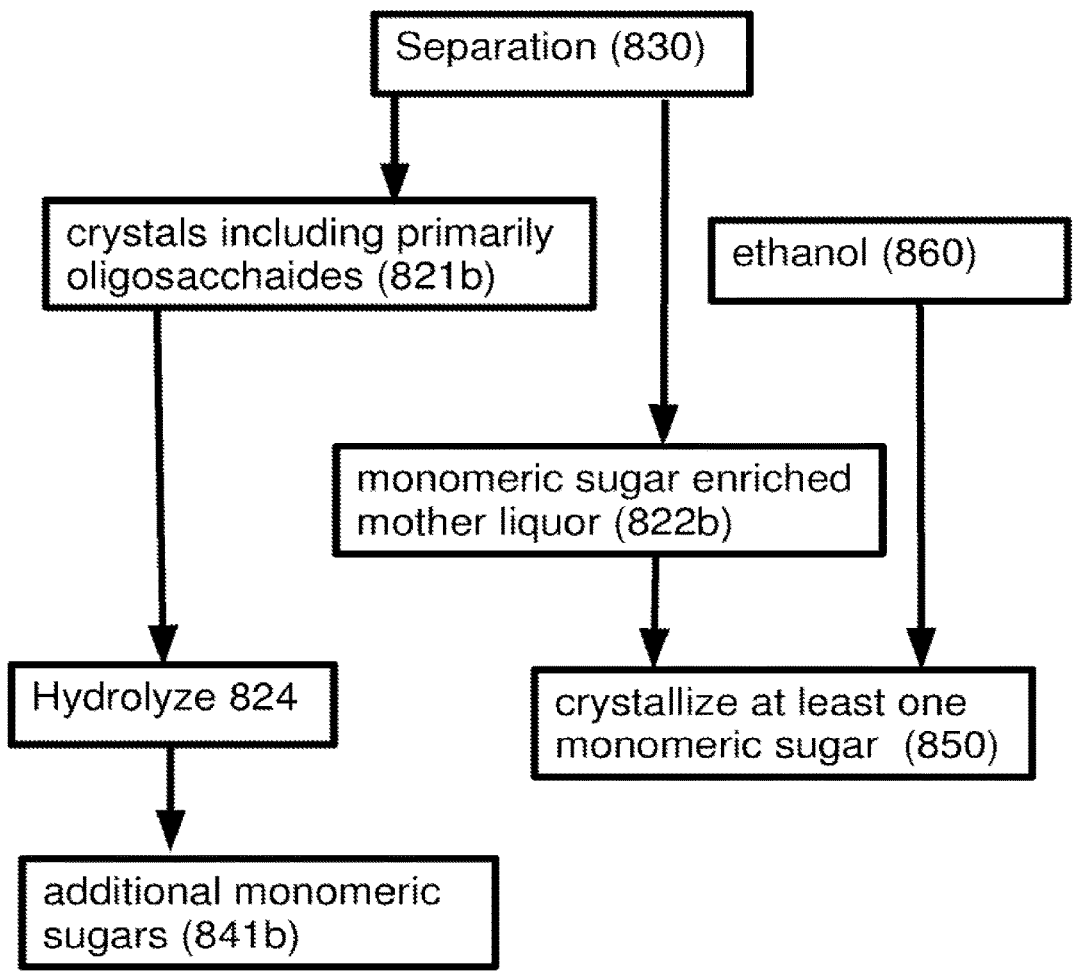
FIG. 8c is a simplified flow diagram of exemplary methods according to some embodiments of the invention.

FIG. 8c is a simplified flow diagram of an exemplary method according to FIG. 8a in which crystals 821 are oligosaccharide crystals indicated generally as method 804.

Depicted exemplary method 804 begins with separation 830 of crystals 821b comprising primarily one or more oligosaccharides and a monomeric sugar enriched mother liquor 822b.

In the depicted embodiment, method 804 includes crystallizing 850 at least one monomeric sugar from monomeric sugar enriched mother liquor 822b. Optionally, an alcohol, such as ethanol 860 is used to aid in crystallization 850.

In some exemplary embodiments of the invention, crystals 821b are hydrolyzed 824 to produce additional monomeric sugars 841b. In some exemplary embodiments of the invention, these additional monomeric sugars include glucose.

Exemplary System

Figure 9:
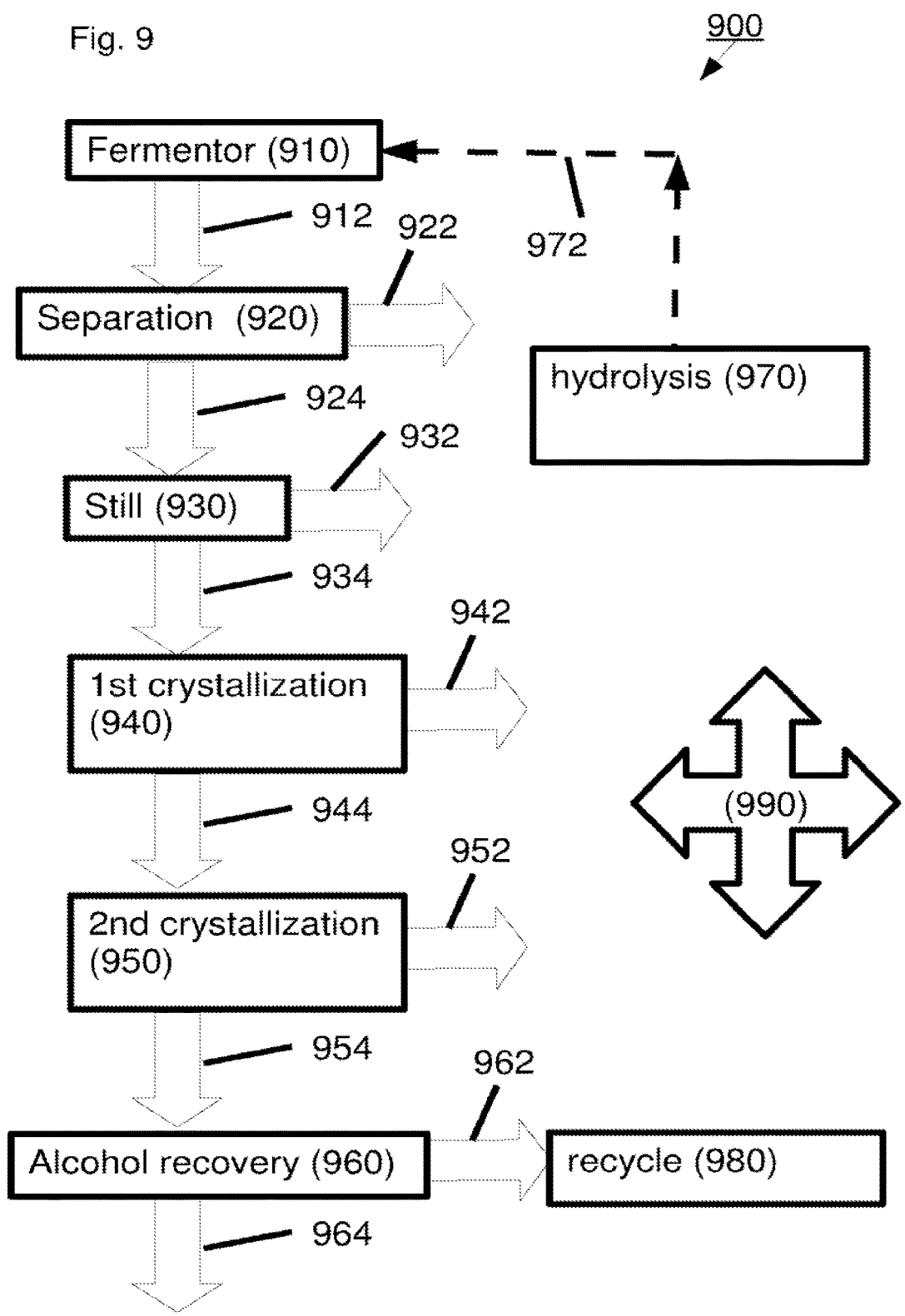
FIG. 9 is a schematic representation of an exemplary system according to some embodiments of the invention.

FIG. 9 is schematic diagram of an exemplary system for processing a sugar mixture indicated generally system 900. Depicted exemplary system 900 includes a fermentor 910 adapted to deliver a stream of spent media 912 to a separation unit 920 adapted to separate solids 922 from spent media 912 and deliver a supernatant stream 924. According to various exemplary embodiments of the invention separation unit 920 includes centrifugation components and/or filtration components.

Depicted exemplary system 900 also includes a distillation unit 930 adapted to distill an alcohol 932 from supernatant stream 924 to produce a modified supernatant 934. Adaptation to distill an alcohol can include implementation of one or more design changes which take into account the alcohol to be distilled and/or the composition of supernatant stream 924. For example, if the alcohol to be distilled has a high boiling point, a stronger heat source may be provided. Alternatively or additionally, if there are components in stream 924 with a boiling pint close to that of the alcohol in question, a long distillation column, or two or more distillation columns in series, may be incorporated into distillation unit 930 to improve separation of the alcohol from other components. In some exemplary embodiments of the invention, the alcohol is ethanol which can be recovered at up to 95% purity.

Depicted exemplary system 900 also includes a primary crystallization module 940 adapted to receive at least a portion of modified supernatant 934 from distillation unit 930 and crystallize at least one sugar (crystals 942) therefrom to produce a mother liquor 944. Optionally, distillation unit 930 also delivers at least a portion of alcohol 932 to crystallization module 940. Alternatively or additionally, crystallization module 940 receives alcohol from an independently provided alcohol reservoir (not depicted). Optionally, separation of alcohol 932 from stream 934 followed by re-mixing of these components contributes to an ability to increase the alcohol concentration in stream 934. In some exemplary embodiments of the invention, increasing the alcohol concentration improves one or more crystallization parameters. Crystallization parameters include, but are not limited to, yield and purity of crystals. Alcohol concentrations during crystallization are optionally as described above in the context of FIG. 7*a*.

In some exemplary embodiments of the invention, fermentor 910 converts glucose to ethanol which is distilled by distillation unit 930 so that modified supernatant 934 is substantially free of glucose. According to these exemplary embodiments of the invention crystals 942 are of a non-glucose sugar. According to various exemplary embodiments of the invention this sugar can be monomeric or oligomeric (e.g. disaccharide or higher).

Optionally, system 900 includes a secondary crystallization module 950 adapted to receive at least a portion of alcohol 932 from distillation unit 930 and crystallize at least one additional sugar (crystals 952) from mother liquor 944 to produce a spent mother liquor 954. Optionally, alcohol aids in crystallization as described above in the context of module 940. Alternatively or additionally, secondary crystallization module 950 receives alcohol from an independently provided alcohol reservoir (not depicted).

Depicted exemplary system 900 also includes an alcohol recovery module 960 adapted to distill alcohol 962 from mother liquor 944 and/or spent mother liquor 954. Module 960 also produces a liquor residue 964. In some exemplary embodiments of the invention, residue 964 is subject to anaerobic fermentation in an anaerobic fermentation module (not depicted). Optionally, this anaerobic fermentation produces a usable energy source such as methane. In some exemplary embodiments of the invention, methane produced in this manner is used to provide heat energy for various system components (e.g. distillation module 930 and/or alcohol recovery module 960).

In some exemplary embodiments of the invention, exemplary system 900 also includes a hydrolysis module 970. Hydrolysis module 970 produces additional monomeric sugars 972 from an input material including dimeric sugars and other soluble oligomeric sugars. According to various exemplary embodiments of the invention the input material includes one or more of crystals 942 produced by primary crystallization module 940; mother liquor 944; crystals 952 produced by secondary crystallization module 950 and spent mother liquor 954. Optionally, additional monomeric sugars 972 are delivered to fermentor 910 (as depicted) and/or to crystallization module 940 and/or 950 (not shown) by a recycling pump (not depicted).

According to various exemplary embodiments of the invention system 900 includes one or more pumps (not depicted) to control flows among and between components of the system.

Depicted exemplary system 900 includes a controller 990 adapted to control at least one of the at least one pumps. Optionally, system 900 includes one or more detectors (not shown) configured to provide data pertaining to at least one system parameter to controller 990. In some exemplary embodiments of the invention, controller 990 is responsive to the data. System parameters include, but are not limited to, concentration of specific sugars at specific points, total sugar concentration at specific points, alcohol concentration, temperatures, flow rates and acid concentration.

Additional Exemplary Method

Figure 10:
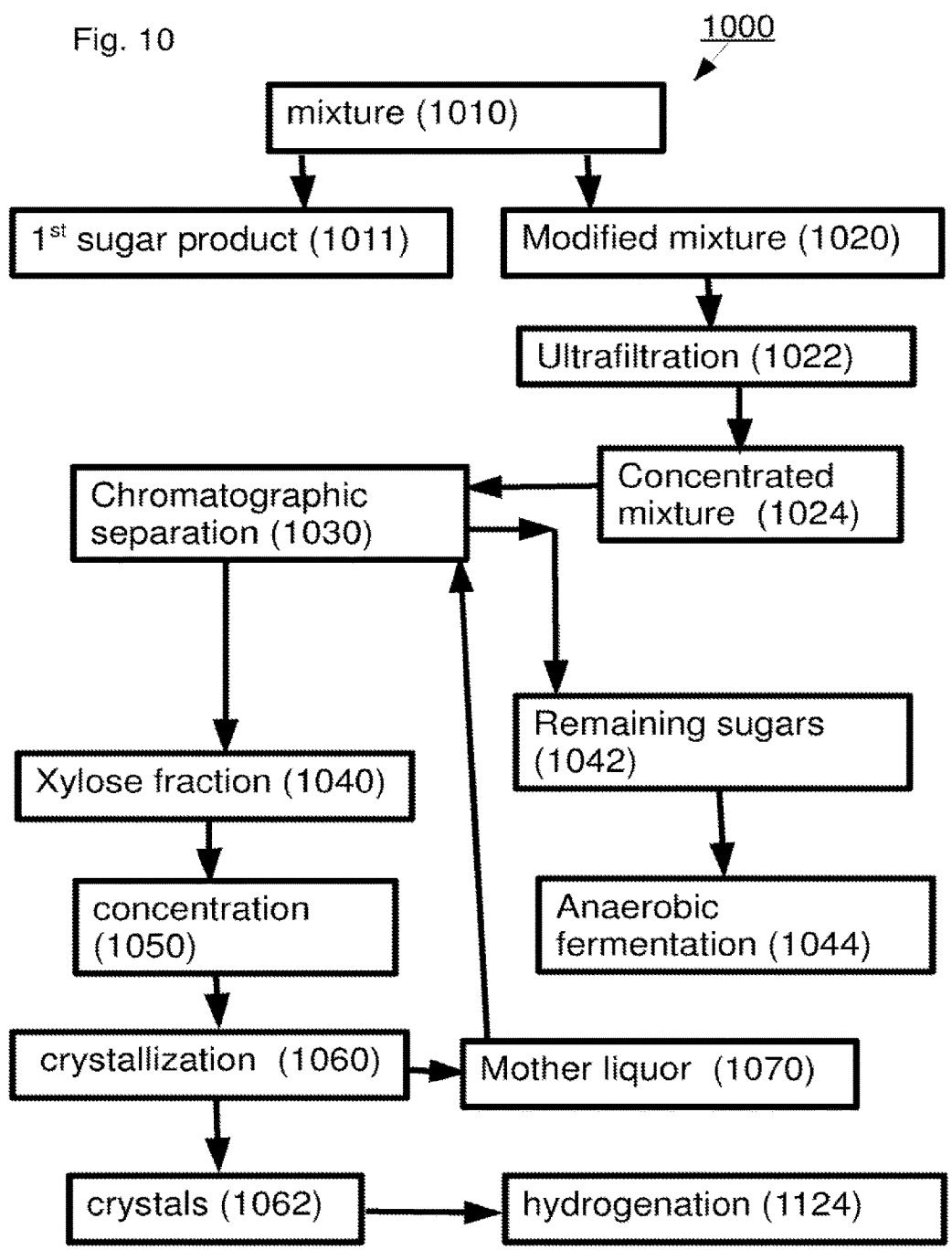
FIG. 10 is a simplified flow diagram of exemplary methods according to some embodiments of the invention.

FIG. 10 is a simplified flow diagram of an exemplary method according to some embodiments of the invention depicted generally as 1000. Depicted exemplary method 1000 produces a first sugar product 1011 and a product of a second sugar from a mixture 1010 of sugars. Optionally, the product of the second sugar is xylitol.

According to depicted exemplary method 1000, separation of $1^{st}$ sugar product 1011 from mixture 1010 produces a modified mixture 1020. In some exemplary embodiments of the invention, mixture 1010 is provided as an aqueous solution of sugars. In some exemplary embodiments of the invention, mixture 1020 is at least 35, optionally at least 40, optionally 45, optionally 50% or intermediate or greater percentages of xylose on a weight basis relative to total sugars. In the depicted exemplary embodiment, ultrafiltration 1022 of modified mixture 1020 produces a concentrated mixture 1024. In some exemplary embodiments of the invention, mixture 1024 includes 45, optionally 50, optionally 55, optionally 60% or intermediate or greater percentages of total sugars on a weight basis.

In the depicted exemplary embodiment, concentrated mixture 1024 is subject to chromatographic separation 1030. Chromatographic separation enriches the mixture for xylose, but may also dilute the mixture. In the depicted exemplary embodiment, xylose fraction 1040 includes 65, optionally 70, optionally 80, optionally 85% or intermediate or greater percentages of xylose on a weight basis relative to total sugars in the solution. Alternatively or additionally, fraction 1040 may include 2, optionally 3, optionally 4% or intermediate or greater percentages of mannose on a weight basis relative to total sugars in the solution. Alternatively or additionally, fraction 1040 may include 4, optionally 5, optionally 6% or intermediate or greater percentages of galactose on a weight basis relative to total sugars in the solution. Alternatively or additionally, fraction 1040 may include 1, optionally 2, optionally 3% or intermediate or greater percentages of arabinose on a weight basis relative to total sugars in the solution.

In the depicted exemplary embodiment, concentration 1050 increases the total sugar concentration to 65, optionally 70, optionally 75, optionally 80% or intermediate or greater percentages. Concentration 1050 brings xylose closer to its saturation point.

Crystallization 1060 produces crystals 1062 of a second sugar (e.g. xylose) and a mother liquor 1070. Optionally, an organic solvent, such an alcohol (e.g. ethanol or methanol) is added to the solution during crystallization 1060 to aid in precipitation of sugar crystals. Exemplary alcohol concentrations are provided above in the context of FIG. 7*a*.

Crystals 1062, which are substantially pure, can be subjected to hydrogenation 1124 to produce a corresponding alcohol. For example, if crystals 1062 are xylose crystals, hydrogenation will produce xylitol. Since hydrogenation is not typically a selective reaction, crystallization 1060 contributes to an ability to produce a desired sugar-alcohol at relatively high purity.

Returning now to crystallization 1060, the resultant mother liquor 1070 can be subject to additional chromatographic separation together with an additional amount of concentrated mixture 1024. Optionally, this allows at least a portion of xylose in mother liquor 1070 to be recovered by an additional round of crystallization 1060. Optionally, remaining sugars 1042 can be sent to anaerobic fermentation 1044 to produce an energy source, such as methane.

Exemplary Sugar Compositions

Some exemplary embodiments of the invention relate to sugar compositions which exist as production intermediates in various methods described herein.

For example, practice of the procedure outlined in FIG. 10 might produce, as an intermediate product, a sugar composition including at least 25; optionally 30; optionally 35% xylose by weight relative to total sugar concentration with a detectable amount of at least one alpha-bonded di-glucose and a detectable amount of at least one beta-bonded di-glucose. Optionally, the alpha-bonded di-glucose includes maltose and/or isomaltose and/or trehalose. Optionally, the beta-bonded di-glucose includes gentiobiose and/or sophorose and/or cellobiose. Compositions of this general type might occur at, for example, 1020 in FIG. 10. According to various exemplary embodiments of the invention the alpha bonded di-glucose is optionally present at a level of at least 10, optionally at least 50, optionally at least 100, optionally at least 500, optionally at least 1000 PPM or intermediate or greater levels. Alternatively or additionally, according to various exemplary embodiments of the invention the beta bonded di-glucose is optionally present at a level of at least 10, optionally at least 50, optionally at least 100, optionally at least 500, optionally at least 1000 PPM or intermediate or greater levels.

Optionally, the composition includes at least 40; optionally at least 42; optionally at least 45; optionally at least 47; optionally at least 50% total sugars. Compositions of this general type might occur at, for example, 1024 in FIG. 10.

Optionally, the composition is provided as a solution, for example an aqueous solution.

In some exemplary embodiments of the invention, the composition includes less than 90; optionally 80; optionally 70% xylose of total sugars on a weight basis.

Alternatively or additionally, in some exemplary embodiments of the invention the composition includes glucose at a concentration of at least 0.001; optionally at least 0.01; optionally at least 0.1% of total sugars on a weight basis. Alternatively or additionally, in some exemplary embodiments of the invention the composition includes glucose at a concentration of less than 5; optionally 3; optionally 1% of total sugars on a weight basis.

Alternatively or additionally, in some exemplary embodiments of the invention the composition includes at least 0.001; optionally 0.01; optionally 0.1% arabinose of total sugars on a weight basis.

Alternatively or additionally, in some exemplary embodiments of the invention the composition includes at least 0.001; optionally 0.0005; optionally 0.0001% non-volatile fermentation product on a weight basis. As used in this specification and the accompanying claims the term "non volatile fermentation products" includes but is not limited to: lactic acid, succinic acid, fatty acids, esters of fatty acids and proteins.

Alternatively or additionally, practice of the procedure outlined in FIG. 10 might produce, as an intermediate product, a sugar solution comprising (by weight relative to total sugar concentration) at least 60% xylose, at least 100 PPB of a marker molecule and 0.001% to 10% oligosaccharides. Optionally, the oligosaccharides include maltose and/or isomaltose and/or trehalose. Optionally, the oligosaccharides include gentiobiose, sophorose and cellobiose.

According to various exemplary embodiments of the invention the marker molecule includes at least one, optionally at least two, optionally at least three of furfural, hydroxy-methyl furfural, products of furfural or hydroxymethylfurfural condensation, color compounds formed on heating a sugar, levulinic acid, acetic acid, methanol, galacturonic acid, an alcohol of more than four carbon atoms, betaine, amino acids, proteins phosphate and glycerol.

Alternatively or additionally, the composition includes at least one; optionally at least two; optionally at least three fermentation residue(s). According to various exemplary embodiments of the invention the fermentation residue includes a component of an ingredient selected from the group consisting of sugar molasses, yeast extract and corn steep liquor. Optionally, fermentation residues can serve as marker molecules. Thus, there are marker molecules indicative of hydrolysis of a lignocellulosic substrate, and additional marker molecules indicative of fermentation of sugars in the resultant hydrolyzate.

Optionally, the composition includes glucose at a concentration of 0.001; optionally 0.01; optionally 0.1% of total sugars on a weight basis. Alternatively or additionally, the composition optionally includes glucose at a concentration of not more than 5; optionally 3; optionally 1% of total sugars on a weight basis.

Alternatively or additionally, the composition optionally includes arabinose at a concentration of at least 0.001; optionally 0.01; optionally 0.1% of total sugars on a weight basis.

Alternatively or additionally, the composition optionally includes 0.001% non-volatile fermentation product on a weight basis.

In some exemplary embodiments of the invention, the concentration of marker molecule does not exceed 0.5%. Optionally, a total concentration of the two, optionally the three, marker molecules does not exceed 0.5%.

Optionally, the composition includes at least 60% total sugars.

Optionally, the composition includes mannose and/or galactose and/or arabinose.

In some exemplary embodiments of the invention, the solution includes at least 3% mannose relative to total monosaccharides by weight.

Alternatively or additionally, the composition includes at least 5% galactose relative to total monosaccharides by weight.

Alternatively or additionally, the composition includes at least 2% arabinose relative to total monosaccharides by weight.

Compositions of this general type might occur at, for example, 1040 or 1050 in FIG. 10.

Additional Exemplary Composition

Some exemplary embodiments of the invention relate to sugar compositions which remain after glucose and xylose have been removed from an initial mixture 1010. These embodiments correspond, for example, to mother liquor 1070 in FIG. 10. This type of sugar composition includes at least one of:

alpha-bonded di-glucose;
beta-bonded di-glucose; and
arabinose;

together with 0.01%-20% xylose by weight relative to total sugar concentration and at least 100 PPB of a marker molecule.

Optionally, the composition is provided as a solution, for example an aqueous solution.

In some exemplary embodiments of the invention, the composition includes glucose at a concentration of at least 0.001% but not more than and 5%; optionally 3; optionally 1% of total sugars on a weight basis.

In some exemplary embodiments of the invention, the composition includes at least 0.001% non-volatile fermentation product on a weight basis.

In some exemplary embodiments of the invention, the alpha-bonded di-glucose includes at least one member of the group consisting of maltose, isomaltose and trehalose. Alternatively or additionally, in some exemplary embodiments of the invention, the beta-bonded di-glucose includes at least one member selected from the group consisting of gentiobiose, sophorose and cellobiose.

In some exemplary embodiments of the invention, the composition includes at least 40% total sugars.

Optionally, the marker molecule is selected from the group consisting of furfural, hydroxy-methyl furfural, products of furfural or hydroxy-methylfurfural condensation, color compounds formed on heating a sugar, levulinic acid, acetic acid, methanol, galacturonic acid, an alcohol of more than four carbon atoms, betaine, amino acids, proteins phosphate and glycerol. Optionally, the composition includes at least two, optionally at least three, marker molecules.

Alternatively or additionally, the composition includes at least one fermentation residue. Optionally, the fermentation residue includes a component of an ingredient selected from the group consisting of sugar molasses, yeast extract and corn steep liquor.

In some exemplary embodiments of the invention, the concentration of marker molecule does not exceed 0.5%. Optionally, a total concentration of the two, optionally the three, marker molecules does not exceed 0.5%.

Optionally, the composition includes mannose and/or galactose and/or arabinose.

In some exemplary embodiments of the invention, the solution includes at least 3% mannose relative to total monosaccharides by weight.

Alternatively or additionally, the composition includes at least 5% galactose relative to total monosaccharides by weight.

Alternatively or additionally, the composition includes at least 2% arabinose relative to total monosaccharides by weight.

Exemplary Logic Hierarchy

Figure 11:
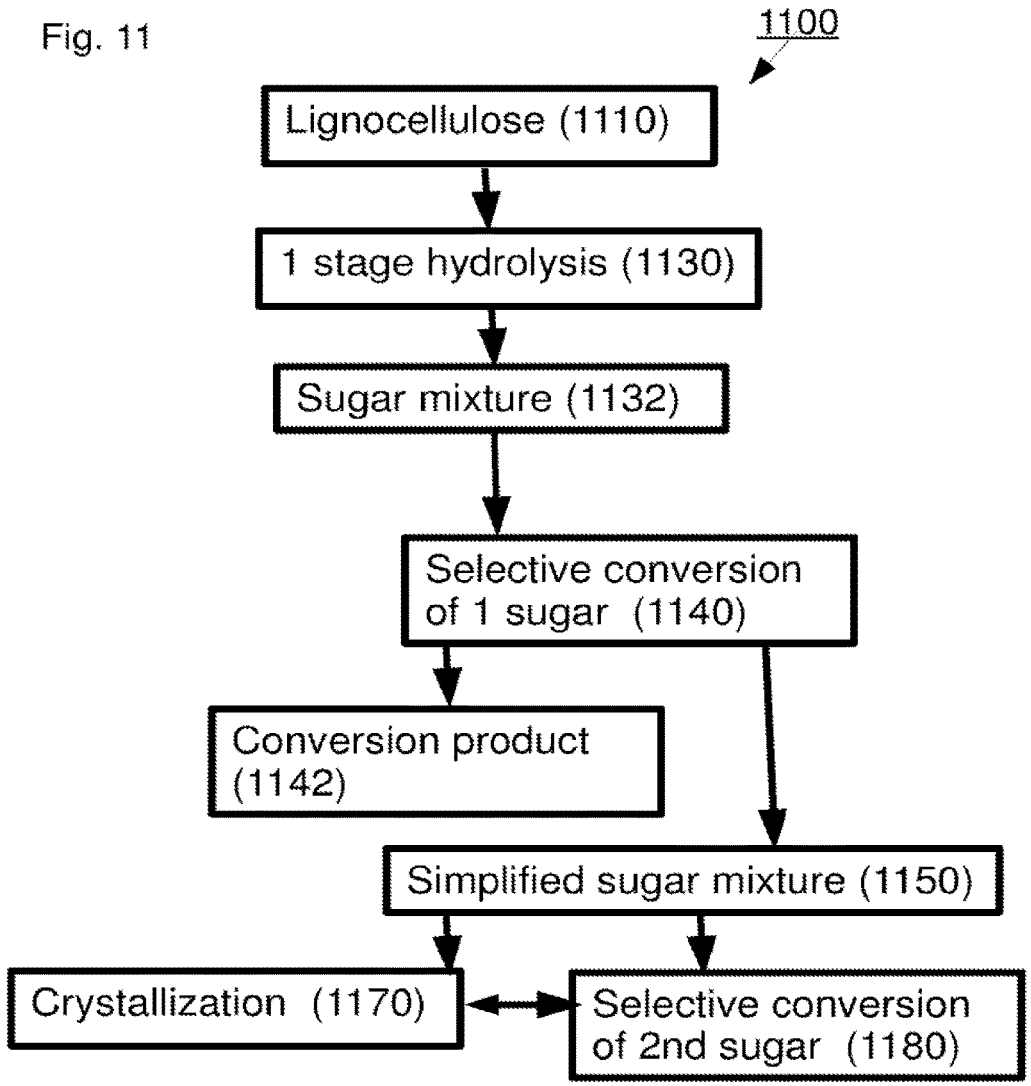
FIG. 11 is a logic hierarchy illustrating approaches to separating products of value from lignocelluloses.

FIG. 11 is a logic hierarchy illustrating approaches to separating products of value from lignocelluloses according to various exemplary embodiments of the invention indicated generally as 1100.

Exemplary embodiments depicted by method 1100 feature a one stage hydrolysis 1130 as described hereinabove in the context of FIG. 1. Such a hydrolysis produces a sugar mixture 1132. Without considering the quantitative yield of any specific sugars in mixture 1132, logic hierarchy 1100 includes various strategies for exploiting two or more sugar components in the mixture.

The depicted exemplary embodiments of the invention implement a selective conversion 1140 of one sugar to produce a conversion product 1142. In some exemplary embodiments of the invention, conversion 1140 includes a fermentation reaction. Optionally, conversion 1140 includes a chemical reaction and/or an enzymatic reaction not mediated by a microorganism. In some exemplary embodiments of the invention, conversion 1140 includes fermentation of glucoses and conversion product 1142 includes ethanol.

A simplified sugar mixture 1150 remains following separation of conversion product 1142. According to various exemplary embodiments of the invention it is possible to perform a selective conversion 1180 of a second sugar to form an additional product and/or to crystallize 1170 one or more second sugar(s). In one exemplary embodiment of the invention, xylose serves as a second sugar in simplified sugar mixture 1150. According to this embodiment, xylose can be crystallized 1170 and then selectively converted 1180 by hydrogenation to xylitol.

Regardless of the first sugar and second sugar employed, selective conversion 1140 followed by removal of conversion product 1142 contributes to an ability to selectively convert 1180 the second sugar by providing a simplified sugar mixture 1150.

In some exemplary embodiments of the invention, crystallization 1170 is performed to remove an interfering sugar from mixture 1150 and permit selective conversion 1180 of a desired second sugar to form a desired product.

It is expected that during the life of this patent many chromatographic separation techniques will be developed and the scope of the invention is intended to include all such new technologies a priori.

As used herein the term "about" refers to ±10%; optionally ±5%; optionally ±1%, optionally ±0.1%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims. Specifically, the invention has been described in the context of sugar mixtures resulting from acid hydrolysis of a lignocellulosic substrate but might also be used in the context of sugar mixtures formed by other processes.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following example, which is not intended to be limiting. Additionally, various embodiments and aspects of the present invention as delineated hereinabove and as claimed in the claims section below finds experimental support in the following examples.

EXAMPLE

Reference is now made to the following example, which together with the above descriptions, illustrates some embodiments of the invention in a non limiting fashion.

Example

Projected Compositions of Sugar Mixtures after Removal of Glucose by Fermentation and Distillation of Ethanol This example projects expected relative concentrations of monosaccharides in de-acidified hydrolyzates described in PCT IL 2011/000509, which is fully incorporated herein by reference, following removal of substantially all glucose by fermentation and distillation. This example also presumes that the fermentation reaction is specific and that other monosaccharides are not fermented to any significant degree.

In order to prepare the initial sugar mixtures, which would serve as the fermentation substrate, various lignocellulosic materials were introduced into a six stage hydrolysis reactor series in a counter-current operation as described in U.S. provisional application 61/483,777 filed May 9, 2011 and entitled "Hydrolysis systems and methods". This application is fully incorporated herein by reference.

Briefly, an aqueous solution of 42% HCl was introduced continually at a temperature of 10-15° C. for 24 hours. The hydrolyzate was collected, HCl was removed by extraction and the de-acidified hydrolyzate was concentrated to give a sugar composition. Analysis of actual results of monosaccharides are summarized in Table 1 (before). Disaccharide data is not presented but may be found in PCT IL 2011/000509. These actual results are calculated as % from sample's refractive total saccharides (%/RTS).

Table 1 also includes a calculated projection of relative sugar concentrations (as a % of total monosaccharides) following removal of glucose by fermentation/distillation (after).

The assayed substrates included two samples of pine wood, sugar cane bagasse and eucalyptus wood.

Results presented in Table 1 indicate that selective fermentation of glucose (optionally followed by removal of the resultant ethanol from the hydrolyzate mixture) increases the relative proportion of xylose. In the case of pine wood, xylose is the major monosaccharide component after glucose is eliminated.

Although di-saccharides and higher oligosaccharides account for a significant proportion of total sugars in the mixture, they are divided among a large number of different molecules. Alternatively or additionally, di-saccharides and higher oligosaccharides can be separated from a mixture of monosaccharides using chromatographic techniques. For this reason it seems that selective precipitation of xylose from glucose depleted mixtures will be feasible. It is envisioned that selective precipitation can be aided by cooling and/or addition of a non-aqueous solvent, such as ethanol. Optionally, ethanol produced by glucose fermentation can be used for this purpose.

TABLE 1

Monosaccharides in hydrolyzates of various substrates before and after selective removal of glucose

| substrate | status | other | Arabinose | Galactose | Glucose | Xylose | Mannose | Sum |
|---|---|---|---|---|---|---|---|---|
| Pine 1 | before | 0.1 (Rhamnose) | 1.6 | 2.7 | 27.7 | 7.0 | 7.4 | 46.5 |
|  | after | 0.5 | 8.5 | 14.3 | NA | 37.2 | 39.3 | NA |
| Pine 2 | before | NA* | 0.3 | 0.8 | 36.0 | 8.0 | 1.0 | 46 |
|  | after | NA* | 3.0 | 7.9 | NA | 79.2 | 9.9 | NA |
| Bagasse | before | 2.4 (fructose) | 2.2 | 7.2 | 48.7 | 4.9 | 4.8 | 70.2 |
|  | after | 11.2 | 10.2 | 33.5 | NA | 22.8 | 22.3 | NA |
| Eucalyptus | before | 3.38 (fructose) | 2.6 | 7.24 | 46.1 | 8.27 | 5.83 | 73.42 |
|  | after | 12.4 | 9.5 | 26.5 | NA | 30.3 | 5.83 | 21.33 |

*NA indicates not applicable

In those cases where crystallization of xylose proves difficult due to the presence of another sugar in a large amount (e.g. bagasse or eucalyptus where a large amount of galactoses is present) the interfering sugar can be removed prior to such crystallization if necessary. For example galactose has a solubility of 683 g/L (Wikipedia) in water while xylose has a solubility of 1250 g/L in water (Merck index). This suggests that galactose could be removed prior to xylose via selective crystallization of galactose.

The invention claimed is:

1. A lignocellulosic hydrolysate comprising:
   (a) at least 60% xylose by weight relative to total sugar concentration;
   (b) a total concentration of 0.00001% to 0.5% by weight relative to total sugar concentration of at least two marker molecules, wherein said marker molecules are selected from furfural, hydroxy-methylfurfural, and acetic acid;
   (c) 0.001% to 10% oligosaccharides by weight relative to total sugar concentration; and
   (d) at least 3% mannose by weight relative to total monosaccharides.

2. The lignocellulosic hydrolysate according to claim 1, comprising at least three marker molecules.

3. The lignocellulosic hydrolysate according to claim 1, comprising between 0.001% and 5% glucose of total sugars on a weight basis.

4. The lignocellulosic hydrolysate according to claim 1, comprising at least 0.001% arabinose of total sugars on a weight basis.

5. The lignocellulosic hydrolysate according to claim 1, wherein said oligosaccharides include at least one member selected from the group consisting of maltose, isomaltose and trehalose.

6. The lignocellulosic hydrolysate according to claim 1, wherein said oligosaccharides include at least one member selected from the group consisting of gentiobiose, sophorose and cellobiose.

7. The lignocellulosic hydrolysate according to claim 1, comprising at least one sugar selected from the group consisting of galactose and arabinose.

8. The lignocellulosic hydrolysate according to claim 1, comprising at least 5% galactose relative to total monosaccharides by weight.

9. The lignocellulosic hydrolysate according to claim 1, comprising at least 2% arabinose relative to total monosaccharides by weight.

10. The lignocellulosic hydrolysate according to claim 1, 3, or 9, wherein said marker molecules comprise furfural and hydroxy-methylfurfural.

11. The lignocellulosic hydrolysate according to claim 1, 3, 8, or 9, further comprising at least 100 PPB 2-ethylhexanol.

12. The lignocellulosic hydrolysate according to claim 1, comprising less than 90% of said xylose by weight relative to total sugar concentration.

13. The lignocellulosic hydrolysate according to claim 1, wherein said lignocellulosic hydrolysate is provided as an aqueous solution.

14. The lignocellulosic hydrolysate according to claim 13, wherein said lignocellulosic hydrolysate comprises at least 40% total sugars by weight.

15. The lignocellulosic hydrolysate according to claim 1, wherein said lignocellulosic hydrolysate has not been purified by crystallization.

16. The lignocellulosic hydrolysate according to claim 1, comprising at least 0.01% of said oligosaccharides by weight relative to total sugar concentration.

17. The lignocellulosic hydrolysate according to claim 1, comprising at least 0.1% of said oligosaccharides by weight relative to total sugar concentration.

18. The lignocellulosic hydrolysate according to claim 1 or 3, further comprising at least 100 PPB hexanol.

19. The lignocellulosic hydrolysate according to claim 1, wherein said marker molecules comprise acetic acid.

20. The lignocellulosic hydrolysate according to claim 1, further comprising levulinic acid or methanol.

21. A lignocellulosic hydrolysate comprising:
  (a) at least 60% xylose by weight relative to total sugar concentration;
  (b) a total concentration of 0.00001% to 0.5% by weight relative to total sugar concentration of at least three marker molecules, wherein said marker molecules are furfural, hydroxy-methylfurfural, and acetic acid;
  (c) 0.001% to 10% oligosaccharides by weight relative to total sugar concentration;
  (d) at least 2% arabinose by weight relative to total monosaccharides;
  (e) at least 3% mannose by weight relative to total monosaccharides; and
  (f) at least 100 PPB 2-ethylhexanol.

22. A lignocellulosic hydrolysate comprising:
  (a) at least 60% xylose by weight relative to total sugar concentration;
  (b) a total concentration of 0.00001% to 0.5% by weight relative to total sugar concentration of at least two marker molecules, wherein said marker molecules are selected from furfural, hydroxy-methylfurfural, and acetic acid;
  (c) 0.001% to 10% oligosaccharides by weight relative to total sugar concentration; and
  (d) at least 5% galactose by weight relative to total monosaccharides.

* * * * *

UNITED STATES PATENT AND TRADEMARK OFFICE
CERTIFICATE OF CORRECTION

PATENT NO. : 10,240,217 B2  
APPLICATION NO. : 14/033205  
DATED : March 26, 2019  
INVENTOR(S) : Robert Jansen et al.

Page 1 of 1

It is certified that error appears in the above-identified patent and that said Letters Patent is hereby corrected as shown below:

On the Title Page

Item (30), insert --Aug. 1, 2011 (WO).........PCT/US2011/046153--.

Signed and Sealed this  
Eighteenth Day of June, 2019

Andrei Iancu  
*Director of the United States Patent and Trademark Office*